United States Patent
Parks et al.

(10) Patent No.: US 6,699,886 B2
(45) Date of Patent: Mar. 2, 2004

(54) STORE OPERATED CALCIUM INFLUX INHIBITORS AND METHODS OF USE

(75) Inventors: Thomas P. Parks, San Mateo, CA (US); Don R. Baker, Orinda, CA (US)

(73) Assignee: Cellegy Pharmaceuticals, Inc., So. San Francisco, CA (US)

(*) Notice: Subject to any disclaimer, the term of this patent is extended or adjusted under 35 U.S.C. 154(b) by 50 days.

(21) Appl. No.: 10/160,977

(22) Filed: May 31, 2002

(65) Prior Publication Data

US 2003/0114353 A1 Jun. 19, 2003

Related U.S. Application Data

(60) Provisional application No. 60/295,129, filed on May 31, 2001, and provisional application No. 60/295,124, filed on May 31, 2001.

(51) Int. Cl.[7] .................... A61K 31/405; A61K 31/407; A61K 31/422; A61K 31/427; C07D 277/20
(52) U.S. Cl. .................. 514/340; 514/365; 514/374; 514/414; 514/415; 548/202; 548/235; 548/466; 546/277.4
(58) Field of Search ................................. 514/340, 374, 514/365, 414, 415; 548/202, 235, 466; 546/277.4

(56) References Cited

U.S. PATENT DOCUMENTS

| 4,231,938 A | 11/1980 | Monaghan et al. |
| 4,346,227 A | 8/1982 | Terahara et al. |
| 4,444,784 A | 4/1984 | Hoffman et al. |
| 4,739,073 A | 4/1988 | Kathawala |
| 5,006,530 A | 4/1991 | Angerbauer et al. |
| 5,032,590 A | 7/1991 | Hubsch et al. |
| 5,356,896 A | 10/1994 | Kabadi et al. |
| 6,048,875 A | 4/2000 | De Manteuil et al. |
| 6,126,947 A | 10/2000 | Savion et al. |

OTHER PUBLICATIONS

Database HCAPLUS on ACS. Accession No. 2002:249987, Guo, "Statin compositions for preventing and treating osteoporosis, cancer and hyperlipemia (translated)." Abstract, CN 1304724A, Jan. 19, 2001 (Translation).

*Primary Examiner*—Taofiq Solola
(74) *Attorney, Agent, or Firm*—Townsend and Townsend and Crew LLP

(57) ABSTRACT

The present invention provides store operated calcium influx inhibitor compounds, pharmaceutical compositions, and methods of use. The compounds are useful for treating an inflammatory disease or treating an inflammatory reaction. Preferably, compounds, compositions and methods of this invention are used for treatment of inflammatory skin, pulmonary, musculoskeletal, and gastrointestinal diseases, as well as autoimmune disorders, transplantation treatment, and osteoporosis.

37 Claims, 19 Drawing Sheets

Inhibition of JNK Phosphorylation by Lovastatin

A

1. Control
2. Lovastatin (20 µg/ml)
3. Ascomycin (1 ng/ml)
4. P+I
5. P+I+CP120
6. P+I+ascomycin

B

STORE OPERATED CALCIUM INFLUX INHIBITORS AND METHODS OF USE

CROSS-REFERENCE TO RELATED APPLICATIONS

The present application claims priority to U.S. Provisional Patent Application Nos. 60/295,129 and 60/295,124, both filed on May 31, 2001, the disclosures of which are hereby incorporated by reference in their entireties for all purposes.

BACKGROUND OF THE INVENTION

Inflammation represents a cascade of physiological and immunological reactions that nature has designed as the first cellular response to noxious stimuli in an effort to localize toxic materials or prevent tissue injury. Clinically, inflammation is a primary disease under acute conditions or is a manifestation of underlying pathophysiological abnormalities in chronic disease, characterized by classic signs of redness, pain, swelling and loss of function.

The inflammatory mediators IFN-gamma, IL-2, IL-4, IL-5, IL-8, and TNF-alpha have been implicated in the initiation and propagation of several inflammatory disorders. For example, IFN-gamma, which acts as a regulator of other pro-inflammatory cytokines, is the nexus of inflammation in autoimmune disorders such as multiple sclerosis (MS), insulin-dependent diabetes mellitus (IDDM), and rheumatoid arthritis (RA). Other IFN-gamma diseases include, vascular dementia, Alzheimer's disease, cellular and tissue damage seen in graft-versus-host disease, lupus, and the like. Furthermore, it has long been suspected that TNF-alpha serves as the primary cytokine orchestrating the inflammatory cascade of various debilitating diseases such as rheumatoid arthritis (RA), psoriasis, vasculitis, ischemic-reperfusion injury, and inflammatory bowel disease (IBD). In fact, anti-TNF antibodies and receptor decoys, i.e., Remicade and Enbrel have demonstrated efficacy in treating RA and IBD. Other TNF-alpha related diseases include, photoaging, leprosy, Leishmania, cachexia, endotoxemia, etc. Other disorders mediated by IFN-gamma and/or TNF-alpha include inflammatory bowel diseases (ulcerative colitis and Crohn's disease), atopic dermatitis, irritant contact dermatitis, osteoarthritis, asthma, chronic pelvic pain, inflammatory muscle disease, allergic rhinitis, vaginitis, interstitial cystitis, conjunctivitis, gastritis, chronic fatigue syndrome, scleroderma, osteoporosis, and numerous other hyperproliferative, inflammatory and degenerative disorders.

Hyperproliferative and inflammatory mucocutaneous disorders affect millions of individuals in the United States every year. Such disorders range from mild to life threatening, and include, for example, skin cancer, atopic dermatitis, psoriasis, and asthma and inflammatory bowel disease due to inflammation of the intestine wall. In addition, extrinsic skin aging can be caused by chronic inflammation and insufficient repair due to repetitive exposures to environmental insults, e.g., ultraviolet radiation. Aging of skin and in particular extrinsic aging can lead to any of a number of skin conditions requiring treatment.

Eczema, also called eczematous dermatitis, is one example of a common inflammatory mucocutaneous disorder. Eczema is a red, itchy, non-contagious inflammation of the skin that may be acute or chronic, with red skin patches, pimples, crusts, or scabs occurring either alone or in combination. The skin may be dry, or it may discharge a watery fluid, resulting in an itching or burning sensation. The affected skin may become infected. The various causes of eczematous dermatitis are classified as either external (irritations, allergic reactions, exposure to certain microorganisms, or chemicals), congenital (inherited predisposition), and environmental (stress, heat, and the like). Eczema may clear for years, only to reappear later at a different site.

Eczema can come in any of several forms, including, most commonly, atopic dermatitis. Atopic dermatitis is very common in all parts of the world. This chronically relapsing inflammatory skin disorder affects about ten percent of infants and three percent of the U.S. population overall. The disease can occur at any age, but is most common in infants to young adults (see, Hanifin J M et al., *Arch. Dermatol.*, 135(12):1551, 2000). The face is often affected first, then the hands and feet. Sometimes dry red patches appear all over the body. In older children the skin folds are most often affected, especially the elbow creases and behind the knees. In adults the face and hands are more likely to be involved. The condition usually improves in childhood or sometime before the age of 25. Most people with atopic dermatitis have family members with similar problems. Severity of the disease can be evaluated by EASI (Eczema Area Severity Index) score (see, Hanifin J M, *Exp. Dermatol.*, 10(1)11–18, 2001).

Another atopic disease, but which affects the lungs rather than the skin, is allergic asthma. Asthma is a chronic lung disease characterized by inflammation of the air passages (see, Busse W W, et al., "Asthma," *New Engl. J. Med.*, 344(5):350–362, 2001). This condition is estimated to affect about 15 million Americans and can be severe and result in death if not treated. A number of factors can exacerbate asthma including, e.g., rapid changes in temperature or humidity, allergies, upper respiratory infections, exercise, stress or smoking (cigarette). Typical treatments include bronchodilators which are given orally or delivered as an aerosol (inhaled), and, for the most difficult cases, corticosteroids. New, effective treatments without steroid-related side effects will be greatly welcome in this disease of increasing prevalence (see, Thomas P S, "Tumor Necrosis Factor-Alpha: The role of this multifunctional cytokine in asthma," *Immunol. Cell Biol.* 79(2):132–140, 2001).

Another example of a mucocutaneous inflammatory disorder is allergic rhinitis (hay fever). Allergic rhinitis is caused by a nasal inflammation in response to an irritant or an allergen. This condition can be seasonal or occur throughout the year (perennial). Typically, allergic rhinitis is treated by the administration of antihistamines either orally or locally (e.g., using nasal sprays). Other examples of mucocutaneous inflammatory disorders include those that involve cornification. Examples of such disorders include lamellar ichthyosis, acne, and rosacea.

Papulosquamous disorders are those characterized, as the name suggests, by scaly papules and plaques. Some of the more common papulosquamous disorders include psoriasis and lichen planus, both of which are manifested by a local inflammation of either the skin or a mucosal tissue (e.g., in the case of oral lichen planus).

Psoriasis is a persistent skin disease that got its name from the Greek word for "itch". The skin becomes inflamed, producing red, thickened areas with silvery scales, most often on the scalp, elbows, knees, and lower back. Severe psoriasis may cover large areas of the body. Psoriasis is not contagious, and has some genetic basis, as it is more likely to occur in people whose family members have it. In the United States about 2% of adults have psoriasis (four to five million people). Approximately 150,000 new cases occur each year. The cause of psoriasis is unknown. However, recent discoveries point to an abnormality in the functioning of key white cells in the blood stream triggering inflammation in the skin. Psoriasis is thus thought to be due, at least in part, to an abnormal immune reaction against some component of the skin. This leads to the local expression of cell adhesion molecules, up-regulation of inflammatory cytokines and growth factors, and to infiltration of inflammatory leukocytes into the tissue. As a result, the two hallmark features of psoriasis are local inflammation and epidermal hyperproliferation. The combination of hyperproliferation with incomplete terminal differentiation leads to the formation of a thickened stratum corneum or plaques.

In addition to psoriasis, other hyperproliferative skin disorders include, but are not limited to, basal cell carcinoma, squamous cell carcinoma (Bowen's disease), keratosis, such as actinic or seborrheic keratosis, and disorders of keratinization, such as ichthyosis and keratoderma. These hyperproliferative skin disorders result from the loss of the regulatory mechanisms that control the proliferation and differentiation of keratinocytes. Basal and squamous cell carcinomas are the most common forms of skin cancer. About 1.3 million cases of skin carcinomas are found in the United States per year. Both basal and squamous cell carcinoma affect the most external layer of the skin, the epidermis, and begin at the basal cell layer and at the upper cell layer of the epidermis, respectively. Although these skin carcinomas are slow growing and usually benign, they can, if not treated, grow and invade other tissues. In the year 2000, skin carcinomas will cause about 1,900 deaths in the United States.

In addition to changes resulting from inflammatory and hyperproliferative disorders, the appearance and characteristics of the skin also change as the body ages. Chronologically aged (intrinsically aged) mucocutaneous surfaces show a slight atrophy of the epidermis with straightening of the rete pegs thus weakening the dermal/epidermal junction measured by a decrease in the threshold for suction bullae. There is a moderate decrease in the number of Langerhans cells. Dryness of the skin is a common phenomenon. In the dermis there is a decrease in cell numbers and a decrease in elastic fibers and thus in skin elasticity. Capillaries are also fragile as evidenced by bruisability. Collagen metabolism is slower, and there is a progressive lowering in concentration of glycosaminoglycans. Sagging of the skin occurs. There is a decreased ability to mount inflammatory responses and an increase in the time of healing after injury.

Aging is accelerated in those areas exposed to environmental insults, such as irritating substances, and sunlight (ultraviolet radiation), due to the development of local skin inflammation. The skin aging process resulting from exposure to sunlight is known as "photoaging." Photoaging accounts for about 80% of the visible changes of skin aging. It induces deep wrinkles not erased by stretching, pigmentary alterations with areas of hyper- and hypo-pigmentation (actinic lentigines and leukodermas), and a variety of benign, premalignant, and malignant neoplasms. The dermis shows evidence of chronic inflammation with increased cellularity and enlarged fibroblasts. Elastotic degeneration, known as the "grenz" zone, occurs in parts of the upper dermis. This zone is occupied by a basophilic fibrous material separating the dermis from the epidermis and is interpreted as a repair area. Glycosaminoglycan and elastin concentrations are increased.

Skin inflammation and irritation can also be caused by, for example, transdermal drug delivery, irritating drug delivery enhancers or irritating drug substances that are found in pharmaceutical products as well as in skin care products. Examples of irritating drug substances include, but are not limited to, retinoic acid and its derivatives and analogs, alpha-hydroxy acids and anthralin. The discomfort associated with the inflammation and/or irritation may affect the patient's compliance with the treatment and comfort during drug delivery.

Inflammation of other muco-epithelial membranes could also lead to severely debilitating disorders. The mucosal epithelium of the alimentary tract represents a crucial barrier to a broad spectrum of noxious and immunogenic substances within the intestinal lumen. An impairment of the integrity of the mucosal epithelial barrier is observed in the course of various intestinal disorders including inflammatory bowel diseases (IBD), celiac disease, intestinal infections, and various other diseases. Ulcerative colitis (UC) and Crohn's disease (CD), collectively termed inflammatory bowel disease (IBD), are chronic spontaneously relapsing enteropathies of unknown etiology. Pharmacotherapy for IBD has essentially been unchanged for over twenty years, with therapy based around 5-aminosalicylic acid (5-ASA) preparations, corticosteroids, antibiotics and immunosuppression (see, *Scrip Reports on Gastrointestinal Disorders: New Therapies for the New Millennium*, 2000). The most commonly used immuno-suppressive agents include azathioprine, methotrexate, and 6-mercaptopurine. Much of the controversy surrounding optimal use of these drugs in IBD arises as a consequence of methodological deficiencies in many of the early trials combined with the difficulty in consistent patient selection due to the heterogeneous nature of both UC and CD. While these therapies are able to suppress acute disease activity, there are significant side effect profiles. Furthermore, 20–30% of the IBD patients are steroid-resistant. The most recent report on the efficacy of infliximab has generated a great deal of excitement, although the long-term usefulness is unknown. For certain patients, this treatment could be prohibitive since the cost for each treatment approximates $1,000. A cost-effective therapy which can also be used for long-term maintenance treatment will greatly improve morbidity and mortality and thus, overall quality-of-life of the IBD patients.

If the inflammation occurs at the urogenital epithelium, vaginitis, interstitial cystitis, and the like, may develop. Vaginitis is a common gynecologic disorder that is responsible for 10 million office visits to physicians each year. Infectious vaginitis is the most common cause of a vaginal discharge, but other important diagnostic considerations include infectious cervicitis, a physiologic discharge, atrophic vaginitis, and allergic or irritant vaginitis (see, Quan M, *Clin. Cornerstone*, 3(1):36–47, 2000). Interstitial cystitis (IC) is a disorder of unknown etiology with few effective therapies. Interstitial cystitis (IC) is a painful, sterile, disorder of the urinary bladder characterized by urgency, frequency, nocturia and pain. IC occurs primarily in women but also in men with recent findings indicating that chronic, abacterial prostatitis may be a variant of this condition. The prevalence of IC has ranged from about 8–60 cases/100,000 female patients depending on the population evaluated. About 10% of patients have severe symptoms that are associated with Hunner's ulcers on bladder biopsy; the rest could be grouped in those with or without bladder inflammation. Symptoms of IC are exacerbated by stress, certain foods and ovulatory hormones. Many patients also experience allergies, irritable bowel syndrome (IBS) and migraines. There have been various reports indicating dysfunction of the bladder glycosaminoglycan (GAG) protective layer and many publications showing a high number of activated bladder mast cells. Increasing evidence suggests that neurogenic inflammation and/or neuropathic pain is a major component of IC pathophysiology. Approved treatments so far include intravesical administration of dimethylsulphoxide (DMSO) or oral pentosanpolysulphate (PPS). However, none of these therapies were proven effective in treating a large proportion of patients afflicted with IC.

Osteoporosis afflicts 75 million persons in the United States, Europe and Japan and results in more than 1.3 million fractures annually in the United States. Osteoporosis is a disease characterized by decreased bone mass and increased fragility of the remaining bone (see, Dempster et al, J Bone Mineral Res., 1:19-, 1986; Rodan G A et al. 13:S3–S6, 1992). This low bone mass and increased bone fragility leads to a high incidence of fractures experienced by osteoporosis patients. Because osteoporosis is usually asymptomatic until a fracture occurs, family physicians must identify the appropriate timing and methods for screening those at risk. Prevention is the most important step, and women of all ages should be encouraged to take 1,000 to 1,500 mg supplemental calcium daily, participate in regular weight-bearing exercise, avoid medications known to compromise bone density, institute hormone replacement therapy at menopause unless contraindicated and avoid tobacco and excessive alcohol intake. Therapy for osteoporosis is principally centered on the use of agents that block bone resorption and supplementation with vitamin D and calcium. Although these drugs, bisphosphonates, are effective in reducing the risk of subsequent fractures, and modestly increasing bone density, most patients being treated for osteoporosis still have low bone mass and are at greater risk of fracture. Furthermore, due to the poor intestinal absorption of all bisphosphonates, it is crucial to administer these drugs at least 90 minutes before and after meals and to take them with water only (see, Goodman & Gilman's *The Pharmacological Basis of Therapeutics*, $9^{th}$ Edition, Hardman J G, et al., McGraw-Hill, 1996). With high dose of bisphosphonate use, gastrointestinal discomforts, such as diarrhea, nausea, and the like occur in some patients (Physicians' Desk Reference, 2001, Medical Economics Company, Inc., Montvale, N.J.). There is definitely an unmet medical need for safe and effective therapy which is suitable for long term treatment for osteoporosis.

Osteoclast activation is a critical cellular process for pathological bone resorption, such as erosions in rheumatoid arthritis (RA) or generalized bone loss. Among many factors triggering excessive osteoclast activity, IL-1, tumor necrosis factor (TNF)-alpha and IFN-gamma play a central role (see, Roux S et al. *Arthritis Res* 2(6):451–456, 2000; Pratelli L et al. *Minerva Med* 90(4):101–9, 1999; Evans et al. *J Bone Miner Res* Mar. 11(3):300–5, 1996). In fact, a study demonstrates that alendronate reduces bone turnover in early rheumatoid arthritis stage and may have a possible antiarthritic effect, or anti-inflammatory effect, in addition to its biological influence on osteoclast activity/function (see, Cantatore F P et al. *J Rheumatol* 26(11):2318–23, 1996). It follows that compounds which can effectively block IL-1, TNF and IFN-gamma production may provide alternative medical treatment for osteoporosis, especially osteoporosis which is induced by inflammation, such as RA.

In principle, the inflammatory and immune response can be regulated through the use of drugs (see, Goodman & Gilman's "The Pharmacological Basis of Therapeutics" eds. Hardman et al. Ninth Edition, McGraw-Hill Publishing, 1996). Unfortunately, certain anti-inflammatory drugs presently available produce cytotoxic effects that reflect their initial employment as cancer chemotherapeutics, typically anti-neoplastics. Such drugs effectively kill cells indiscriminately. Corticosteroids are also a mainstay of anti-inflammatory therapy. However, they manifest significant adverse effects, such as inducing Cushingoid features, skin thinning, increased susceptibility to infection, and suppression of the hypothalamic-pituitary-adrenal axis. The use of other immunosuppressive agents such as cyclosporin A can also induce the development of severe side effects, e.g., hypertension and nephrotoxicity. Clearly, new treatments for inflammatory disorders are needed.

Recently, it is becoming increasingly clear that statins, the 3-hydroxy-3-methylglutaryl coenzyme A (HMG-CoA) reductase inhibitors that are the most commonly used agents for treatment of hypercholesteremia, have clinical benefits beyond their ability to lower cholesterol. For example, pravastatin significantly reduces the incidence of organ rejection, transplant vasculopathy, and natural killer (NK) cell cytotoxicity in recipients of heart (Kobashigawa et al. 1995) and kidney transplants (Katznelson et al. 1996). In another heart transplant study, simvastatin was shown to decrease the progression of transplant vasculopathy and to increase patient survival (Wenke et al. 1997), suggesting that the effects of statins in transplant patients may be a drug class effect. In heart and kidney transplant patients, pravastatin treatment significantly inhibits NK cell cytotoxicity beyond that obtained with the baseline regimen, consisting of prednisone, azathioprine, and cyclosporine. It has been suggested that synergism between statins and cyclosporin A could potentially be the basis for the immunosuppression uniquely observed in transplant patients (Katznelson, 1999). In support of this hypothesis, Kurakota et al. (1996) demonstrate that clinically relevant concentrations of simvastatin which are not immunosuppressive themselves, are capable of significantly enhancing the inhibition of human T-cell responses by cyclosporin A in vitro.

Statins have inhibitory effects on lymphocyte proliferation which are dose-dependent and reversed by addition of mevalonate, the immediate product of HMG-CoA reductase, but not cholesterol (Yachnin 1982). As in other cell types, statins cause cell cycle arrest of lymphocytes in G1 (see, Chakrabarti et al., 1991; Vogt et al. 1996; Tatsuno et al. 1997). Reedquist et al. (Reedquist et al. 1995) has also reported that lovastatin inhibits murine B cell proliferation and differentiation, and induces apoptosis following LPS treatment.

As mentioned previously, glucocorticoids, antimetabolites, and cyclosporin-like immunosuppressants, currently the mainstays of treatment for inflammation, are self-limiting due to untoward side effects. Furthermore, treatments are often ineffective and in some cases, no effective treatment exists. In view of the foregoing, it is readily apparent that there is a great need for compounds and methods for effective treatment for a large number of inflammatory disorders. The present invention addresses these and other needs.

SUMMARY OF THE INVENTION

The present invention provides compounds, compositions and methods for the treatment of inflammatory disorders. The compounds of the present invention are preferably store-operated calcium influx (SOC) inhibitors which inhibit calcium uptake into non-excitable cells in response to stimulus-mediated depletion of intracellular calcium storage pools. The SOC inhibitors preferably inhibit one or more of the following: calcium-dependent activation of nuclear factor of activated T cells (NFAT), nuclear factor kB (NF-kB), the stress kinases c-Jun N-terminal kinase (JNK) and exocytosis, resulting in the release or elaboration of inflammatory mediators. Advantageously, the compounds of the present invention can be used to treat various inflammatory disorders and can be formulated in various ways as pharmaceutical compositions and used in methods for optimal delivery and efficacy.

As such, the present invention provides methods for treating an inflammatory disease or reducing an inflammatory reaction, comprising administering a SOC inhibitor to inhibit calcium uptake into a cell, thereby treating the inflammatory disease or reducing the inflammatory reaction. Inflammatory diseases to be treated include skin disorders including, but not limited to, atopic dermatitis, psoriasis, neurogenic inflammation, skin photodamage, a cell carcinoma such as basal cell carcinoma, keratosis, and a disorder of keratinization, and inflammatory pulmonary diseases including asthma, allergic rhinitis, chronic obstructive pulmonary disease, and adult respiratory distress syndrome. Other diseases include inflammatory musculoskeletal conditions, inflammatory gastrointestinal conditions, autoimmune diseases, and transplantation treatments. Examples of SOC inhibitors include for example, novel compounds of the present invention and statins in the δ-lactone form such as lovastatin, mevastatin, and simvastatin.

In another embodiment, the present invention provides a compound having the formula:

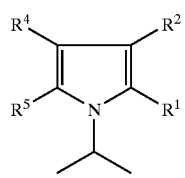

I wherein:
- $R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;
- $R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy;
- $R^4$ is an optionally substituted alkyl; and
- $R^5$ is an optionally substituted alkyl, or alternatively, $R^4$ and $R^5$ and the carbons to which they are attached, joined to form an optionally substituted aryl or optionally substituted heteroalkyl 5- or 6 membered ring. In an especially preferred embodiment, $R^2$ is optionally substituted aryl, such as p-fluorophenyl.

In another embodiment, the present invention provides a compound having the formula:

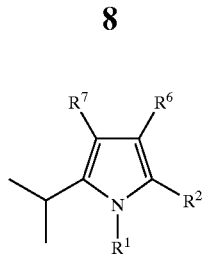

II wherein:
- $R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;
- $R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy;
- $R^6$ is a member selected from an optionally substituted alkyl, optionally substituted aryl, optionally substituted arylalkyl, optionally substituted heteroarylalkyl, optionally substituted heteroarylalkoxy; and
- $R^7$ is a member selected from an optionally substituted alkyl, optionally substituted aryl, optionally substituted arylalkyl, optionally substituted heteroarylalkyl, optionally substituted heteroarylalkoxy; or alternatively, $R^6$ and $R^7$ and the carbons to which they are attached, joined to form an optionally substituted aryl or optionally substituted heteroalkyl 5- or 6 membered ring. In an especially preferred embodiment, $R^2$ is optionally substituted aryl, such as p-fluorophenyl.

In yet another embodiment, the present invention provides a compound having the formula:

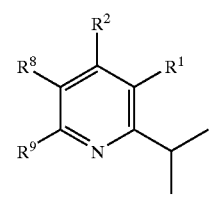

III wherein:
- $R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;
- $R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy;
- $R^8$ is a member selected from an optionally substituted alkyl, optionally substituted aryl, optionally substituted arylalkyl, optionally substituted heteroarylalkyl, and optionally substituted heteroarylalkoxy;

$R^9$ is a member selected from an optionally substituted alkyl, optionally substituted aryl, optionally substituted arylalkyl, optionally substituted heteroarylalkyl, and optionally substituted heteroarylalkoxy; or alternatively, $R^8$ and $R^9$ and the carbons to which they are attached, joined to form an optionally substituted aryl or optionally substituted heteroalkyl 5- or 6- membered ring. In an especially preferred embodiment, $R^2$ is optionally substituted aryl, such as p-fluorophenyl.

In still yet another embodiment, the present invention provides a compound having the formula:

IV wherein:
$R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

$R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy; and Q is a member selected from the group of hydrogen, optionally substituted alkyl, optionally substituted alkoxy and hydroxy. In an especially preferred embodiment, $R^2$ is optionally substituted aryl, such as p-fluorophenyl.

In still yet another embodiment, the present invention provides a compound having the formula:

V wherein:
$R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

$R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy; and Q is a member selected from hydrogen, optionally substituted alkyl, optionally substituted alkoxy and hydroxy. In an especially preferred embodiment, $R^2$ is optionally substituted aryl, such as p-fluorophenyl.

In another embodiment, the present invention provides a pharmaceutical composition, the pharmaceutical composition comprising:
a compound having the formula:

I wherein:
$R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

$R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy;

$R^4$ is an optionally substituted alkyl;

$R^5$ is an optionally substituted alkyl, or alternatively, $R^4$ and $R^5$ and the carbons to which they are attached, joined to form an optionally substituted aryl or optionally substituted heteroalkyl 5- or 6 membered ring; and a pharmaceutically acceptable excipient therefor.

In another embodiment, the present invention provides a pharmaceutical composition, the pharmaceutical composition comprising: a compound having the formula:

II wherein:
$R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

$R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, and optionally substituted heteroarylalkoxy;

R⁶ is a member selected from an optionally substituted alkyl, optionally substituted aryl, optionally substituted arylalkyl, optionally substituted heteroarylalkyl, optionally substituted heteroarylalkoxy;

R⁷ is a member selected from the group consisting of an optionally substituted alkyl, optionally substituted aryl, optionally substituted arylalkyl, optionally substituted heteroarylalkyl, and optionally substituted heteroarylalkoxy; or alternatively, R⁶ and R⁷ and the carbons to which they are attached, joined to form an optionally substituted aryl or optionally substituted heteroalkyl 5- or 6 membered ring; and a pharmaceutically acceptable excipient therefor.

In yet another embodiment, the present invention provides a pharmaceutical composition, the pharmaceutical composition comprising: a compound having the formula:

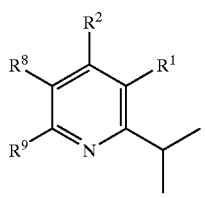

III wherein:

R¹ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R² is a member selected from of optionally substituted ($C_1$–$C_6$)alkyl, optionally substituted ($C_1$–$C_6$)alkoxy, acyl, optionally substituted aryl, optionally substituted arylalkyl, optionally substituted heteroarylalkyl, optionally substituted heteroarylalkoxy;

R⁸ is a member selected from an optionally substituted alkyl, optionally substituted aryl, optionally substituted arylalkyl, optionally substituted heteroarylalkyl, and optionally substituted heteroarylalkoxy;

R⁹ is a member selected from an optionally substituted alkyl, optionally substituted aryl, optionally substituted arylalkyl, optionally substituted heteroarylalkyl, and optionally substituted heteroarylalkoxy; or alternatively, R⁸ and R⁹ and the carbons to which they are attached, joined to form an optionally substituted aryl or optionally substituted heteroalkyl 5- or 6 membered ring; and a pharmaceutically acceptable excipient therefor.

In still another embodiment, the present invention provides a pharmaceutical composition, comprising: a compound having the formula:

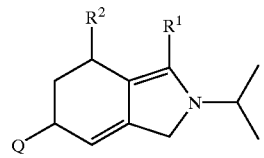

IV wherein:

R¹ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R² is a member selected from optionally substituted ($C_1$–$C_6$)alkyl, optionally substituted ($C_1$–$C_6$)alkoxy, acyl, optionally substituted aryl, optionally substituted arylalkyl, optionally substituted heteroarylalkyl, and optionally substituted heteroarylalkoxy;

Q is a member selected from the group consisting of hydrogen, optionally substituted alkyl, optionally substituted alkoxy and hydroxy; and a pharmaceutically acceptable excipient therefor.

In still yet another embodiment, the present invention provides a pharmaceutical composition, comprising: a compound having the formula:

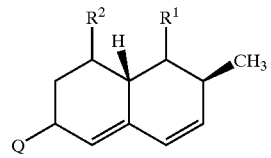

V wherein:

R¹ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R² is independently a member selected from optionally substituted ($C_1$–$C_6$)alkyl, optionally substituted ($C_1$–$C_6$)alkoxy, acyl, optionally substituted aryl, optionally substituted arylalkyl, optionally substituted heteroarylalkyl, and optionally substituted heteroarylalkoxy;

Q is a member selected from the group consisting of hydrogen, optionally substituted alkyl, optionally substituted alkoxy and hydroxy; and pharmaceutically acceptable excipient therefor.

In still yet another embodiment, the present invention provides a method for blocking calcium influx from the extracellular space, comprising: contacting a cell with a store operated calcium influx (SOC) inhibitor, thereby blocking calcium influx from the extracellular space. The method can be carried out in vivo or in vitro.

In certain aspects, the SOC inhibitor is a compound having the formula:

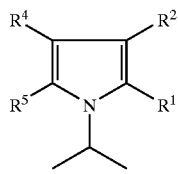

I wherein:
R$^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R$^2$ is a member selected from optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy;

R$^4$ is selected from an optionally substituted alkyl; and

R$^5$ is selected from an optionally substituted alkyl, or alternatively, R$^4$ and R$^5$ and the carbons to which they are attached, joined to form an optionally substituted aryl or optionally substituted heteroalkyl 5- or 6- membered ring.

In another embodiment, the SOC inhibitor is a compound having the formula:

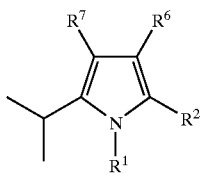

II wherein:
R$^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R$^2$ is a member selected from optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy;

R$^6$ is a member selected from an optionally substituted alkyl, optionally substituted aryl, optionally substituted arylalkyl, optionally substituted heteroarylalkyl, optionally substituted heteroarylalkoxy; and R$^7$ is a member selected from an optionally substituted alkyl, optionally substituted aryl, optionally substituted arylalkyl, optionally substituted heteroarylalkyl, optionally substituted heteroarylalkoxy; or alternatively, R$^6$ and R$^7$ and the carbons to which they are attached, joined to form an optionally substituted aryl or optionally substituted heteroalkyl 5- or 6- membered ring.

In yet another embodiment, the SOC inhibitor is a compound having the formula:

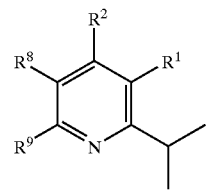

III wherein:
R$^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R$^2$ is a member selected from optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy;

R$^8$ is a member selected from an optionally substituted alkyl, optionally substituted aryl, optionally substituted arylalkyl, optionally substituted heteroarylalkyl, and optionally substituted heteroarylalkoxy;

R$^9$ is a member selected from an optionally substituted alkyl, optionally substituted aryl, optionally substituted arylalkyl, optionally substituted heteroarylalkyl, and optionally substituted heteroarylalkoxy; or alternatively, R$^8$ and R$^9$ and the carbons to which they are attached, joined to form an optionally substituted aryl or optionally substituted heteroalkyl 5- or 6- membered ring.

In still yet another embodiment, the SOC inhibitor is a compound having the formula:

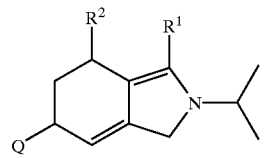

IV wherein:
R$^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

R$^2$ is a member selected from optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy; and Q is a member selected from the group consisting of hydrogen, optionally substituted alkyl, optionally substituted alkoxy and hydroxy.

In still yet another embodiment, the SOC inhibitor is a compound having the formula:

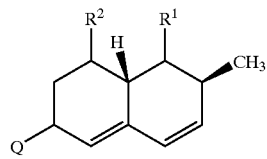

wherein:

$R^1$ is a member selected from optionally substituted alkyl, optionally substituted alkoxy, optionally substituted alkylene having at least 2 sites of unsaturation, optionally substituted aryl, optionally substituted arylalkyl, optionally substituted heteroarylalkyl, optionally substituted heteroarylthioalkyl, optionally substituted heteroaryliminooxyalkyl, optionally substituted heterocyclyl, optionally substituted oximinoaryl and optionally substituted heteroarylalkoxy;

$R^2$ is a member selected from optionally substituted $(C_1-C_6)$alkyl, optionally substituted $(C_1-C_6)$alkoxy, acyl, optionally substituted aryl, optionally substituted arylalkyl, optionally substituted heteroarylalkyl, optionally substituted heteroarylalkoxy; and Q is a member selected from hydrogen, optionally substituted alkyl, optionally substituted alkoxy and hydroxy.

These and other aspects and advantages of the present will become more apparent when read with the figures and detailed description, which follows.

DEFINITIONS

Unless otherwise stated, the following terms used in the specification and claims have the meanings given below:

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene (—$CH_2$—), propylene (—$CH_2CH_2CH_2$—), chloroethylene (—$CHClCH_2$—), 2-thiobutene —$CH_2CH(SH)CH_2CH_2$, 1-bromo-3-hydroxyl-4-methylpentene (—$CHBrCH_2CH(OH)CH(CH_3)CH_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "heterocyclyl," by itself or in combination with another term, means, a cyclic hydrocarbon radical, or combinations thereof, consisting of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S may be placed at any interior position of the heterocyclyl group. Examples of heterocyclyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "heteroaryl," means an aromatic substituent which can be a single ring or multiple rings (up to three rings) which are fused together or linked covalently. The rings may each contain from 1 to four heteroatoms selected from N, O, and S, wherein the nitrogen and sulfur atoms are optionally oxidized, and the nitrogen atom(s) are optionally quaternized. The groups can be attached to the remainder of the molecule through a heteroatom. Non-limiting examples of heteroaryl groups include aminobenzoheteroazolyl, 2-azanaphthalenyl, bezoxazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl 6-quinolyl, thiobenzoxazolyl, thiobenzothiazolyl and thiobenzimidazolyl. Substituents for each of the above noted herteoaryl ring systems listed above. are selected from the group of acceptable substituents described below. The term "heteroarylalkyl" is meant to include those radicals in which an heteroaryl group is attached to an alkyl group (e.g., pyridylmethyl, phenoxymethyl, 2-pyridyloxymethyl, 3-(1-naphthyloxy)propyl, and the like).

The phrase "optionally substituted" means that each of the above radicals (e.g., "alkyl," and "aryl") are meant to include both substituted and unsubstituted forms of the indicated radical.

The terms "treatment," "therapy," and the like, include, but are not limited to, changes in the recipient's status. The changes can be either subjective or objective and can relate to features such as symptoms or signs of the disease or condition being treated. For example, if the patient notes decreased itching, reduced redness, or decreased pain, then successful treatment has occurred. Similarly, if the clinician notes objective changes, such as by histological analysis of a biopsy sample, then treatment has also been successful. Alternatively, the clinician may note a decrease in inflammatory lesions or other abnormalities upon examination of the patient. This would also represent an improvement or a successful treatment. Prevention of deterioration of the recipient's status is also included by the term. Therapeutic benefit includes any of a number of subjective or objective factors indicating a response of the condition being treated as discussed herein.

"Drug", "pharmacological agent", "pharmaceutical agent", "active agent", and "agent" are used interchangeably and are intended to have their broadest interpretation as to any therapeutically active substance which is delivered to a living organism to produce a desired, usually beneficial effect. In general, this includes therapeutic agents in all of the major therapeutic areas, also including proteins, peptides, oligonucleotides, and carbohydrates as well as inorganic ions, such as calcium ion, lanthanum ion, potassium ion, magnesium ion, phosphate ion, and chloride ion.

The term "anti-inflammatory agent" and the like, include, but are not limited to, agents which reduce the extent and/or severity of inflammation and/or other immune responses. Reduction in the extent and/or severity of immune responses includes reduction in redness, swelling, fever, tissue damage, pain, and/or itch. Also included are agents that prevent inflammation from occurring that would otherwise be induced in response to a stimulus, for example, a drug or cosmetic that induces inflammation as a side effect. As used herein, the term can also include anti-allergens, anti-sensitizers, and anti-irritants.

As used herein, the phrase "a store operated calcium influx inhibitor" ("SOC") denotes a therapeutic agent which inhibits calcium uptake into a cell. A SOC inhibitor preferably inhibits the activation of nuclear factor of activated T cells ("NFAT"). Preferably, store-operated calcium influx (SOC) inhibitors inhibit calcium uptake into non-excitable cells in response to stimulus-mediated depletion of intracellular calcium storage pools. The SOC inhibitors preferably inhibit one or more of the following: calcium-dependent activation of nuclear factor of activated T cells (NFAT), nuclear factor kB (NF-kB), the stress kinases c-Jun N-terminal kinase (JNK) and exocytosis, resulting in the release or elaboration of inflammatory mediators. Examples of SOC inhibitors include for example, novel compounds of the present invention and statins in the δ-lactone form such as lovastatin, mevastatin, and simvastatin. Statins are known to be HMG-CoA reductase inhibitors acting in an open-chain form. Stains which are SOC inhibitors act at higher concentrations compared to the HMG-CoA reductase inhibition and are present in the δ-lactone form. SOC inhibitors are active in the SOC inhibition assay set forth herein.

DETAILED DESCRIPTION OF THE INVENTION AND PREFERRED EMBODIMENTS

I. Introduction

Figure 1:
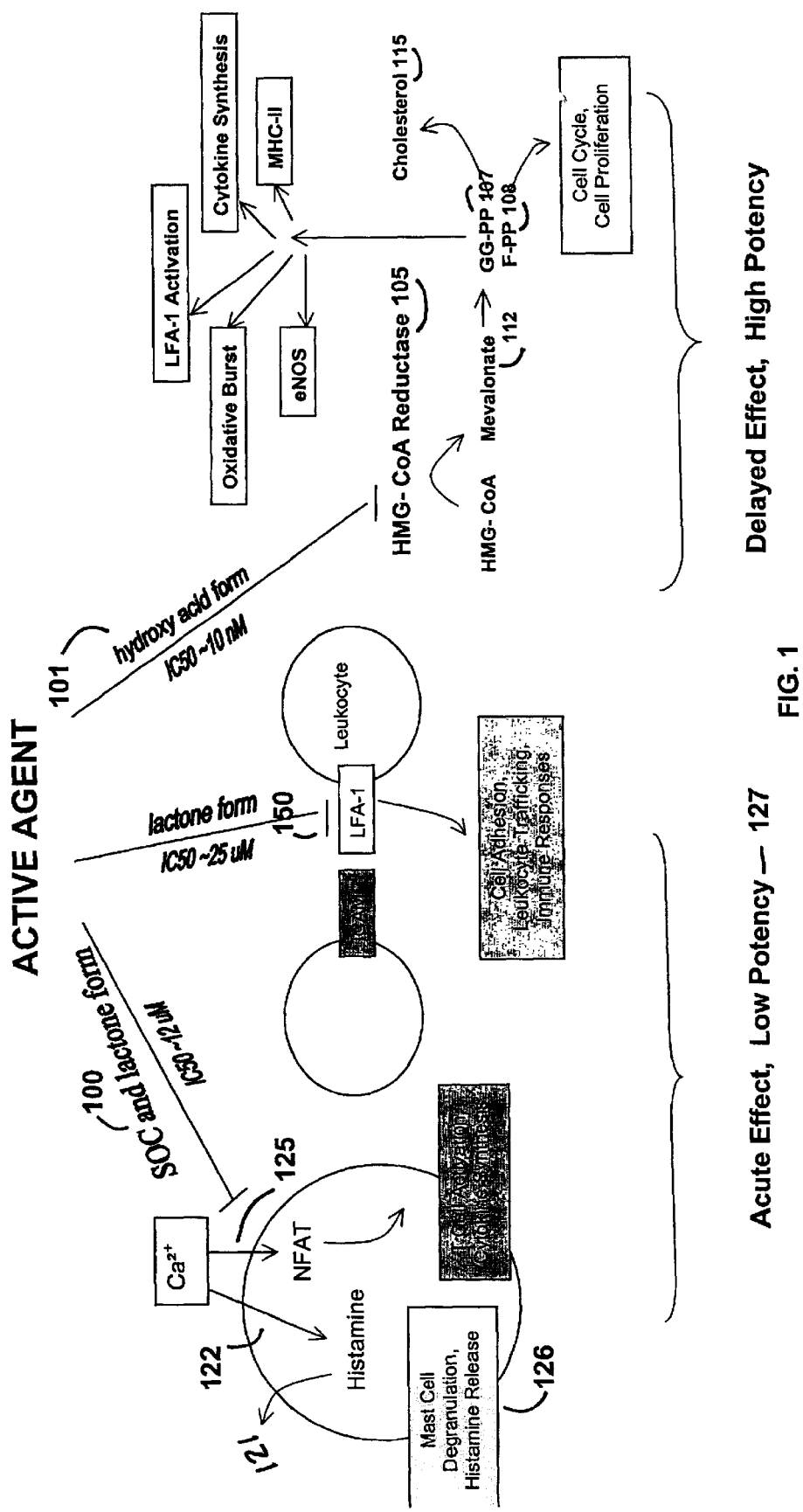
FIG. 1 illustrates a mechanism of action of an embodiment of the present invention.
Figure 2:
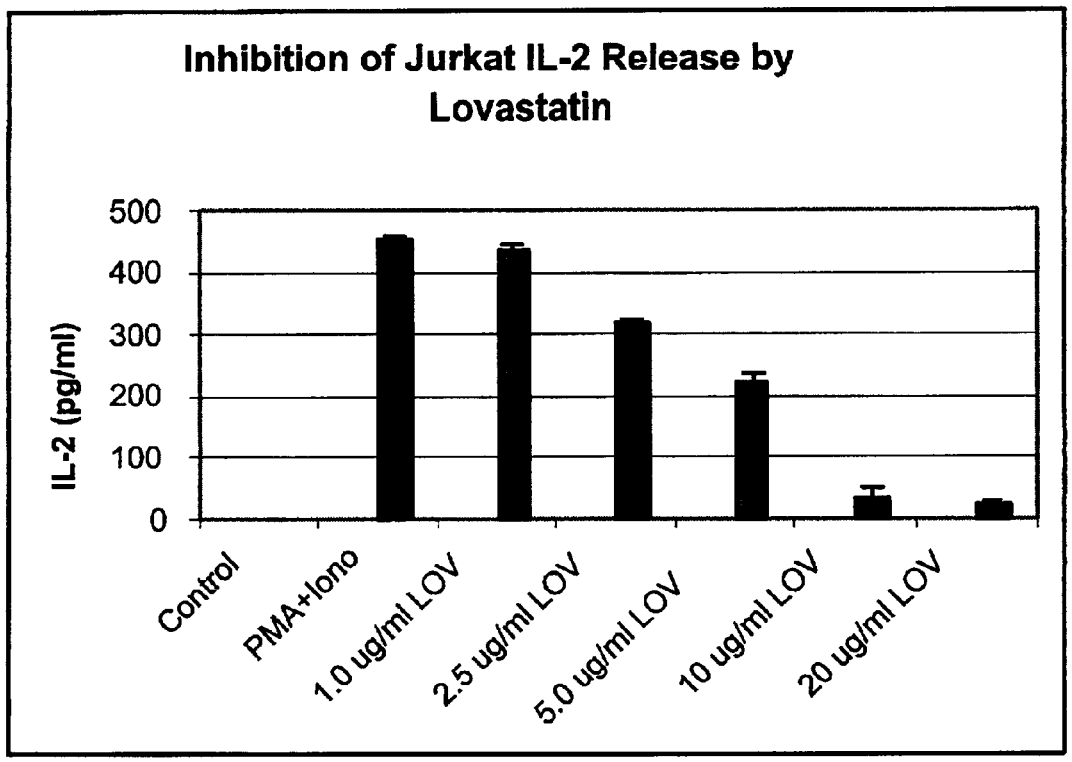
FIG. 2 illustrates the inhibition of Jurkat IL-2 release by lovastatin.
Figure 3:
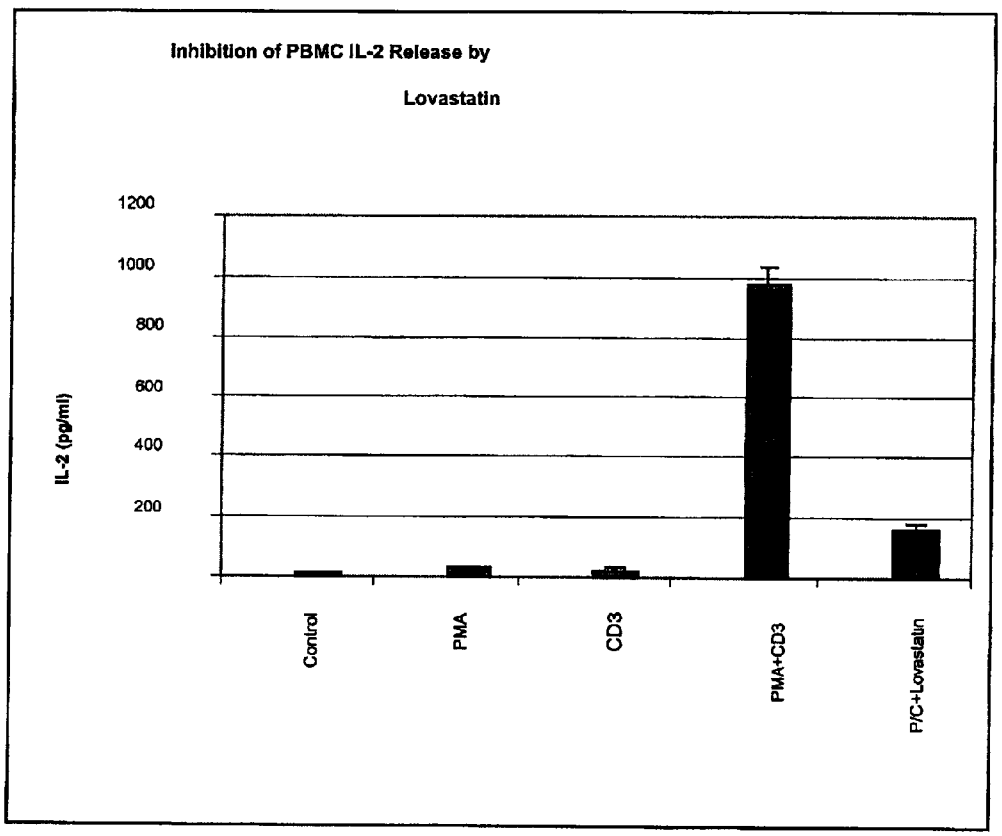
FIG. 3 illustrates the inhibition of PBMC IL-2 release by lovastatin.
Figure 4:
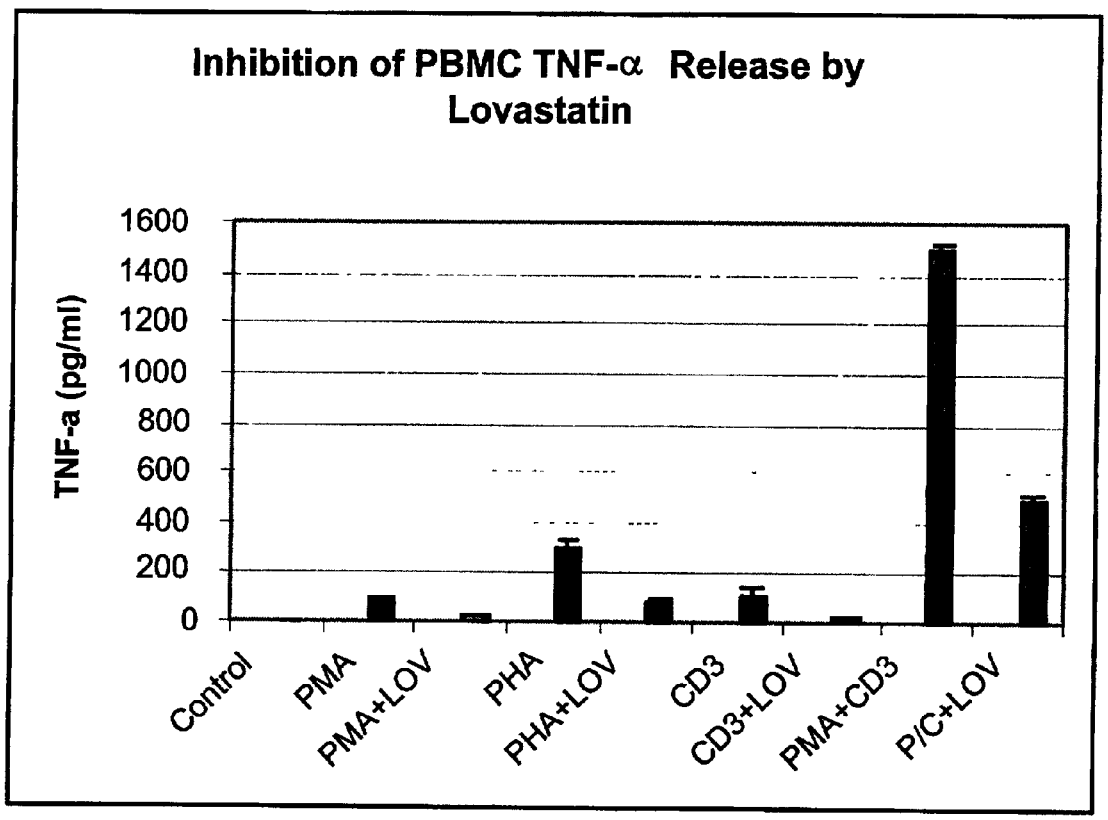
FIG. 4 illustrates the inhibition of PBMC TNF-alpha release by lovastatin.
Figure 5:
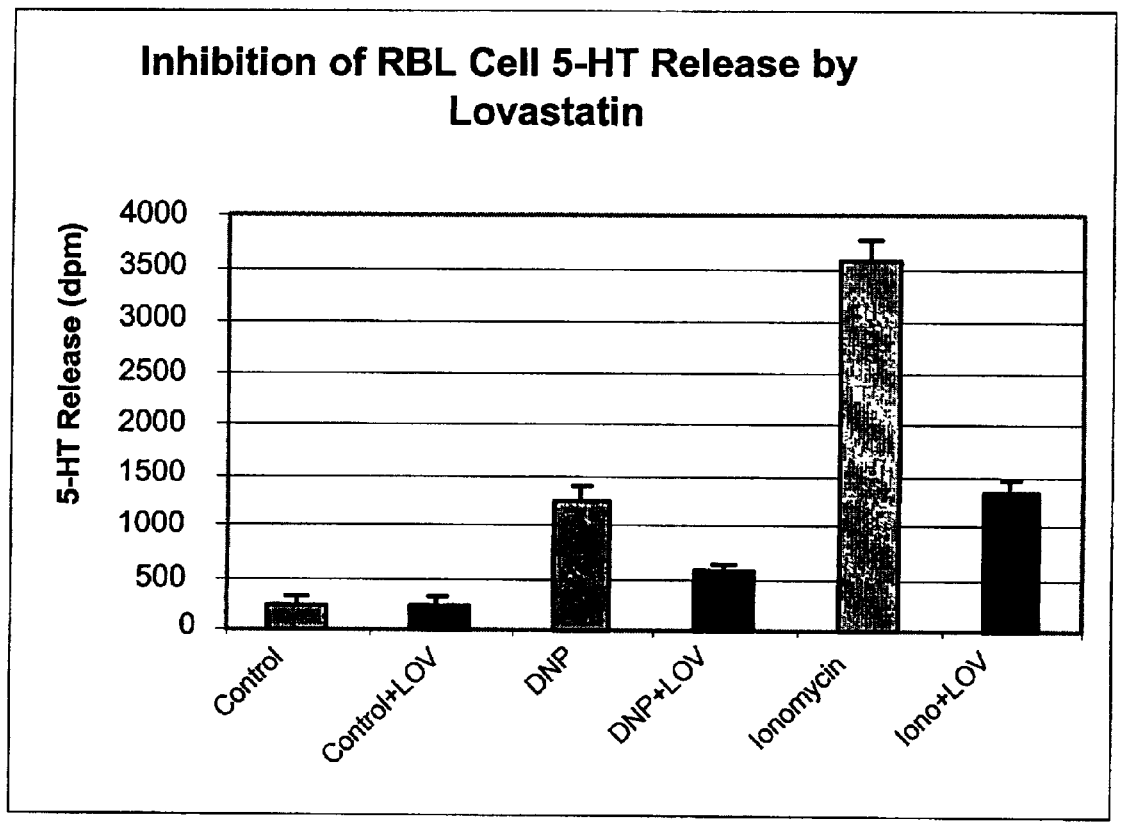
FIG. 5 illustrates the inhibition of rat basophilic leukemia (2H3) cells 5-hydroxytryptomine (5-HT) release by lovastatin.
Figure 6:
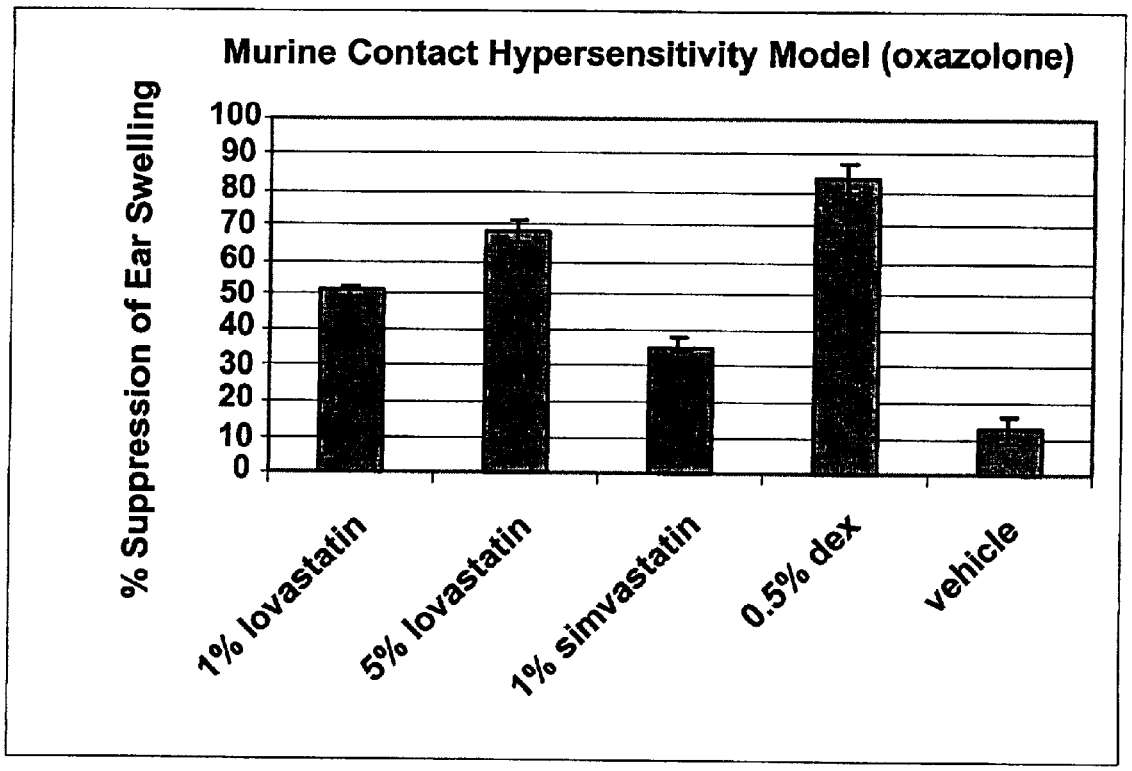
FIG. 6 illustrates the inhibition of oxazolone-induced contact hypersensitivity response in mouse by lovastatin and simvastatin.

The present invention provides compounds and compositions for the treatment of inflammatory disorders. The compounds and compositions are store operated calcium influx inhibitors ("SOC"), which inhibit calcium uptake into a cell. The SOC inhibitors of the present invention preferably inhibit the activation of nuclear factor of activated T cells ("NFAT"), and block calcium dependent T cell activation and mast cell degranulation. Advantageously, the compounds of the present invention can be used to treat various inflammatory disorders and can be formulated in various ways as pharmaceutical compositions for optimal delivery and efficacy.

II. Compounds

The present invention provides compounds structurally related to HMG-CoA reductase inhibitors. The SOC inhibitors of the present invention preferably inhibits the activation of nuclear factor of activated T cells ("NFAT"), and block calcium dependent T-cell activation and mast cell degranulation. Such compounds can be used individually or in combination with other members of this class of compounds, or other therapeutic agents, for treating inflammatory diseases and reactions.

Compounds of the present invention fall within five generic formulae: Formulae I–V. Compounds of Formula I, have four subgeneric formulae: Formulae Ia, IIb, IIc and Id; compounds of Formula II have two subgeneric formulae: Formulae IIa and IIb; and compounds of Formula III have three subgeneric formulae: Formulae IIIa, IIb and IIIc.

In one aspect, the present invention provides compounds of Formula I:

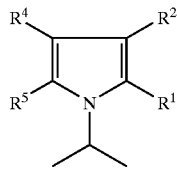

I wherein $R^1$, $R^2$, $R^4$ and $R^5$ have previously been described. Compounds of Formula I have four subgeneric formulae: Formulae Ia, IIb, IIc and Id. These subgenera are set forth below:

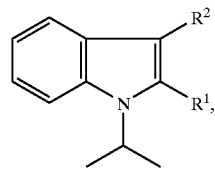

Ia

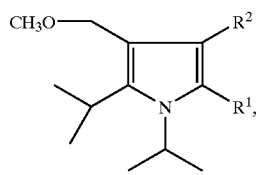

Ib

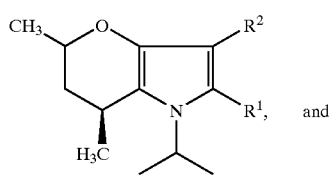

Ic and

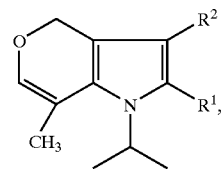

Id

In another aspect, the present invention provides compounds of Formula II:

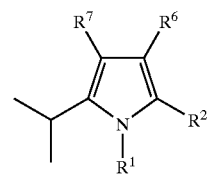

II wherein $R^1$, $R^2$, $R^6$ and $R^7$ have previously been defined. Compounds of Formula II have two subgeneric formulae: Formulae IIa and IIb. These subgenera are set forth below:

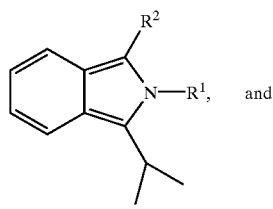

IIa and

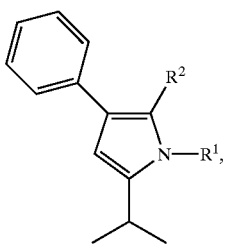

IIb

In yet another aspect, the present invention provides compounds of Formula III:

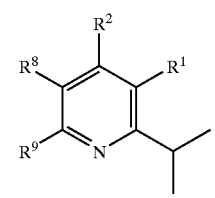

III wherein $R^1$, $R^2$, $R^8$ and $R^9$ have previously been defined. Compounds of Formula III have three subgeneric formulae: Formulae IIIa, IIIb, and IIIc. These subgenera are set forth below:

IIIa

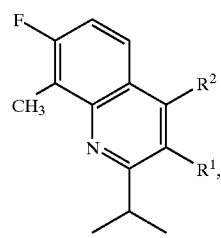

IIIb

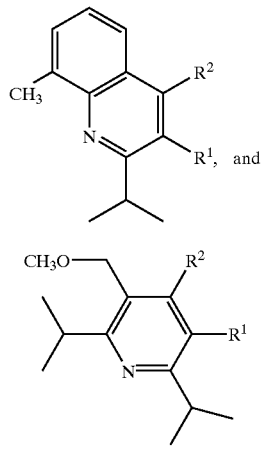

IIIc

In yet another aspect, the present invention provides compounds of Formula IV:

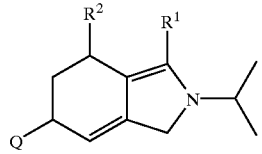

IV wherein $R^1$, $R^2$ and Q have previously been defined.

In still yet another aspect, the present invention provides compounds of Formula V:

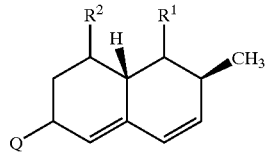

V wherein $R^1$, $R^2$ and Q have previously been defined.

Compounds of the present invention having Formulae I–V, and the subgeneric formulae thereof, are substituted by substituents $R^1$ and $R^2$. Substituent $R^1$ can be further substituted by $R^3$. Preferred substituents $R^1$, $R^2$ and $R^3$ are set forth in Table I.

TABLE I

| | $R^1$ | $R^2$ | $R^3$ |
|---|---|---|---|
| 1 | (4-methyl-oxazol-2-ylthio)ethyl-$R^3$ | 5-pyridyl-HALOGE | —SO$_2$OCH$_3$ |
| 2 | (6-methyl-pyridin-2-ylthio)ethyl-$R^3$ | 5-(6-methyl)pyridyl | —P(=O)(OCH$_3$)$_2$ |
| 3 | (5-methyl-pyrazin-2-yl)CH$_2$OCH$_2$-$R^3$ | 4-phenyl-CH | —C(=O)N(CH$_3$)$_2$ |
| 4 | (5-methyl-1,3-oxazin-2-yl)CH$_2$OCH$_2$-$R^3$ | 4-(NHCOCH)phenyl | —C(=O)N(OCH$_3$)(CH$_3$) |
| 5 | (6-methyl-2H-1,4-oxazin-4-yl)CH$_2$SO$_2$CH$_2$-$R^3$ | CH=N—O—C(=O)N(CH)(CH) | —C(=O)SCH$_3$ |

TABLE I-continued

| | R¹ | R² | R³ |
|---|---|---|---|
| 6 | 1,1'-bipyrrole (tetrafluoro), R and R³ substituents | 2,3-difluoro-5-methylthiophene | —NHC(O)CF₃ |
| 7 | 4-methyl-oxazoline =N—O—CH₂—R³ | 2,4-dimethylthiazole | $\mathrm{-C(CH_3)=N-NHCOCH_3}$ with OCH₃ |
| 8 | CH₃O, OCH₃ substituted alkene chain –R³ | 5-methyl-2-chlorofuran | $\mathrm{-C(CH_3)(NHNHC(O)SCH_3)(NHCOCH_3)}$ |
| 9 | bis-dihydrofuran with CH₃ groups, —R³ | 2-methyl-4-chlorothiazole | —NHSO₂CF₃ |
| 10 | dihydrofuran-methyl / difluorothiophene-R³ | 2-methyloxazole-HALOGE | $\mathrm{-N(C(O)NHCH_3)-O-C(O)NHCH_3}$ |
| 11 | dihydrofuran-methyl / difluorothiophene-R³ | methyl 2-methylbutanoate (CH₃ stereocenter) | —NHOC(O)CH₃ |
| 12 | 5-methyl-1H-pyrrole-2-CH=N—O—R³ | 4-fluorophenyl | —NHSO₂NHCH₃ |
| 13 | 2-methylthiazole-4-CH=NO—R³ | 4-chlorophenyl | —C(O)OCH₃ |
| 14 | 5-methylfuran-2-CH=N—O—R³ | 2-fluoro-5-methylpyridine | —C(O)OH |

TABLE I-continued

| | R¹ | R² | R³ |
|---|---|---|---|
| 15 | (5-R-thien-3-yl)cyclopropyl with H, H, R³ stereochemistry | methyl 2-methyl-3-oxo... CH₃CH(C(=O)OCH₃)—CH | —CH₃ |
| 16 | (5-methylthien-2-yl)cyclopropyl with H, H, R³ | | —CH₂CH₃ |
| 17 | (5-methylthiazol-2-yl)cyclopropyl with H, H, R³ | | |
| 18 | 2,2-dimethylcyclopropyl-substituted thiazoline with R³ | | |
| 19 | CH=N—O—(5-R₃-thien-3-yl) | | |
| 20 | —(CH=CH)₃—R³ | | |
| 21 | —(CH=CH)₂—(CH₂)ₓ—R³ wherein x is about 1 to about 14 | | |

Preferred compounds of the invention are set forth in Table II:

TABLE II

| Compound | Formula | R₁ | R₂ | R₃ |
|---|---|---|---|---|
| 1. | Ia | 20 | 12 | 13 |
| 2. | IIb | 20 | 12 | 13 |
| 3. | V | 20 | 11 | 13 |
| 4. | IIIc | 20 | 12 | 13 |
| 5. | V | 20 | 11 | 13 |
| 6. | Ia | 20 | 12 | 14 |
| 7. | Ia | 20 | 12 | 14 |
| 8. | Ia | 20 | 12 | 3 |
| 9. | Ia | 20 | 12 | 1 |
| 10. | Ia | 20 | 12 | 2 |
| 11. | Ia | 20 | 12 | 4 |
| 12. | Ia | 20 | 12 | 5 |
| 13. | Ia | 20 | 12 | 6 |
| 14. | Ia | 20 | 12 | 7 |
| 15. | Ia | 20 | 12 | 8 |
| 16. | Ia | 20 | 12 | 9 |
| 17. | Ia | 20 | 12 | 10 |
| 18. | Ia | 20 | 12 | 11 |
| 19. | Ia | 20 | 12 | 12 |
| 20. | IIa | 20 | 12 | 13 |
| 21. | IV | 20 | 12 | 13 |
| 22. | Ic | 20 | 12 | 13 |
| 23. | Ib | 20 | 12 | 13 |
| 24. | IIIa | 20 | 12 | 13 |
| 25. | IIIb | 20 | 12 | 13 |
| 26. | IIIc | 20 | 12 | 14 |
| 27. | Ia | 20 | 2 | 13 |
| 28. | Ia | 20 | 2 | 14 |
| 29. | Ia | 20 | 3 | 13 |
| 30. | Ia | 20 | 4 | 13 |
| 31. | Ia | 20 | 5 | 13 |
| 32. | Ia | 20 | 6 | 13 |
| 33. | Ia | 20 | 7 | 14 |
| 34. | Ia | 20 | 8 | 13 |
| 35. | Ia | 20 | 9 | 13 |
| 36. | Ia | 20 | 10 | 13 |
| 37. | Ia | 20 | 10 | 14 |
| 38. | Ia | 20 | 11 | 3 |
| 39. | Ia | 20 | 15 | 14 |
| 40. | Ia | 20 | 13 | 13 |
| 41. | Ia | 1 | 12 | 13 |
| 42. | Ia | 2 | 12 | 13 |
| 43. | Ia | 3 | 12 | 13 |
| 44. | Ia | 3 | 12 | 14 |

TABLE II-continued

| Compound | Formula | $R_1$ | $R_2$ | $R_3$ |
|---|---|---|---|---|
| 45. | Ia | 4 | 12 | 13 |
| 46. | Ia | 4 | 12 | 14 |
| 47. | Ia | 5 | 12 | 13 |
| 48. | Ia | 6 | 12 | 13 |
| 49. | Ia | 7 | 12 | 13 |
| 50. | Ia | 8 | 12 | 13 |
| 51. | Ia | 8 | 12 | 14 |
| 52. | Ia | 9 | 12 | 4 |
| 53. | Ia | 10 | 12 | 13 |
| 54. | Ia | 11 | 12 | 13 |
| 55. | Ia | 12 | 12 | 14 |
| 56. | Ia | 12 | 12 | 13 |
| 57. | Ia | 13 | 12 | 13 |
| 58. | Ia | 14 | 12 | 13 |
| 59. | Ia | 15 | 12 | 13 |
| 60. | Ia | 16 | 12 | 13 |
| 61. | Ia | 17 | 12 | 14 |
| 62. | Ia | 18 | 12 | 13 |
| 63. | Ia | 19 | 12 | 14 |
| 64. | Ia | 19 | 12 | 13 |
| 65. | IIa | 20 | 12 | 14 |
| 66. | Id | 20 | 12 | 14 |
| 67. | IIb | 20 | 12 | 14 |
| 68. | IIb | 20 | 14 | 13 |
| 69. | IIb | 20 | 14 | 3 |
| 70. | Ia | 20 | 7 | 13 |
| 71. | Ia | 20 | 8 | 14 |
| 72. | Ia | 20 | 9 | 14 |

As will be apparent to those of skill in the art, in certain preferred aspects, Table I together with Formulae Ia, Ib, Ic, Id, IIa, IIb, IIIa, IIIb, IIIc, IV and V set forth compounds of the present invention. These compounds include, for example, compounds Ia;20;12;13, IIb;20;12;13, V;20;11;13, IIIc;20;12;13, V;20;11;13 and the like, wherein the Roman numeral reflects the generic formula or sub-generic formulae and the 3 numbers which follow reflect the specific $R^1$, $R^2$ and $R^3$ residue in Table I, and where the residue is located in the table. For example, the structures of compounds Ia;20;12;13, IIb;20;12;13, V;20;11;13, IIIc;20;12;13, V;20;11;13 are set forth below.

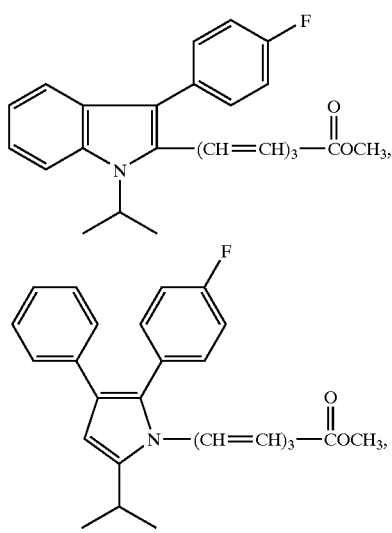

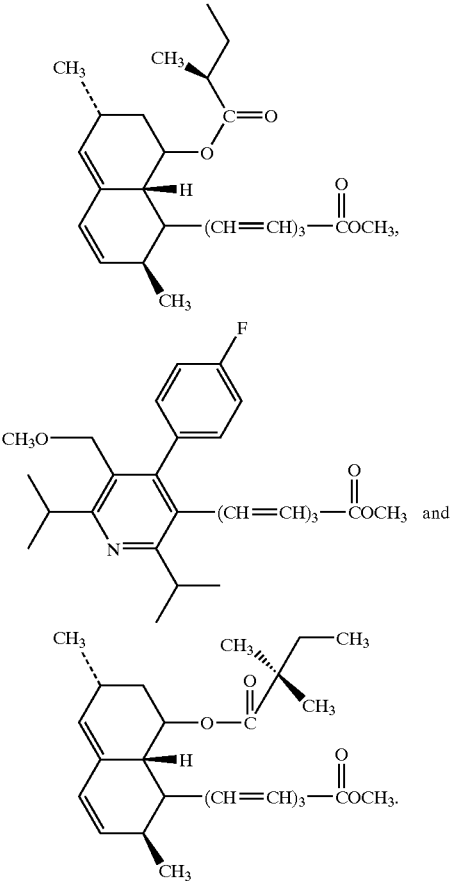

The foregoing compounds are preferred compound of the present invention.

The present compounds are useful for treating inflammatory diseases or reactions, in particular those with overproduction of inflammatory mediators, including, but not limited to, IL-2, IL-5, IL-8, IFN-gamma, and TNF-alpha. Without being limited to any particular theory, it is believed that, in certain embodiments, the compounds are useful for treating any condition arising from, or related to, increased activity of the lymphocyte activation pathway downstream of NFAT (nuclear factor of activated T cells). In certain embodiments the compounds are also useful for treating inflammation arising from other processes, including, but not limited to, mast cell degranulation and leukocyte secretion, as well as calcium-dependent elaboration of proinflammatory adhesion molecules, chemokines and cytokines by a variety of non-hematopoietic cells, including endothelial and epithelial cells.

III. Synthesis

As discussed previously, compounds of the present invention fall within five formulae: Formulae I–V. Compounds of Formula I, have four subgeneric formulae: Formulae Ia, IIb, IIc and Id; compounds of Formula II have two subgeneric formulae: Formulae IIa and IIb; and compounds of Formula III have three subgeneric formulae: Formulae IIIa, IIb and IIIc.

In certain aspects, the compounds of the present invention can be made using commercially available starting materials. In one embodiment, the compounds of Formula Ia use as starting materials, compounds as disclosed in U.S. Pat. No. 4,739,073, which is hereby incorporated by reference in its entirety for all purposes.

In one embodiment, an intermediate aldehyde or alkyl ester as shown below, is used to couple an R[1] functional group to the protected heterocyclic ring in a aldehyde or ester condensation reaction as set forth below:

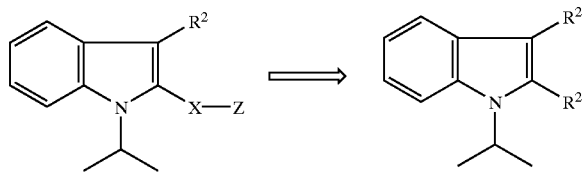

wherein Z is CHO or C(O)CH$_2$CH$_3$, and X is for example, (CH$_2$)$_{0-1}$ or —CH$_2$CH=CH—, CH=CH(OH)—CH$_2$—CH(OH)—CH$_2$—, —CH=CH—, —CH=CH—CH$_2$— and the like. In this reaction, a variety of reaction conditions such as solvents, temperature and reaction times can be employed. Preferably, the reaction is conducted in an alcohol such as ethanol or t-butanol. In certain preferred instances, the aldehyde is coupled to an R[1] functional group using for example a strong base, with subsequent aqueous work-up.

In alternative embodiment, Wittig reagents can be used with appropriate starting materials.

In one illustrative embodiment, not in any way intended to be limiting, the compounds of Formula Ia for example, Ia;20;12;13, can be synthesized from fluvastatin as set forth below in Scheme I:

Scheme I

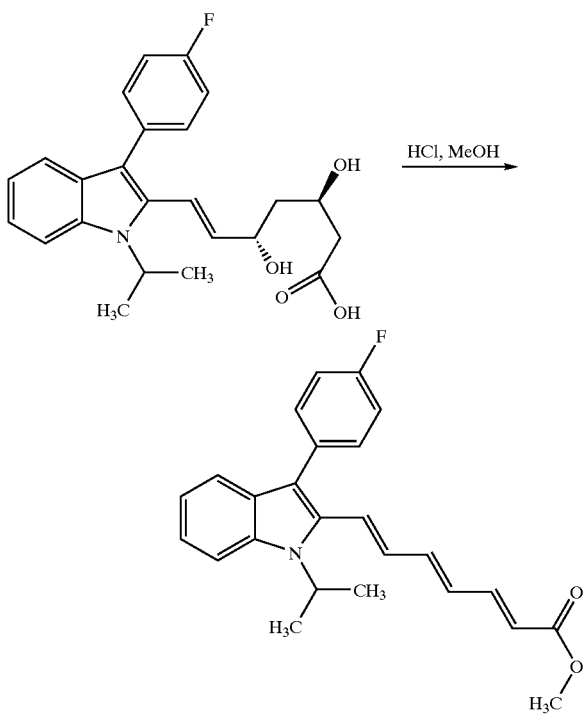

Synthesis of fluvastatin is well known to those of skill in the art (see, Drugs of the Future 16(9):804, 1991). Compounds of Formula I can also be prepared from alternative starting materials via alternative methods. Alternative starting materials include compounds similar to those used for synthesizing fluvastatin, compounds similar to intermediates of fluvastatin synthesis, and compounds similar to fluvastatin.

In certain other aspects, the compounds of the Formulae Ib, Ic and Id use a correspondingly similar intermediate specific for their respective scaffolds.

In other embodiments, the compounds of the Formula II use as their intermediates known compounds from U.S. Pat. No. 5,273,995, which is hereby incorporated by reference its entirety for all purposes.

For example, an intermediate aldehyde or alkyl ester as shown below, is used to couple an R[1] functional group to the protected heterocyclic ring in a aldehyde or ester condensation reaction as set forth below:

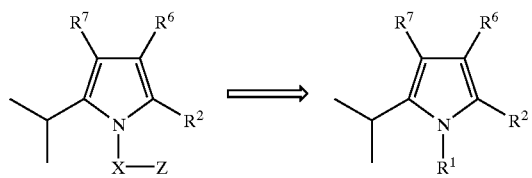

wherein Z is CHO or C(O)CH$_2$CH$_3$, and X is for example, (CH$_2$)$_{0-1}$ or —CH$_2$CH=CH—, CH=CH(OH)—CH$_2$—CH(OH)—CH$_2$—, —CH=CH—, —CH=CH—CH$_2$— and the like.

In certain other aspects, the compounds of the Formula Type III use as their intermediate known compounds of U.S. Pat. No. 5,006,530, which is hereby incorporated by reference in its entirety for all purposes. For example, as set forth therein, using compounds and methods for synthesis for examples 114, 115, 117, 127, apparent modifications to those of skill in the art generates the following synthetic procedure:

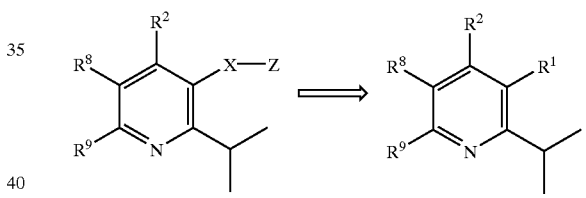

wherein Z is CHO or C(O)CH$_2$CH$_3$, and X is for example, (CH$_2$)$_{0-1}$ or —CH$_2$CH=CH—, CH=CH(OH)—CH$_2$—CH(OH)—CH$_2$—, —CH=CH—, —CH=CH—CH$_2$— and the like. Similarly, the compounds of the Formulae IIIa, IIIb and IIIc are prepared using the methods set forth above by corresponding modifications to Formula II.

The compounds of Formula IV are prepared by similar modifications to those of Formula II as show below:

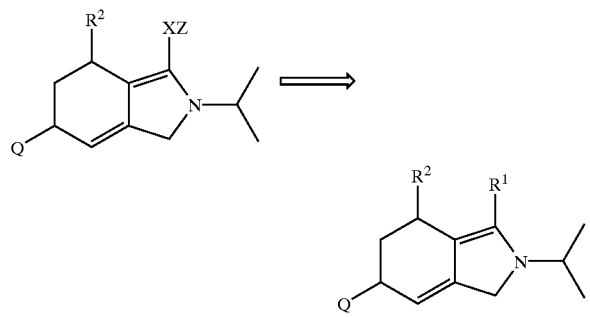

wherein Z is CHO or C(O)CH$_2$CH$_3$, and X is for example, (CH$_2$)$_{0-1}$ or —CH$_2$CH=CH—, CH=CH(OH)—

$CH_2$—$CH(OH)$—$CH_2$—, —$CH$=$CH$—, —$CH$=$CH$—$CH_2$— and the like. Q is —$OCH_3$, —$OH$, —$CH_3$, —$CH_2CH_3$ and the like.

In still other embodiments, compounds of Type V can be prepared from compounds of U.S. Pat. No. 4,346,227, which is incorporated herein by reference for all purposes.

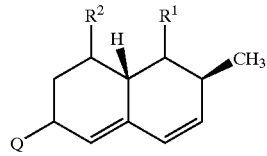

wherein Q is —$OCH_3$, —$OH$, —$CH_3$, —$CH_2CH_3$ and the like.

Specific compounds of the present invention can be prepared by a variety of methods known to those of skill in the art. Reaction conditions, solvents, and starting materials can be used in a variety of ways to optimize yields. Compounds 1–40 and 65–72 can be prepared using the foregoing methods, starting for example, from the corresponding diol.

In still other embodiments, compounds of the present invention can be prepared from the modifications of intermediates by a variety of means. For example, the XZ group can be replaced by groups such as halogen, hydroxyl, amino, hydrogen or metallic derivatives such as sodium, magnesium, or lithium, and these derivatives are further reacted to give products.

Those of skill in the art will readily recognize that the present compounds can exist in a number of cis and trans isomers, E/Z forms, diastereomers, as well as optical isomers. The compounds of the present invention include all such combinations and variations.

IV. Biological Activity

A. Store Operated Calcium Influx Inhibition

The novel mechanism of SOC inhibition 100 of the present invention is set forth in FIG. 1. This illustration is merely an example and is not intended to be limiting. Those of skill in the art will recognize alternatives, modifications and variations. As shown therein, statins in the open-chain form 101 are inhibitors of the enzyme 3-hydroxy-3-methylglutaryl coenzyme A (HMG-CoA) reductase 105. The high-potency delayed effects of the HMG-CoA reductase mechanism 103 is characterized in that HMG-CoA reductase 105 is the rate-limiting step in the biosynthesis of mevalonate 112, the precursor of cholesterol 115 synthesis and a variety of non-sterol isoprenoid products such as geranylgeranyl pyrophosphate 107 and farnesyl pyrophosphate 108. Rho proteins require geranylgeranyl pyrophosphate to function. Rho has been implicated in endothelial nitric oxide synthase (eNOS) suppression, lymphocyte function-associated antigen-1 (LFA-1) activation, major histocompatibility complex class II (MHC-II) induction, cytokine production, cell cycle progression, cell proliferation. Statins have been shown to reduce the risk of cardiovascular mortality and morbidity, and have become the most commonly used drugs for the treatment of hypercholesterolemia and arteriosclerosis. In contrast, the SOC inhibitor mechanism 100 of the present invention acts by blocking calcium influx 122, which in turn, blocks calcium dependent T cell activation 125 and mast cell degranulation 126. Histamine release 121 is also inhibited. As this pathway 100 depends on higher concentrations of active 127 (low potency) compared to the HMG-CoA reductase mechanism 101, the therapeutic utility of the SOC inhibitors is preferably achieved using high local concentrations for immediate effect 127. The SOC inhibitors of the present invention inhibit calcium influx into cells, thereby inhibiting calcium dependent activation.

Moreover, the SOC inhibitors of the present invention inhibit the activation of NFAT. NFAT is known to be activated by calcineurin. By acting upstream of calcineurin to inhibit calcium availability 125, SOC inhibitors inhibit NFAT activation, thereby turning off T cell activation.

Evidence that the SOC inhibitors of the present invention block calcium influx was obtained using Jurkat cells loaded with the fluorescent $Ca^{2+}$ indicator Fura-2. A rapid and sustained increase in intracellular calcium concentration was observed when Fura-2-loaded Jurkat cells were stimulated with ionomycin, thapsigargin, or cyclopriazonic acid. The calcium signal is dependent on depletion of intracellular calcium stores and the presence of extracellular calcium, and is strongly inhibited by $Ni^{2+}$ and $La^{3+}$, hallmarks of store-operated calcium influx. SOC inhibitors (e.g., δ-lactone) reduced the intracellular $Ca^{2+}$ signal induced by ionomycin or thapsigargin in a dose-dependent manner with an $IC_{50}$ near 10 μM.

HMG-CoA reductase 105 is inhibited by the open chain form (dihydroxycarboxylic acid) of statins 101. The δ-lactone-containing statins, i.e., lovastatin, mevastatin, and simvastatin, are inactive as HMG-CoA reductase inhibitors until converted to their respective open chain forms, hence their designation as prodrugs. The lactone-containing statins, lovastatin, mevastatin, and simvastatin, were able to inhibit NFAT activity using the SOC inhibitor mechanism 100. Pravastatin, fluvastatin, and atorvastatin, which are open-chain statins, were inactive. When comparing the lactone and open chain forms of mevastatin, only the lactone form was active. Further, fluvastatin acquired NFAT inhibitory activity, albeit less potent than lovastatin, when converted to its corresponding δ-lactone.

Moreover, lovastatin has been shown to bind to the LFA-1 I-domain 150 at a site distant from the metal ion-dependent adhesion site, causing a conformation change that indirectly prevents the binding of LFA to ICAM-1. Since the antagonism of LFA-dependent cell adhesion and inhibition of calcium influx by SOC inhibitors share similar potencies and structure activity relationships, whether LFA-1 I-domain binding and calcium entry are linked was investigated. Several classes of compounds have been developed that bind with high affinity to the lovastatin-binding site of the I-domain. Several hydantoin derivatives, BIRT377 and its less active enantiomer, and tested in the NFAT reporter assay. The compounds exhibited very weak NFAT inhibitory activity as compared to their LFA-1 effects. In addition, there was no difference in activity between BIRT377 and its inactive enantiomer. As such, it is believed that SOC inhibition by lovastain is not mediated through LFA-1 binding in Jurkat cells.

Calcium influx in non-excitable cells regulates such diverse processes as exocytosis, contraction, enzyme control, gene regulation, cell proliferation and apotosis. Elevation of intracellular free $Ca^{2+}$ is one of the key triggering signals for T-cell activation by antigen. Following engagement of the T-cell receptor, intracellular channels ($IP_3$ and ryandone receptors) release $Ca^{2+}$ from intracellular stores, and by depleting the stores trigger prolonged $Ca^{2+}$ influx through store operated $Ca^{2+}$ channel in the plasma membrane. Store operated $Ca^{2+}$ entry plays a key role in replenishing calcium stores and activating various physiological processes, including for example signaling cascade initiated by calcineurin, nuclear factor of activated T cells (NFAT), nuclear factor kB (NF-kB), the stress kinases c-Jun N-terminal kinase (JNK) and AP-1.

B. Anti-inflammatory Actions of Statins

As discussed above, δ-lactone-containing statins are useful in the present invention. Such stains include for example, mevastatin (also referred to as compactin or ML-236B), lovastatin (also referred to as MK-803, Mevinolin, or Mevacor® (commercially available from Merck & Co., West Point, Pa.), simvastatin (also referred to as MK-733, Synvinolin, or Zocor®, commercially available from Merck & Co., West Point, Pa.), fluvastatin (also referred to as Fluindostatin or Lescol® (commercially available from Novartis Pharmaceuticals, East Hanover, N.J.)), pravastatin (also referred to as Pravachol®, commercially available from Bristol-Meyers Squibb Company, Princeton, N.J.), dalvastatin (also referred to as RG 12561), cerivastatin, rosuvastain (Crestor-AstraZeneca) and atorvastatin (also referred to as Lipitor®, commercially available from Pfizer Inc., New York, N.Y.), as well as derivatives and salts thereof.

Statins potently inhibit the enzyme HMG-CoA reductase that catalyzes the conversion of 3-hydroxy-3-methylglutaryl coenzyme A (HMG-CoA) to mevalonate, a key intermediate in the biosynthesis of cholesterol and other non-sterol isoprenoid products. HMG-CoA reductase is specifically inhibited by the open β-hydroxy form of lovastatin. The antiproliferative and anti-inflammatory effects of HMG-CoA reductase inhibitors are mediated by suppression of the isoprenoids farnesyl pyrophosphate (F-PP) and geranylgeranyl pyrophosphate (GG-PP), used in the post-translational modification of signaling proteins, e.g., small GTPases of the Ras and Rho families. Rho geranylgeranylation plays roles in T cell proliferation, eNOS regulation, LFA-1 activation, the oxidative burst, chemotaxis, cytokine synthesis, and IFNγ-induced MHC class II expression. The effects of HMG-CoA reductase inhibitors on these processes are somewhat delayed since depletion of the isoprenoid pools occurs over a period of hours.

Lovastatin δ-lactone binds to the I-domain of the leukocyte $β_2$-integrin LFA-1, and through an allosteric mechanism, prevents LFA-1 from binding to its primary counter receptor ICAM-1. LFA-1 plays important roles in cell-cell adhesion and communication, particularly in leukocyte trafficking to sites of inflammation and immune responses. Lovastatin binds to LFA-1 rapidly, but with lower affinity than to HMG-CoA reductase.

The third distinct mechanism of lovastatin action is inhibition of store-operated calcium influx in a variety of non-excitable cell types, including lymphocytes and granulocytes. This effect is mediated by the lovastatin δ-lactone, does not require any pre-incubation, and requires higher concentrations of drug as compared to inhibition of HMG-CoA reductase. Antigen-stimulated T cell activation and mast cell degranulation, for example, are calcium-dependent processes. By blocking calcium entry in T cells, lovastatin prevents activation of the transcription factor NFAT and its target genes, including IL-2, IL-4, IL-5, TNF, and IFNγ, thereby suppressing Th1- and Th2-type immune responses. The inhibition of mast cell degranulation by lovastatin prevents the release of preformed mediators of inflammation, including histamine, IL-3, IL-5, and TNF. In addition, lovastatin also inhibits the calcium-dependent de novo synthesis of proinflammatory leukotrienes and cytokines by mast cells. Calcium-dependent degranulation and mediator synthesis is also inhibited in other inflammatory cells, such as eosinophils, neutrophils, NK cells, and B cells.

C. Assays

A SOC inhibition assay can be used to determine whether a test compound is a SOC inhibitor. In this assay, Jurkat cells are washed with PBS and Loading Buffer. Cells are resuspended in Loading Buffer and loaded with 1 μM of the $Ca^{2+}$-sensitive dye, Fura-2AM (Molecular Probes, Inc.). Loaded cells are then washed with the loading buffer and incubated with thapsigargin and EGTA to deplete intracellular calcium storage pools. Cells are washed and resuspended in calcium-free Loading buffer. Calcium influx analyses are then performed using a luminescence spectrometer. Using alternating excitation wavelengths of 340 and 380 nm, and an emission wavelength of 510 nm, the intracellular free $Ca^{2+}$ concentration is calculated from the 340/380 nm fluorescence ratio (Grynkiewicz et al., 1985). Test compound can then be added to the cells and incubated 10 min, and calcium influx initiated by the addition of $CaCl_2$ to a final concentration of 5 mM. See Example 14.

Animal models that are widely viewed to reflect inflammatory or immune responses and to have predictive value in assessing the efficacy of various treatments for these disorders can be utilized to evaluate the therapeutic efficacy of compounds described herein.

For example, the effects on the immune response of a compound of interest or of a combination of compounds can be tested in vitro by evaluating murine thymic T cell proliferation and IL-2 production or gene expression. Methods to measure T cell proliferation and IL-2 production are standard and well known to those of skill in the art. Exemplary animal models for estimating the effects of the compounds of the present invention include, but are not limited to, the mouse acute irritant model, the allergic contact hypersensitivity model and the like. Other suitable models include, for example, the inbred strain of NC/Nga mice, which when reared under non-pathogen-free conditions, develops chronic relapsing skin inflammation. Injection of Balb/c mice with *Shistosoma japonica* glutathione-S-transferase leads to the development in the injected mice of a systemic dermatitis, providing a useful model of allergic dermatitis. Additional models for skin allergies can be obtained by applying to the ears of mice 2,4-dinitrofluorobenzene or oxazolone, which induces an allergic cutaneous response in the mice (see, Nagai et al. *J. Pharmacol. Exp. Therapeutics* 288:43–50). Other suitable models for testing the effects of the compounds of the present invention on atopic dermatitis include, but are not limited to, the repetitive epicutaneous sensitization of mice with the antigen ovalbumin.

In the case of inflammatory bowel disease models, dextran sulfate sodium (DSS), trinitrobenzene sulfonic acid (TNBS), and oxazolone-induced colitis have been used routinely as screening tools. Spontaneous colitis has also been observed in a few naturally occurring mutant strains. Several gene-knockout and transgenic strains also develop colitis. These models have been reviewed by Boismenu et al. in *J Leukoc. Biol.*, 67:267–278, 2000; and Blumberg R et al. in *Current Opinion in Immunology*, 11:648-656, 1999.

As for osteoporosis, various ovarectomized models have been used to evaluate potential therapies (see, Lill C A et al., *J Orthop Trauma* 14(8):559–65, 2000; Chavassieux P, et al. *J Bone Miner Res* 16(1):89–96, 2001). For example, six-month-old rats were ovarectomized and left untreated for 2 months to allow the development of osteopenia (see, Bouali Y, et al., *Gynecol Endocrinol* 15(1):48–55, 2001). Treatment alone or in combination with estradiol, was started and continued for 2 months. Bone was assessed by a combination of static and dynamic histomorphometric measurements, by densitometry and by the use of biochemical markers of bone turnover. Similarly, ovarectomized monkeys responded to parathyroid hormone (PTH) therapy following a long-term treatment regimen with this peptide (see, Jerome C P, et al. *Bone* Feb;28(2):150–9, 2001). Alternatively, carrageenan arthritis is associated with high-turnover bone loss (see, Moran E L et al., *Orthop Res* 2000 Nov;18(6):873–81); which also appeared to respond to bisphophonate, a proven medical treatment for osteoporosis. Another similar model, i.e., collagen-induced arthritis (see, Enokida M, et al. Bone 28(1):87–93, 2001) has also been used for studying inflammation induced osteoporosis (see, Goldring S. et al., *Arthritis Res* 2(1):33–7, 2000; Jones S M et al., *Clin Exp Rheumatol* 11(5):557–62, 1993).

V. Inflammatory Disorders

The compounds, compositions and methods of the invention are useful for treating inflammatory diseases or reactions, in particular those with overproduction of inflammatory mediators, including, but not limited to, IL-2, IL-5, IL-8, IFN-gamma, and TNF-alpha. Store-operated calcium influx activates a number signaling pathways in inflammatory cells, resulting in the production of proinflammatory cytokines and chemokines, release of other soluble inflammatory mediators such as autocoids, proteolytic enzymes, and toxic proteins, and upregulation of cell surface molecules, including adhesion molecules and receptors, that play key roles in inflammatory and autoimmune diseases. Important calcium-regulated signaling molecules include the transcription factors NFAT and NF-κB, and the stress kinases JNK and p38. JNK plays an important role in upregulation of the transcription factor activator protein-1 (AP-1), and is involved in TNF-α production (Minden A and Karin M, Biochim. Biophys. Acta 1333:F85–104, 1997; Lee J C and Young P R, J. Leukoc. Biol. 59:152–7, 1996). In activated T cells, NFAT is required for the transcriptional regulation of IL-2, IL-3, IL-4, IL-5, IL-8, IL-13, TNF alpha, and GM-CSF (Crabtree G R and Clipstone N A, Annu. Rev. Biochem. 63:1045–83, 1994). NF-kappa B is essential for the transcriptional regulation of the proinflammatory cytokines, including IL-1, IL-6, IL-8, IFNγ and TNF-α, as well as cell adhesion molecules VCAM-1 and ICAM-1, the IL-2 receptor alpha chain, and the cell growth regulator c-Myc (Baldwin A S, J. Clin. Invest. 107:3–6, 2001; Barnes P J and Karin M, N. Engl. J. Med. 336:1066–71, 1997). AP-1 transcriptionally regulates IL-2 and production of matrix metalloproteinases (Palanki M S, Curr. Med. Chem. 9:219–27, 2002). Mast cells and basophils express the high affinity IgE receptor (FcεRI) and synthesize histamine. Cross-linking FcεRI by antigen results in calcium influx, degranulation, and production of proinflammatory eicosanoids. In addition to histamine, human mast cell secretory granules also contain the neutral proteases tryptase, chymase and carboxypeptidase. Tryptase has been implicated as a fibrogenic factor. Mast cells and basophils thus participate not only in allergic disease, but also in chronic and fibrotic disorders affecting several organs, including the lungs (Marone G, Int. Arch. Allergy Imnunol. 114:207–17, 1997). Compounds that can effectively block calcium-influx and activation of NFAT, NF-κB, AP-1, and mast cell/basophil degranulation thus provide potential medical treatments for various inflammatory and autoimmune disorders.

Transcription factors such as NF-κB are activated by extracellular signals or cell-to-cell interactions that are converted into intracellular activation signals through receptor molecules located in the cell membrane. It has been proposed that bacterial toxin such as endotoxin, induces calcium fluxes in monocytes and the nuclear translocation of NF-κB, a key step in the generation of the inflammatory response. Under acute condition, endotoxin-induced inflammatory process could lead to serious medical condition like sepsis. The number of known genes being transcribed after NF-κB activation is increasing steadily. These genes includes cytokines (such as IL-1, TNF-α, etc.), chemokines (IL-8 for example), growth factors, cellular ligands, and adhesion molecules; many of these genes are involved in the pathogenesis of rheumatoid arthritis (RA). To date, many other inflammatory disorders are believed to relate to NF-κB action (for recent reviews, see Yamamoto Y and Gaynor R B, Curr. Mol. Med. 1(3):287–96, 2001; Baldwin A S, J. Clin. Invest. 107:3–6, 2001). For example, Pneumococci cause damage to the ear in otitis and in association with bacterial meningitis. The pathogenesis of injury involves host responses to the cell wall and pneumolysin. Release of cell wall components, particularly during antibiotic-induced bacterial lysis, leads to an influx of leukocytes and subsequent tissue injury. The signal transduction cascade for this response is becoming defined and includes CD14, Toll-like receptors, NF-κB, and cytokine production. Decreasing the sequelae of otitis can be achieved by an effective blockage of pneumococcal-induced inflammation. We have demonstrated that SOC inhibitors are effective in blocking NF-κB activation in Jurkat cells, and thus can be considered as potential medical treatments of inflammatory conditions, such as RA and Crohn's disease, where NF-κB activation plays a crucial role.

The nuclear factor of activated T cells (NFAT) proteins are a family of transcription factors whose activation is controlled by calcineurin, a calcium-dependent protein phosphatase (Rao A et al., Annu. Rev. Immunol. 15:707–47, 1997; Stankunas K et al., Cold Spring Harb. Symp. Quant. Biol. 64:505–16, 1999). Originally identified in T cells as inducers of cytokine gene expression, NFAT proteins play varied roles in cells outside of the immune system (Horsley V and Pavlath G K, J. Cell Biol. 156:771–4, 2002; Graef I A et al., Curr. Opin. Genet. Dev. 11:505–12, 2001). Recently, using immunofluorescence/confocal microscopy, cyclosporin A and tacrolimus were shown to block the nuclear translocation of calcineurin and NFAT in cultured keratinocytes (Al-Daraji W I et al., J. Invest. Dermatol. 118:779–88, 2002). The results showed that a variety of cell types in normal and psoriatic skin expressed calcineurin and NFAT1, but expression was particularly prominent in keratinocytes. The principal cyclosporin A and tacrolimus binding proteins cyclophilin A and FKBP12 were also expressed in keratinocytes and nonimmune cells in skin. NFAT1 was predominantly nuclear in normal basal epidermal keratinocytes. Increased nuclear localization of NFAT1 was observed in suprabasal keratinocytes within lesional and to a lesser extent nonlesional psoriatic epidermis compared to normal skin, suggesting increased activation of calcineurin in psoriatic epidermal keratinocytes. Agonists that induce keratinocyte differentiation, specifically 12-0-tetradecanoyl-phorbol-13-acetate (TPA) plus ionomycin, raised intracellular calcium, induced nuclear translocation of NFAT1 and calcineurin in keratinocytes, and was inhibited by pretreatment with cyclosporin A or tacrolimus. In contrast, in human dermal fibroblasts, TPA plus ionomycin or TPA did not significantly alter the proportion of nuclear-associated NFAT1. These results indicate that calcineurin is functionally active in human keratinocytes by inducing nuclear translocation of NFAT1, and that regulation of NFAT1 nuclear translocation in skin is cell type specific. Inhibition of this pathway in epidermal keratinocytes may account, in part, for the therapeutic effect of cyclosporin A and tacrolimus in skin diseases such as psoriasis. SOC inhibitors which can effectively inhibit NFAT activation provide an alternative pharmacological treatment for inflammatory conditions such as psoriasis.

Mast cells and/or basophils have been implicated in the expression of a wide variety of biological responses, including immediate hypersensitivity reactions, host responses to parasites and neoplasms, angiogenesis, tissue remodeling, and immunologically non-specific inflammatory and fibrotic conditions. Recent findings suggest that an important mechanism by which mast cells influence such biological responses is through the production of a broad panel of multifunctional cytokines. In contrast, the extent to which basophils can produce cytokines is uncertain (Galli S J et al., Curr. Opin. Immunol. 3:865–72, 1991). Mast cell-associated mediators are generally classified into two groups: the preformed mediators, which are stored in the cells' cytoplasmic granules and are released upon exocytosis, and the newly synthesized mediators, which are not stored but are produced and secreted only after appropriate stimulation of the cell. We now report that tumor necrosis factor alpha (TNF-alpha)/cachectin represents a new type of mast cell-associated mediator, in that IgE-dependent mast cell activation results in the rapid release of preformed stores of the cytokine followed by the synthesis and sustained release of large quantities of newly formed TNF-alpha. We also demonstrate that challenge with specific antigen induces higher levels of TNF-alpha mRNA at skin sites sensitized with IgE in normal mice or mast cell-reconstituted genetically mast cell-deficient WBB6F1-W/W1' mice than at identically treated sites in WBB6F1-W/W1' mice that are devoid of mast cells. These findings identify mast cells as a biologically significant source of TNF-alpha/cachectin during IgE-dependent responses and define a mechanism whereby stimulation of mast cells via the FC epsilon $R^1$ can account for both the rapid and sustained release of this cytokine (Gordon J R and Galli S J, J. Exp. Med. 174:103–7, 1991).

Mast cells are widely regarded as important effector cells in immune responses associated with Th2 cells and IgE. Recent work shows that they can also contribute significantly to the expression of innate immunity. Furthermore, survival in a model of acute bacterial infection that is dependent on complement and mast cells can be greatly enhanced by long-term treatment of mice with the kit ligand (stem cell factor) at least in part because of the effects of such treatment on mast cell numbers and/or function. These findings not only indicate that mast cells can represent a critical component of host defense in natural immunity but also suggest that mast cell function in this setting can be manipulated for therapeutic ends (Galli S J et al., Curr. Opin. Immunol. 11:53–9, 1999). The release of pro-inflammatory mediators by mast cell degranulation is considered a calcium-dependent process. Compounds, such as SOC inhibitors that prevent mast cell degranulation, represent novel potential medical treatments for inflammatory, allergic and immune disorders where mast cells are implicated.

In certain embodiments, the compounds, compositions and methods are useful for treating any condition arising from increased activity of the lymphocyte activation pathway downstream of calcium entry such as NFAT (nuclear factor of activated T cells). In certain embodiments the compounds are also useful for treating inflammation arising from other calcium-dependent processes, including, but not limited to, mast cell degranulation and leukocyte secretion, as well as calcium-dependent elaboration of proinflammatory adhesion molecules, chemokines and cytokines by a variety of non-hemopoietic cells, including endothelial and epithelial cells.

Moreover, the compounds, compositions and methods of the present invention can also be used to prevent and/or treat inflammatory pulmonary disease or reactions (e.g., asthma, allergic rhinitis, chronic obstructive pulmonary disease, and adult respiratory distress syndrome), inflammatory musculoskeletal disease or reaction (e.g., exercise-induced injury, rheumatoid arthritis, psoriatic arthritis, osteoporosis and osteoarthritis), inflammatory gastrointestinal disease or urogenital reaction (e.g., enterocolitis, gastritis, Crohn's disease, interstitial cystitis, vaginitis, and ulcerative colitis), autoimmune disease or reactions (e.g., type II diabetes, inflammatory bowel disease, and psoriasis), irritable bowel syndrome, neurogenic inflammation and transplantation rejection reactions.

The compounds, compositions and methods of the present invention can also be used to prevent and/or treat inflammatory skin diseases (e.g., atopic dermatitis, eczema, contact dermatitis and allergic dermatitis), hyperproliferative skin diseases (e.g., psoriasis, basal cell carcinoma and squamous cell carcinoma), and skin irritation. Such conditions are well known to those of skill in the art and are described, e.g., in Champion et al., Eds. (1998) "*Textbook of Dermatology*", Blackwell Science, or in information provided by any of a number of organizations such as the American Academy of Dermatology (see, e.g., http://www.dermfnd.org/) and the American Cancer Society (see, e.g., http://www.cancer.org/). Further, the compounds and compositions of the present invention can be used to treat any symptom associated with any of these diseases or conditions, such as inflammation, redness, itching, pimples, crusts, scabs, dryness, burning, oozing, fluid, e.g., pus, discharge, pustules, blistering, rashes, disfiguration, scaling, dandruff, papules, plaques, lesions, thickenings, shedding, bumps, flaking, bleeding, tenderness, cuts, scratches, pain, cramps, irritation, swelling, blebs, vesicles, elevations, scarring, wrinkling, freckling, yellowing, blood vessel dilation, loss of normal function, and others.

The compounds, compositions and methods of the present invention are also useful for preventing and/or treating mucocutaneous inflammatory diseases such as asthma and allergic rhinitis as well as their associated symptoms. Descriptions of such conditions can be found in the Asthma and Allergy Foundation of America (see, e.g., http://www.aafa.org/) and are well known to those of skill in the art. Asthma is characterized by paradoxical narrowing of the bronchi that results in breathing difficulties. Typical symptoms associated with asthma include, e.g., wheezing, breathing difficulties, tightness of the chest, dry cough and shortness of breath after exercise. The compounds of the present invention can also be used to treat allergic rhinitis (hay fever). Allergic rhinitis results from an inflammatory reaction that occurs in the nasal passages in response to an allergic stimulus. Symptoms associated with allergic rhinitis include, e.g., sneezing, nasal congestion, nasal itching, nasal discharge and itching of the roof of the mouth and/or ears.

The compounds, compositions and methods of the present invention can also be used to prevent and/or treat skin aging, in particular extrinsic skin aging, as well as any symptoms associated with skin aging. Such symptoms include, for example, appearance of wrinkles and/or fine lines, slackening of cutaneous and subcutaneous tissue, sagging of the skin, atrophy of the epidermis, increased dryness of the skin, decrease in skin elasticity, increased fragility of capillaries, increased time of healing after injury, pigmentary alterations with areas of hyper- and hypopigmentation, appearance of a variety of benign, premalignant, and malignant neoplasms, and the like. Furthermore, at the histological level, aging results in thinning and deterioration of the skin, as well as in the reduction in cells and in blood supply, and a flattening in the junction between the dermis and epidermis.

In addition, compounds, compositions and methods of the present invention can be used to prevent and/or treat skin photodamage and any associated symptoms. Skin photodamage occurs with aging due to prolonged or repeated exposure to ultraviolet radiation. Signs of skin photodamage include, for example, wrinkling, yellowing, appearance of spots and mottling, elastosis, appearance of lines, leathery or dry appearance of the skin, and premature aging of the skin. At the histological level, skin photodamage may be reflected in tangled, thickened, abnormal elastic fibers, decreased collagen and increased glycosaminoglycan content (see, Tanaka et al. *Arch. Dermatol. Res.* 285:352–355, 2000).

The compounds, compositions and methods of the present invention are efficient for preventing and/or treating mucocutaneous inflammation and irritation caused by, for example, transdermal or transmucosal drug delivery, irritating drug delivery enhancers or irritating drug substances. The compounds and compositions of the present invention can also be used as excipients to enhance the potency of antiinflammatory drugs, such as corticosteroids, salicylates, colchicine, para-aminophenol, propionic acid, piroxicam, ketorolac, ketoprofen, cyclooxygenase inhibitors, indomethacin, and the like.

In yet another aspect, the present invention provides methods of treating an atopic disease, such as atopic dermatitis, allergic rhinitis or asthma, comprising: administering to a patient an HMG CoA reductase inhibitor (open-chain, lactone or combinations thereof) thereby treating the atopic disease. The HMG-CoA reductase inhibitors include, but are not limited to, mevastatin, lovastatin, fluvastatin, pravastatin, simvastatin, dalvastatin, cerivastatin and atorvastatin. The HMG CoA reductase inhibitor (open-chain, lactone or combinations thereof) can also be used to prevent and/or treat inflammatory skin diseases (e.g., atopic dermatitis, eczema, contact dermatitis and allergic dermatitis, a chronic obstructive pulmonary disease and adult respiratory distress syndrome), hyperproliferative skin diseases (e.g., psoriasis, basal cell carcinoma and squamous cell carcinoma), and skin irritation. Further, the HMG CoA reductase inhibitor (open-chain, lactone or combinations thereof) can be used to treat inflammatory gastrointestinal or urogenital disease or reaction such as inflammatory bowel disease, enterocolitis, gastritis, vaginitis, and interstitial cystitis.

VI. Pharmaceutical Compositions

The present invention provides compounds, methods and compositions for modulating inflammatory conditions and immune responses of mammals. The methods involve administering a compound of the present invention, a SOC inhibitor, capable of treating preexisting inflammatory conditions and immune disorders, and also preventing or reducing inflammation that would otherwise be induced by a drug or stimulus administered to mammals.

The present invention also provides pharmaceutical compositions for the administration of a compound of the present invention, a SOC inhibitor, to a patient in need thereof. In the context of the present invention, the term "patient" refers to an organism to which the compounds of the invention can be administered. Preferably, a patient is a mammal, e.g., a rodent, a primate or a human. A patient may be afflicted with a disease, or may be free of detectable disease in which case the compounds and compositions of the present invention are administered prophylactically. The compositions of the present invention can be administered to patients with an inflammatory disorder or condition.

The compounds of this invention can be formulated to be administered using any of a variety of routes, including, e.g., intravenous, intramuscular, transmucosal, oral or topical administration, such as, e.g., subcutaneously or transdermally, for prophylactic and/or therapeutic treatment.

The present compounds can be incorporated into a variety of compositions for therapeutic and/or prophylactic administration. A number of suitable formulations for use in the present invention are found in Remington's Pharmaceutical Sciences (Mack Publishing Company, Philadelphia, Pa., 17th ed., 1985) and in *Dermatological Formulations: Percutaneous absorption*, Barry (Ed.), Marcel Dekker Inc., 1983, both incorporated herein by reference. Moreover, for a brief review of methods for drug delivery, (see, Langer, *Science* 249:1527–1533, 1990), which is also incorporated herein by reference. The pharmaceutical compositions described herein can be manufactured in a manner that is known to those of skill in the art, i.e., by means of conventional mixing, dissolving, levigating, emulsifying, encapsulating, entrapping or lyophilizing processes. It will be appreciated that the present methods and excipients are merely exemplary and are in no way limiting.

More particularly, these compounds can be formulated into preparations in solid, semi-solid, or liquid forms suitable for local or topical administration, such as gels, water soluble (e.g., K-Y) jellies, creams, lotions, suspensions, foams, powders, slurries, ointments, suppositories, solutions, oils, pastes, sprays, emulsions, saline solutions, dimethylsulfoxide (DMSO)-based solutions, enemas, inhalers and aerosols. In general, carriers with higher densities, such as K-Y jelly, are capable of providing an area with a prolonged exposure to the active ingredients. In contrast, a solution formulation provides more immediate exposure of the active ingredient to the chosen area, although the effects generally do not last as long.

In addition to the formulations described supra, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, ORGELASE, water, calcium carbonate, calcium phosphate, various sugars, starches, cellulose derivatives, gelatin, and polymers such as polyethylene glycols.

For enteral administration the compounds of the invention can be administered in either single or multiple dosages. The compounds of the invention may be administered in combination with pharmaceutically acceptable carriers in a variety of dosage forms. For example, capsules, lozenges, hard candies, powders, sprays, aqueous suspensions, elixirs, syrups, and the like may be formulated with various pharmaceutically acceptable inert carriers. Such carriers include solid diluents or fillers, sterile aqueous media and various non-toxic organic solvents. In general, the compounds of the invention will be included in oral dosage forms at concentration levels ranging from about 0.5% to about 90% by weight of the total composition, in amounts which are sufficient to provide the desired unit dosage.

Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

For parenteral use, the compounds of the invention may be formulated by means known in the art using suitable dispersing or wetting agents and suspending agents. A sterile injectable formulation can also be a solution or suspension in a non-toxic parenterally acceptable diluent or solvent, for example, as a solution in 1,3-butandiol. Among the acceptable vehicles and solvents are water, Ringer's solution and isotonic NaCl solution, fixed oils (including synthetic mono- or di-glycerides), fatty acids (such as oleic acids), and mixtures thereof.

Pharmaceutical compositions suitable for use in the present invention include compositions wherein the active ingredients are contained in a therapeutically or prophylactically effective amount. The amount of compound or composition administered will, of course, be dependent on the subject being treated, on the subject's weight, the severity of the affliction, the manner of administration and the judgment of the prescribing physician. Determination of an effective amount is well within the capability of those skilled in the art, especially in light of the disclosure provided supra.

As used herein, "effective amount," or "therapeutically effective amount" refers to an amount of any of the present compounds that results in treatment of the medical condition, i.e., reduction in pain, redness, inflammation, or any other symptom. Alternatively, an "effective amount" may be determined by monitoring reduction in any detectable symptom of the condition, such as the degree of swelling, inflammation, redness, size of the affected area, and the like. In the context of the present invention, "prophylactically effective amount" refers to an amount of any of the present compounds that prevents the development or relapse of a medical condition. For example, a "prophylactically effective amount" is an amount that protects a subject from the deleterious effects of ultraviolet irradiation and that thus prevents photodamage and/or the appearance of signs of skin aging. In diseases that relapse periodically, such as atopic dermatitis or psoriasis, administration of a prophylactically effective amount of a compound of the invention may be an amount useful for preventing the relapse of the condition.

For any compound used in the method of the invention, a therapeutically effective dose can be estimated initially from animal models (described supra), well-known to those of skill in the art. Such information can be used to more accurately determine useful doses in humans. Initial dosages can also be estimated from in vitro or in vivo data.

Initial dosages can also be formulated by comparing the effectiveness of the compounds described herein in model assays with the effectiveness of known drugs. For instance, initial dosages can be formulated by comparing the effectiveness of the compounds described herein in model assays with the effectiveness of other compounds that have shown efficacy in treating the present conditions. In this method, an initial dosage can be obtained by multiplying the ratio of effective concentrations obtained in the model assay for the present compound and the control compound by the effective dosage of the control compound. For example, if the present compounds are twice as effective in a model assay as a known compound (i.e., the EC50 of the compound is equal to one-half the EC50 of the known compound in the same assay), an initial effective dosage of the compound of the present invention would be one-half the known dosage for the known compound. Using these initial guidelines one having ordinary skill in the art could readily determine an effective dosage in humans or other mammals.

Moreover, toxicity and therapeutic efficacy of the compounds described herein can be determined by standard pharmaceutical procedures in cell cultures or experimental animals, e.g., by determining the LD50 (the dose lethal to 50% of the population) and the ED50 (the dose therapeutically effective in 50% of the population). The dose ratio between toxic and therapeutic effect is the therapeutic index and can be expressed as the ratio between LD50 and ED50. Compounds which exhibit high therapeutic indices are preferred. The data obtained from these cell culture assays and animal studies can be used in formulating a dosage range that is appropriate for use in humans. The dosage of such compounds lies preferably within a range of concentrations that include the ED50 with little or no toxicity. The dosage may vary within this range depending upon the dosage form employed and the route of administration utilized. The exact formulation, route of administration and dosage can be chosen by the individual physician in view of the patient's condition (see, for example, Fingl et al. "*The Pharmacological Basis of Therapeutics*" Ch. 1, p. 1, 1975).

Dosage amount and interval may be adjusted individually to provide levels of the active compound which are sufficient to maintain therapeutic effect. One having skill in the art will be able to optimize therapeutically effective local dosages without undue experimentation.

In pharmaceutical dosage forms, the compounds may be administered in the form of their pharmaceutically acceptable salts, or they may also be used alone or in appropriate association, as well as in combination with other pharmaceutically active compounds. Agents of particular use in the formulations of the present invention include, for example, local anesthetics, counterirritants, anti-inflammatory agents, or any agent that has a therapeutic effect for inflammatory diseases or conditions.

The preferred anti-inflammatory agents include, but are not limited to, prescription and nonprescription topical and aerosol corticosteroids, non-steroidal anti-inflammatory agents including salicylates, colchicine, para-aminophenols, propionic acids, macrolide immunosuppressives, dapsone, clobetasol, halobetasol, diflorasone, piroxicam, ketorolac, ketoprofen, indomethacin and specific cyclooxygenase inhibitors.

The preferred counterirritants include, but are not limited to, glycerol, corticosteroids and salicylates. The preferred anesthetics include, but are not limited to, amide caines and counterirritants with lidocaine, cocaine, bupivicaine, mepivicaine, etidocaine, chloroprocaine, proparacaine, tetracaine, benzacaine, prilocaine, benoxinate, dibucaine, dyclonine, pramoxine, menthol, resorcinol, thymol and camphor.

Any other compound that has potential efficacy in the treatment of the present conditions can also be used.

The present formulations can be administered to treat an existing disease or condition, or can be used prophylactically. In prophylactic applications, compositions containing the present compounds can be administered to a patient that is not already in a disease state in order to enhance the patient's resistance or to prevent or retard the progression of a disease or condition. Such an amount is defined as a "prophylactically effective dose or amount." In this use, the precise amounts again depend upon the patient's state of health and general level of immunity.

The present compositions can be administered to a patient using a variety of routes, such as oral, parenteral or local routes. The present compositions are typically administered to a patient as a local application, where "local application," or "locally applied," refers to the administration of a composition at the local site of the disease, whether by local injection, topical administration, or any such method that results in a relatively high concentration of the present compounds at the site of the disease. As such, administration of the compounds can be achieved in various ways, including by topical application of the composition to the site of the disease or condition, i.e., direct application of a formulation to the affected skin or mucous membrane. In addition, compositions can be formulated for injection and injected locally at the site of the disease or condition, e.g., local subcutaneous injection at the site of the disease.

The present compositions can be applied to any site of any of the present conditions, including localized conditions or conditions affecting large areas of the body or even covering the entire body, can be applied to the skin and/or to mucous membranes, and can be applied to any affected part of the body, including the face, forehead, chin, eyes, eyelids, eyebrows, nose, skin near the nose, cheeks, ears, mouth, tongue, inside of the cheeks, gums, head, hair, scalp, neck, chest, back, lower back, armpit, skin folds of armpit, elbow, elbow fold, wrists, ankles, legs, arms, insides of wrists, insides of arms, nails, knees, area behind knees, hands, feet, palms, soles, fingers, toes, genitals, or any other affected part of the body.

The present compositions can be administered one time or multiple times, depending on the compound, the severity of the condition, and the initial response of the condition to the treatment. For example, the compositions can be administered 1, 2, 4, or more times per day, and can be administered every 1, 2, 4, 7, or more days. Such treatments can be administered for a limited duration, or indefinitely until the condition has resolved. The compositions can be applied locally as a "leave on" product, meaning that the composition is applied to the patient and allowed to remain indefinitely at the site of application, or as a "wash off" product, meaning that the composition is allowed to remain at the site of application for a limited amount of time, e.g., for a certain number of seconds, minutes, hours, etc.

Administration of a SOC inhibitor by inhalation is a particularly useful means of treating an individual having an inflammatory lung disease. One skilled in the art would recognize that a SOC inhibitor can be suspended or dissolved in an appropriate pharmaceutically acceptable carrier and administered, for example, directly into the lungs using a nasal spray or inhalant.

A pharmaceutical composition comprising a SOC inhibitor can be administered as an aerosol formulation. An aerosol formulation contains a SOC inhibitor dissolved, suspended or emulsified in a propellant or a mixture of solvent and propellant and is intended for administration as a nasal spray or inhalant. The aerosol is administered through the respiratory system or nasal passages.

An aerosol formulation used for nasal administration is generally an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used. Antimicrobial agents or preservatives can also be included in the formulation.

An aerosol formulation used for inhalations and inhalants is designed so that the SOC inhibitor is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the SOC inhibitor. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (*Reminaton's Pharmaceutical Sciences* 18th ed., Gennaro, A. R., ed., Mack Publishing Company, Easton, Pa. (1990)).

Halocarbon propellants useful in the invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers.

The SOC inhibitor can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, supra, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as a SOC inhibitor in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient SOC inhibitor and a propellant and can include any combination of solvents and preservatives or antioxidants.

An aerosol formulation can also be a dispersion or suspension. A suspension aerosol formulation will generally contain a suspension of a SOC inhibitor and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient SOC inhibitor. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing a SOC inhibitor will generally have a minimum of 90% of the particles in inhalation products between about 0.5 and about 10 $\mu$m to maximize delivery and deposition of the SOC inhibitor to respiratory fluids. In particular, the particle size can be from about 3 to about 6 $\mu$m.

A pharmaceutical composition comprising a SOC inhibitor also can be incorporated, if desired, into liposomes, microspheres or other polymer matrices (Gregoriadis, Liposome Technology, Vols. I to III, 2nd ed., CRC Press, Boca Raton, Fla. (1993)). Liposomes, for example, which consist of phospholipids or other lipids, are nontoxic, physiologically acceptable and metabolizable carriers that are relatively simple to make and administer.

In order to treat an individual having an inflammatory lung disease to alleviate a sign or symptom of the disease, a SOC inhibitor should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of a SOC inhibitor required to obtain an effective dose in a subject depends on many factors, including the particular inflammatory lung disease being treated, the age, weight and general health of the subject and the particular SOC inhibitor being administered as well as the route of administration and the number of treatments to be administered. In view of these factors, the skilled artisan would adjust the particular dose so as to obtain an effective dose for treating an individual having an inflammatory lung disease.

The effective dose of a SOC inhibitor will depend on the particular SOC used and the mode of administration, as well as the weight of the individual being treated. The dosages described herein are generally those for an average adult. The dose will generally range from about 0.1 mg to about 3500 mg. Unlike the use of SOC inhibitors for the treatment of high cholesterol, the present invention is directed to methods of treating inflammation, which can be treated as an acute response. Therefore, the SOC inhibitors of the invention can be administered at high doses relative to those given for lowering cholesterol levels. The dose will generally be at least about 10 mg per day, at least about 100 mg per day, at least about 200 mg per day, at least about 250 mg per day, at least about 300 mg per day, at least about 400 mg per day, or at least about 500 mg per day, and can be at least about 1000 mg per day. The use of relatively high doses is particularly useful for systemic administration of a SOC inhibitor.

When administering high doses of a SOC inhibitor, one skilled in the art can monitor for any possible adverse side effects. Methods of monitoring adverse side effects of a SOC inhibitor, including myopathy, are described, for example, in Thibault et al., Clinical Cancer Res. 2:483–491 (1996). One skilled in the art can monitor for any adverse side effects and, if necessary, adjust the dosage to minimize adverse side effects while optimizing the effectiveness of treating an inflammatory lung disease.

For administration in an aerosol formulation, the dose of SOC inhibitor can generally be lower than the dose used for systemic administration. For example, a SOC inhibitor can be administered at a dose higher than about 0.1 mg per day to about 80 mgs per day.

The concentration of a SOC inhibitor in a particular formulation will depend on the mode and frequency of administration. A given daily dosage can be administered in a single dose or in multiple doses so long as the SOC inhibitor concentration in the formulation results in the desired daily dosage. For example, a given formulation can contain a SOC inhibitor at a concentration of about 0.1 mg to about 80 mg. One skilled in the art can adjust the amount of SOC inhibitor in the formulation to allow administration of a single dose or in multiple doses that provide the desired concentration of SOC inhibitor over a given period of time. For example, the formulation can be adjusted to allow administration of a single dose or multiple doses that provides greater than 0.1 mg per day of a SOC inhibitor.

The invention also provides a method of treating an inflammatory lung disease, comprising administering a pharmaceutical composition comprising an aerosol formulation of a SOC inhibitor, wherein the SOC inhibitor is administered in an aerosol formulation at an amount or total dosage lower than in a systemic formulation. For example, the amount or total dosage administered as an aerosol formulation can be administered at a dosage lower than the amount or total dosage that would be administered by other modes of administration such as systemic, intraperitoneal or oral administration.

It will be appreciated that the present methods of treatment can be applied alone or in combination with other surgical or non-surgical treatments for these conditions.

EXAMPLES

The following examples are offered to illustrate, but not to limit, the claimed invention.

Example 1

This example illustrates synthesis of a novel compound of this invention from Fluvastatin. Fluvastatin sodium (5.83 g), which was isolated from Lescol® capsules (commercially available from Novartis Pharmaceuticals, East Hanover, N.J.), was dissolved in 100 mL mixture of methanol and water (50/50, v/v). 50 mL of 10% HCl and 50 mL of methanol were added into the solution and refluxed for 2 hours. Solvent was removed by rotovaping under vacuum to obtain an orange residue. The dry residue (3.23 g) was subjected to silica gel column chromatography twice with hexane/methylene chloride/methanol gradient. The yellow crystals obtained from the fraction 1079-76-3 (Formula II) were re-crystallized with methylene chloride and methanol mixture to produce 1079-76-3C (124 mg). Mass spectrometry and $^1$H-NMR analysis were performed to identify the fractions as dehydrated methyl ester derivatives of Fluvastatin containing a conjugated all trans triene system in the side chain. $^{13}$C-NMR analysis confirmed the provisional structure of 1079-76-3C.

Structure Elucidation $^1$H-NMR (CDCl$_3$): 1.76 (6H, d), 3.75 (3H, s), 4.9 (1H, m), 5.87 (1H, d), 6.24 (1H, dd), 6.35 (1H, dd), 6.64 (1H, dd), 6.77 (1H, d), 7.33 (1H, dd), 7.1–7.55 (8H, m)

$^{13}$C-NMR (CD Cl$_3$): 21.77, 47.81, 51.52, 111.84, 115.52, 117.03, 119.78, 119.98, 120.64, 122.62, 125.28, 128.58, 130.4, 131.20, 131.88, 132.75, 133.12, 136.02, 140.59, 144.23, 165.18, 167.44

MS (Electrospray) m/z: 430.1, 412.6, 389.7 (M$^+$), 304.6, HRMS obs: 390.186700, calc: 390.186933 for C$_{25}$H$_{25}$NO$_2$F
IR (KBr): 1712, 1603, 1499, 1242, 1135, 1010, 835, 745

The biological activity of column fractions and crystalline material was assessed in the NFAT activation assay using Jurkat cells stably transfected with NFAT-regulated luciferase reporter (see, FIGS. 9–14).

Figure 7:
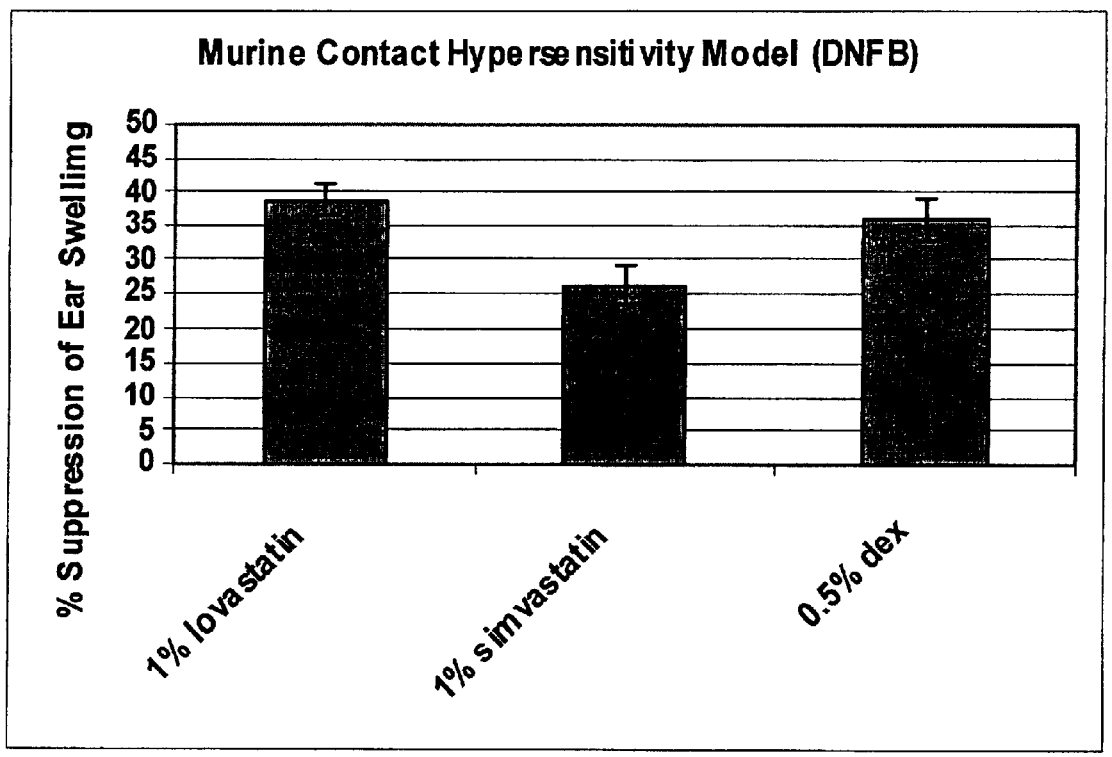
FIG. 7 illustrates the inhibition of DNFB (dinitrofluorobenzene)-induced contact hypersensitivity response in mouse by lovastatin and simvastatin.
Figure 8:
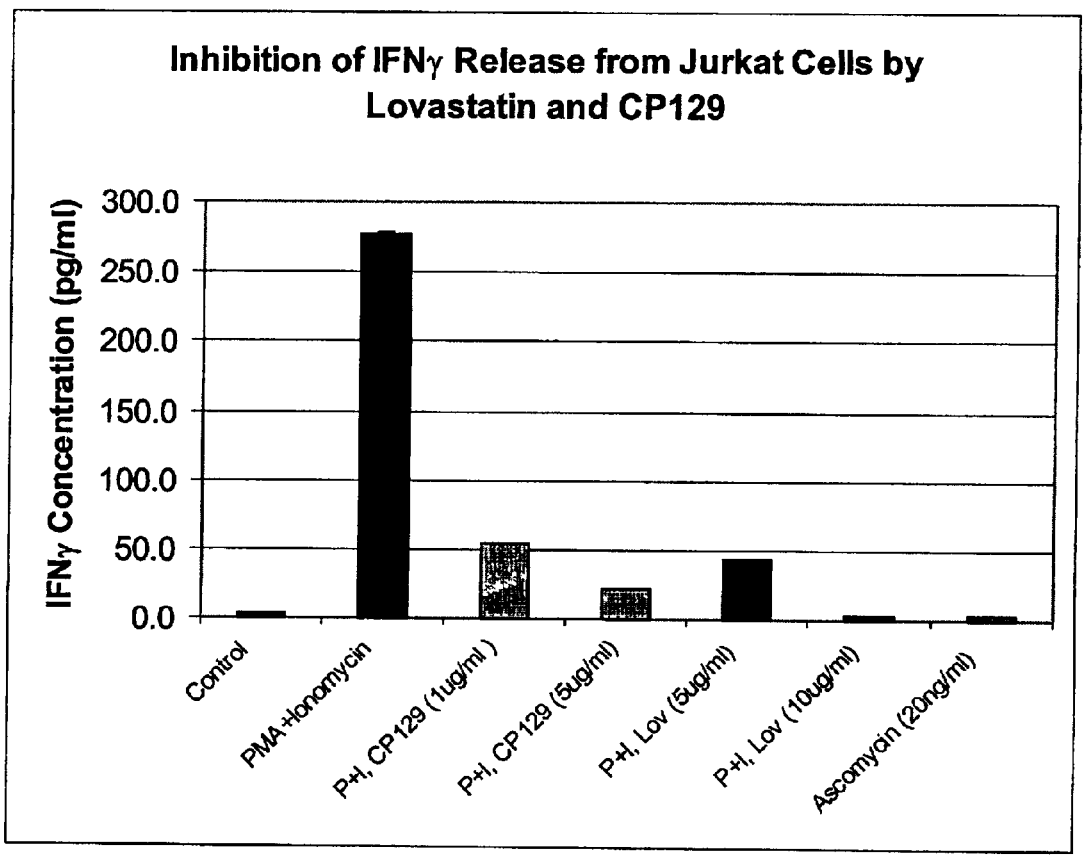
FIG. 8 illustrates the inhibition of IFN-gamma production by lovastatin and CP-129, a mixture of active fluvastatin derivatives.
Figure 9:
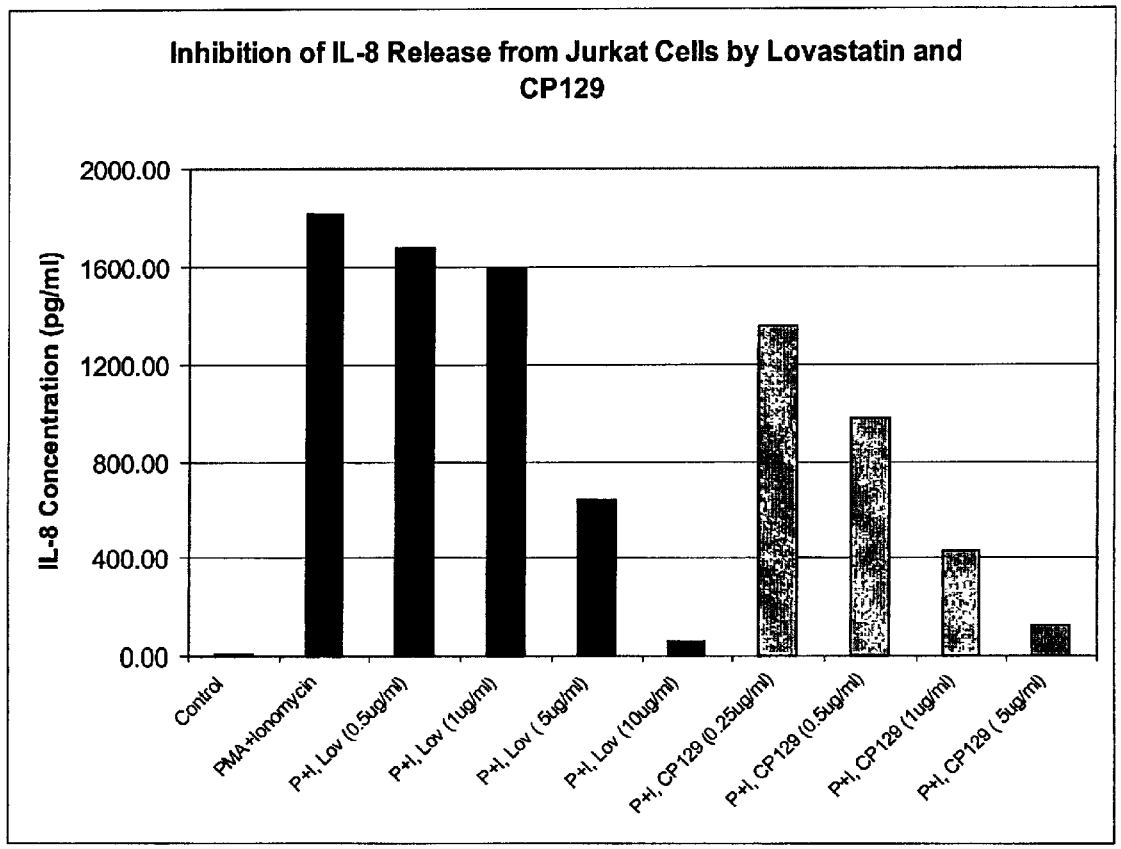
FIG. 9 illustrates the inhibition of IL-8 production from Jurkat cells by lovastatin and CP-129.
Figure 10:
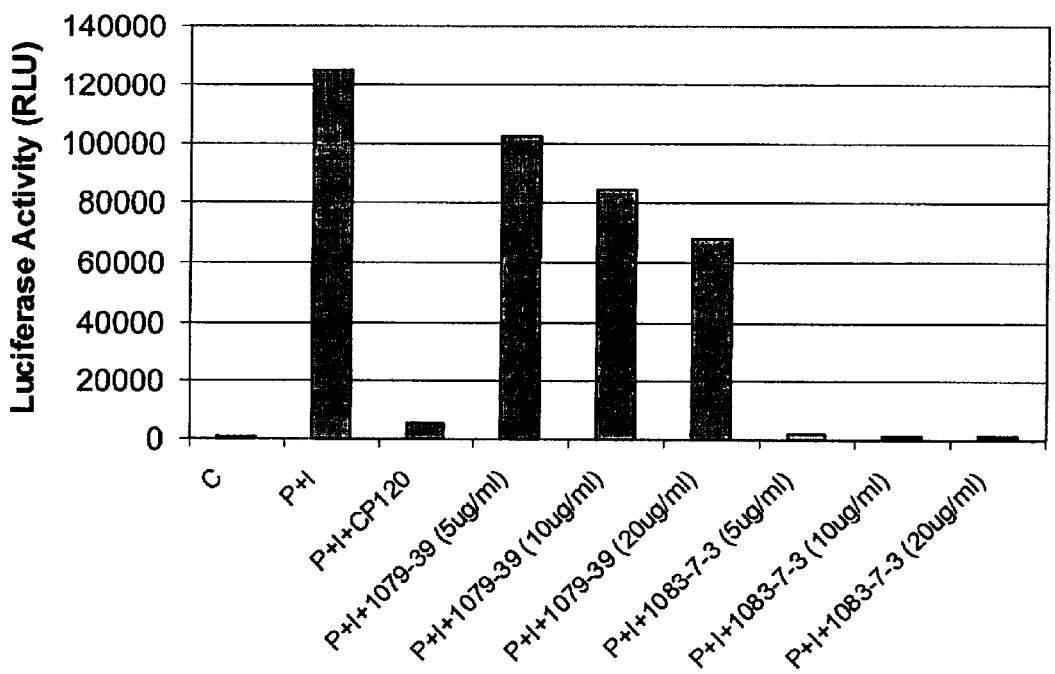
FIG. 10 illustrates the inhibition of NFAT-luciferase activity in Jurkat cells by fluvastatin fractions 1–4 and 8–11 (fractions 8–11 are the same as CP-129).
Figure 11:
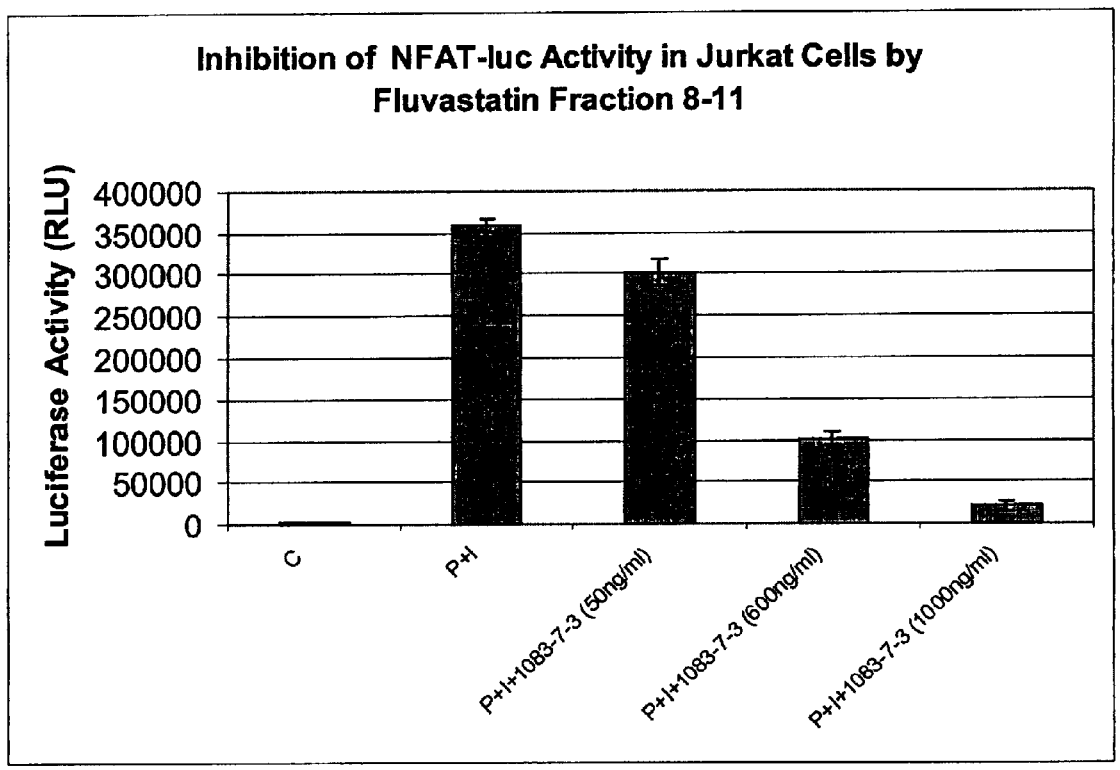
FIG. 11 illustrates the inhibition of NFAT-luciferase activity in Jurkat cells by fluvastatin fractions 8–11 at lower concentrations.
Figure 12:
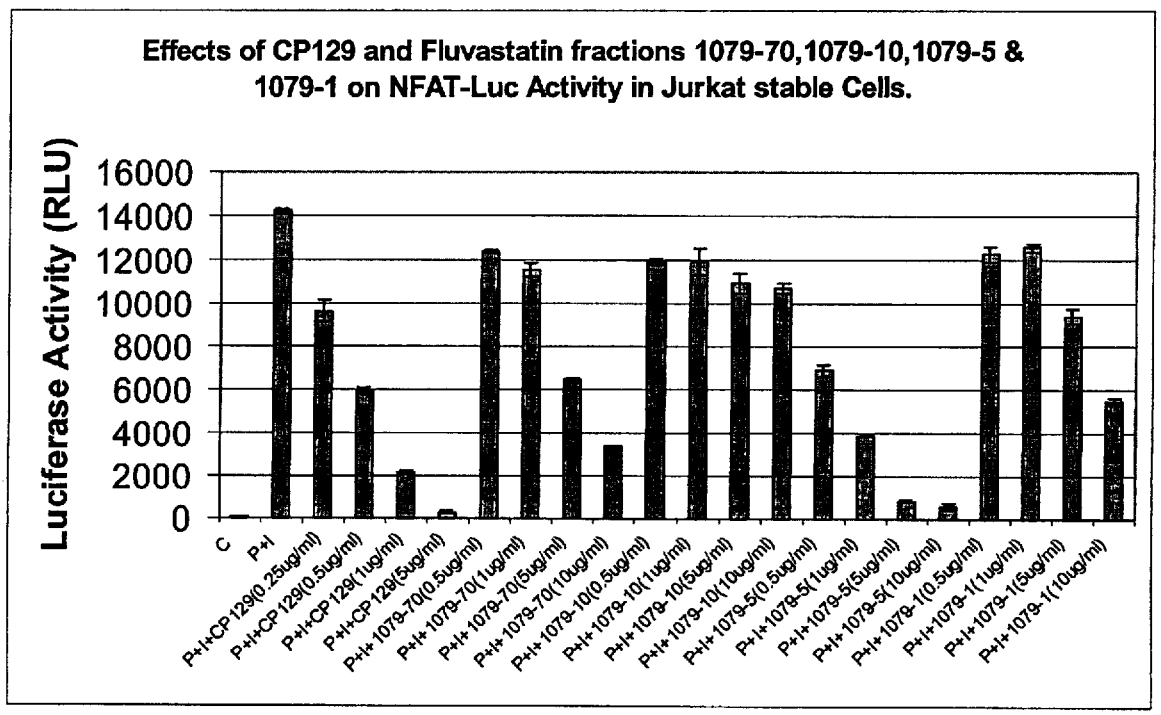
FIG. 12 illustrates the effects of CP129, 1079-70, 1079-10, 1079-5 and 1079-5 & 1079-1 on NFAT-luciferase activity in Jurkat cells.
Figure 13:
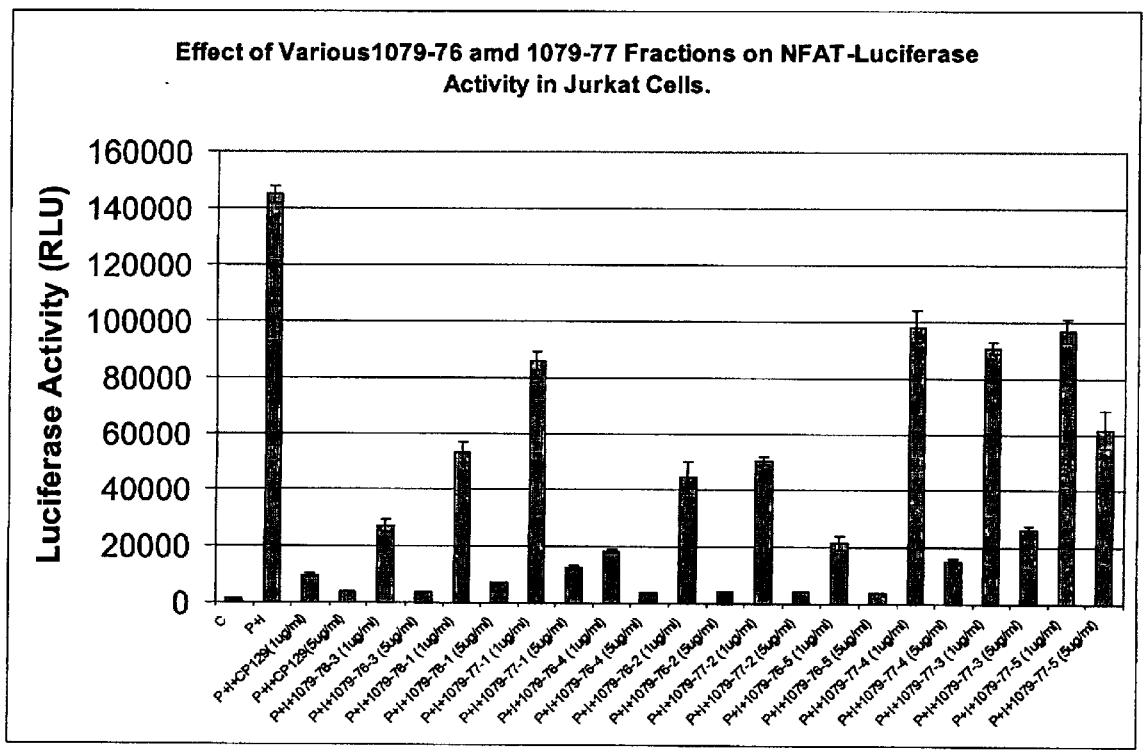
FIG. 13 illustrates the effect of various 1079-76 and 1079-77 fractions on NFAT-luciferase activity in Jurkat/NFAT-luciferase stable cells.
Figure 14:
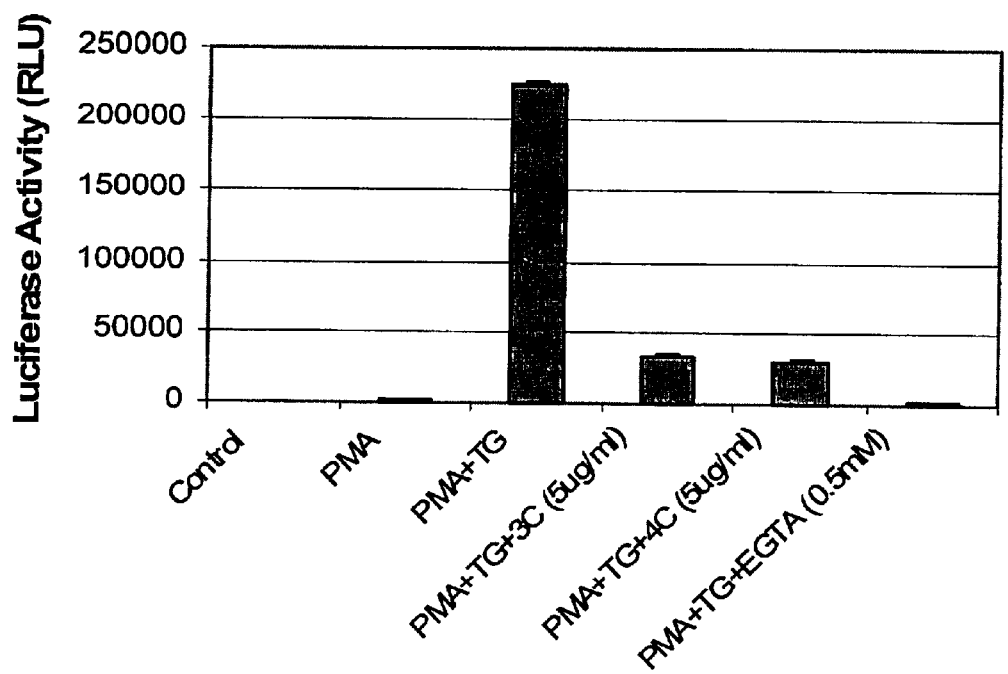
FIG. 14 illustrates the effects of two crystal fractions of 1079-76-3 and 1079-79-4 on NFAT-luciferase activity in Jurkat stable cells stimulated with ionomycin and phorbol-12-myristate, 13-acetate in peripheral mononuclear cells (PMA).

CP-129, a mixture containing the 1079-76-3C, 1079-76-4C, and related entities was shown to inhibit IFN-gamma and IL-8 production from Jurkat cells (see, FIGS. 7 and 8).

Example 2

This example illustrates the effect of novel compounds of this invention on NFAT activity, IL-2 and TNF-alpha secretion.

The effects of the novel compounds 1079-76-3C and 1079-76-4C on nuclear factor of activated T-cell (NFAT) activation were investigated in Jurkat cells (human leukemic T-cells). The novel compounds inhibited the expression of an NFAT-regulated reporter gene stably transfected into Jurkat cells, stimulated with ionomycin (I) and phorbol-12-myristate, 13-acetate (PMA) (see, FIG. 13), or with thapsigargin (TG)+PMA (see, FIG. 14).

Jurkat cells, in standard medium, were seeded in 24-well dishes at 1 million cells per well and treated as follows. The cells were pre-incubated for 15 minutes with the test compound (CP-129, 1079-76-3C or 1079-76-4C, at final concentrations of 5 μg/mL), and then stimulated by addition of 0.3 μM TG+20 ng/mL PMA. The cells were harvested 5 hours later and luciferase activity was measured in a luminometer. 1079-76-3C and 1079-76-4C inhibited TG+PMA-induced NFAT activity approximately 85% at 5 μg/mL, while CP129 completely inhibited TG+PMA-induced NFAT activity at 5 μg/mL.

Figure 15:
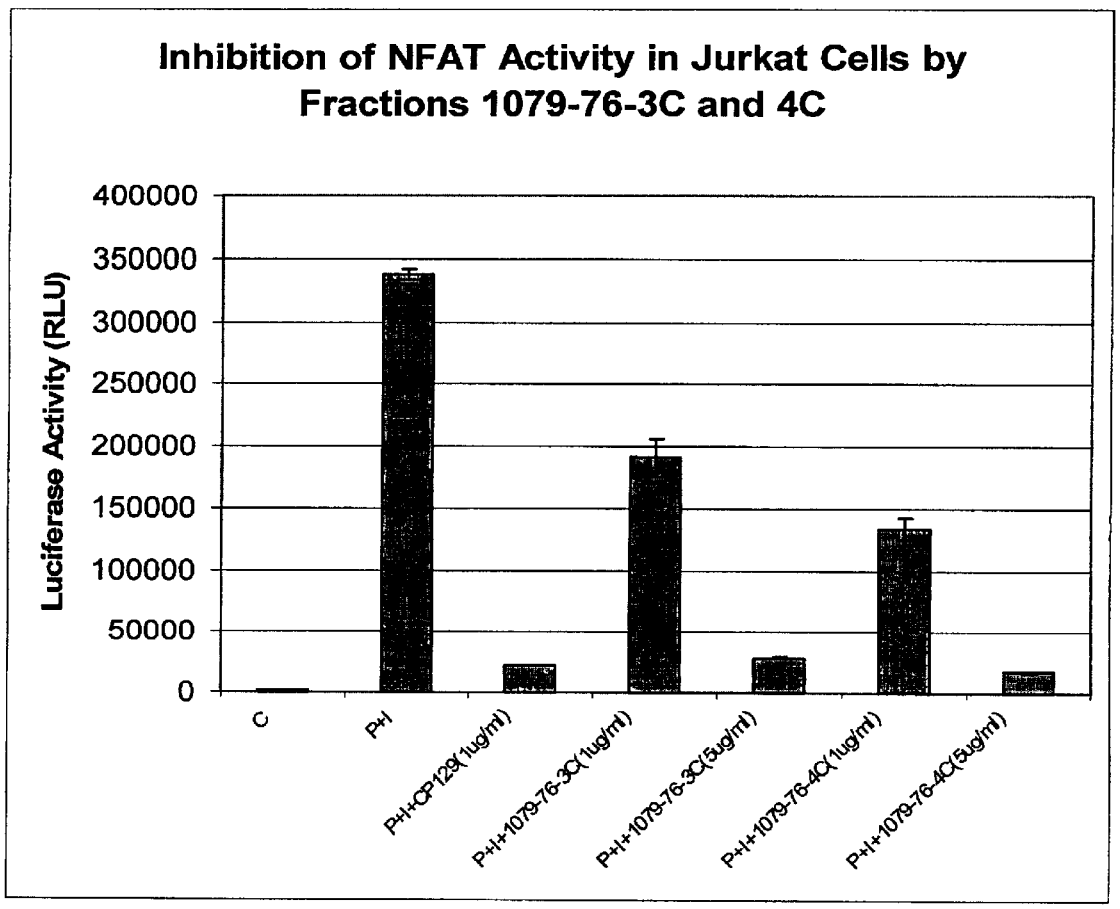
FIG. 15 illustrates the effects of two crystal fractions of 1079-76-3 and 1079-79-4 on NFAT-luciferase activity in Jurkat cells stimulated with thapsigargin and phorbol-12-myristate, 13-acetate in peripheral mononuclear cells (PMA).
Figure 16:
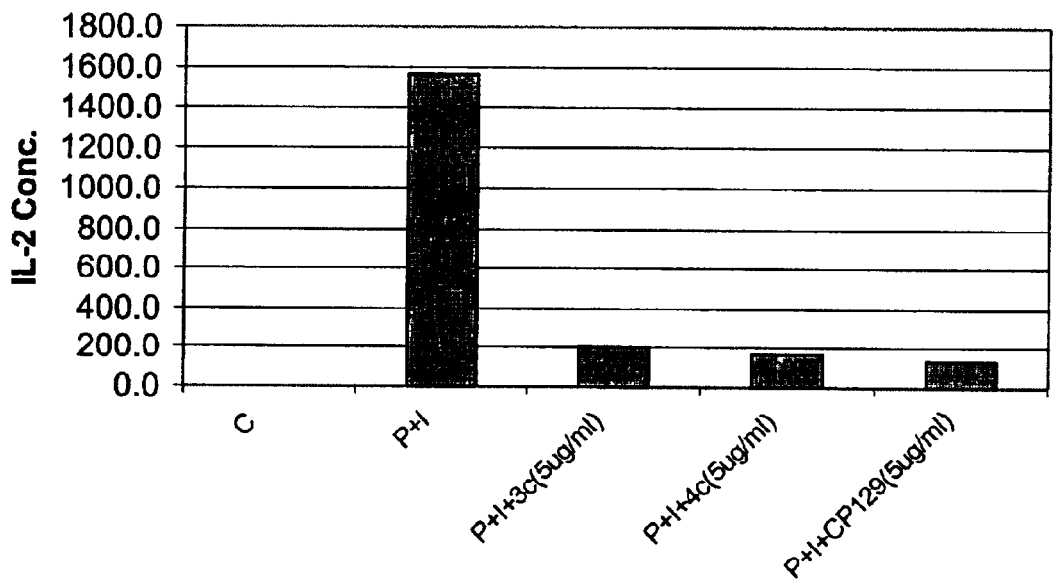
FIG. 16 illustrates the inhibitory effect of CP-129, 1079-76-3C and 1079-76-4C on IL-2 release by PMA and ionomycin in Jurkat cells.
Figure 17:
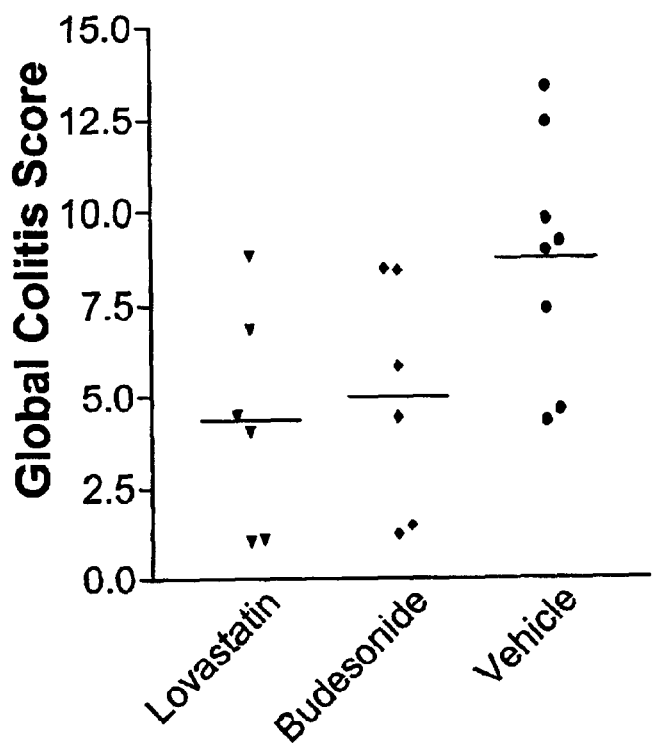
FIG. 17 illustrates the reduction of TNBS-induced colitis by lovastatin.
Figure 18:
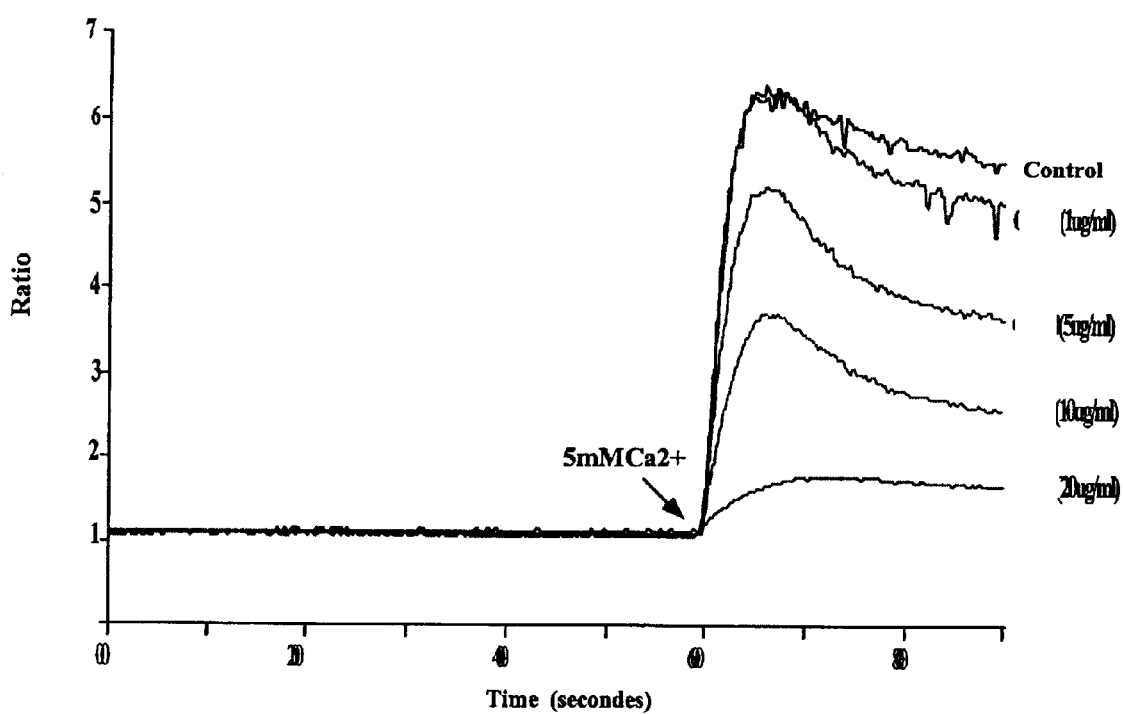
FIG. 18 illustrates calcium inhibition by a SOC inhibitor of the present invention.

Since NFAT plays a critical role in IL-2 and TNFα gene transcription, the effects of the novel compounds on IL-2 and TNFα secretion from stimulated lymphoid cells were also investigated. Jurkat cells, in standard medium, were seeded into 24-well dishes at 1 million cells per well and were treated as follows: The cells were pre-incubated for 30 minutes with 5.0 μg/mL CP-129, 1079-76-3C or 1079-76-4C, then stimulated with 20 ng/mL PMA and 1 μg/mL ionomycin for 5 hours. Following centrifugation, the supernatants were analyzed for IL-2 content by ELISA using a standard protocol. In this experiment, CP-129, 1079-76-3C and 1079-76-4C were found to inhibit IL-2 release by PMA and ionomycin in Jurkat cells (see, FIG. 15).

The following compounds were tested in the foregoing assay and their respective IC$_{50}$ are as set forth below in Table III.

TABLE III

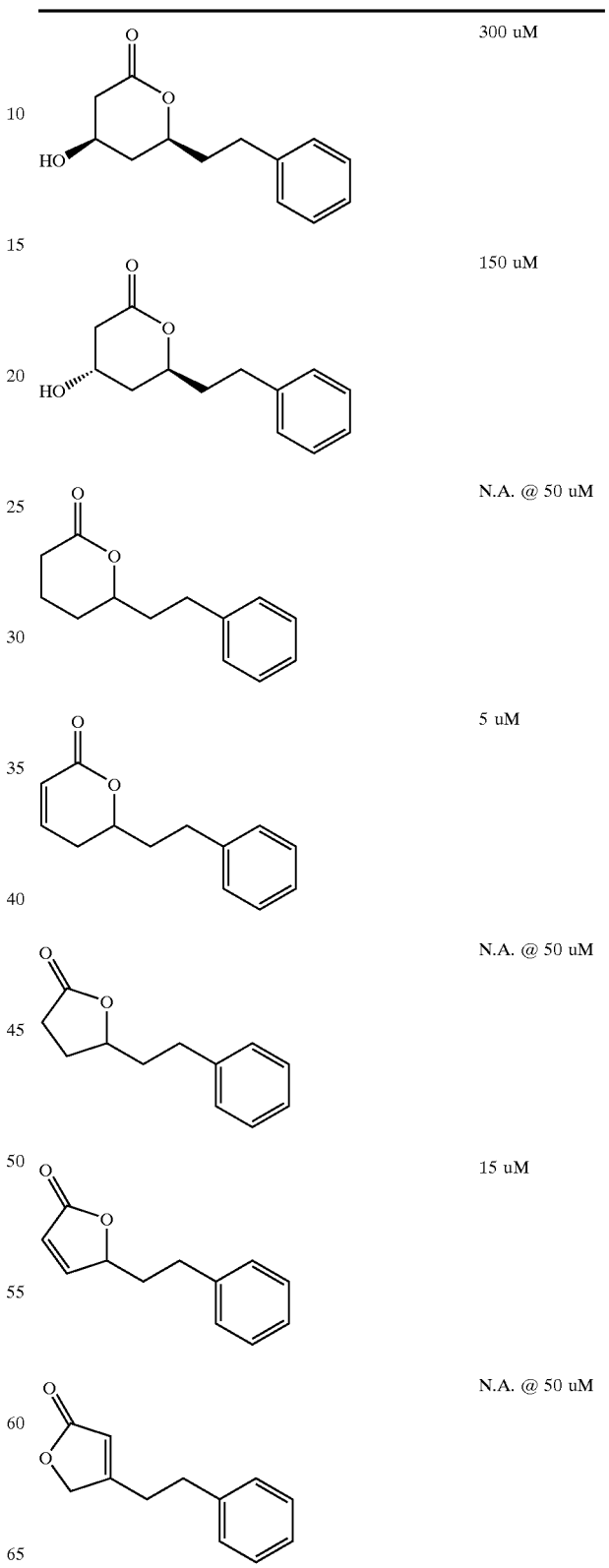

| | |
|---|---|
| | 300 uM |
| | 150 uM |
| | N.A. @ 50 uM |
| | 5 uM |
| | N.A. @ 50 uM |
| | 15 uM |
| | N.A. @ 50 uM |

TABLE III-continued

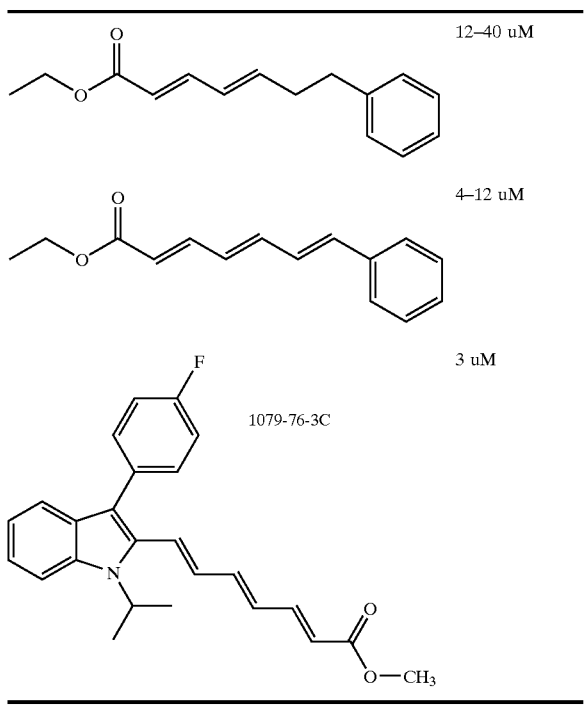

Example 3

This example illustrates the preparation of enema compositions.

Water and Olive Oil Enemas

The water suspension enema is prepared by suspending 6 mg of micronized simvatatin in an appropriate amount of purified water, USP, along with 5 g of sorbitol and 500 mg of carboxymethyl cellulose to form 60 mL of a 10% (w/v) aqueous suspension. Simvastatin enema suspensions of different concentrations are prepared by varying the amount of micronized simvastatin used, depending on the desired concentration and the purity of the drug material. Water suspension enemas using different micronized actives (e.g., lovastatin, fluvastatin, compounds of this invention, etc.) are prepared by substituting other drugs for the simvastatin in the above formulation.

An olive oil suspension enema is prepared by suspending 9 mg of lovastatin in an appropriate amount of olive oil, to prepare 60 mL of a 15% (w/v) suspension. Lovastatin enema suspensions of different concentrations are prepared by varying the amount of micronized lovastatin used, depending on the desired concentration and the purity of the drug material. Olive oil suspension enemas using different micronized actives (e.g., simvastatin, fluvastatin, compounds of this invention, etc.) are prepared by substituting other drugs for the lovastatin in the above formulation.

Hydrophilic and Hydrophobic Enemas

The hydrophilic enema vehicle is prepared in the same manner as the water suspension enema by combining 2.5 g of medium viscosity carboxymethylcellulose, 25 g sorbitol, and an appropriate amount of purified water, USP to prepare 300 mL of vehicle. The hydrophobic enema vehicle is prepared by adding 15 g of Witepsol H-15 (Huls America Inc., NJ) to 300 mL of hydrophilic enema vehicle. Enema vehicles are made acidic by adding 25.3 g of sodium citrate and 2.8 g of citric acid monohydrate to create a vehicle with a pH of 5.5. Enema vehicles are made basic by adding 26.15 g of sodium phosphate and 0.25 g of sodium phosphate monobasic to create a pH 8.5 enema vehicle.

The hydrophilic, acidic atorvastatin enema is prepared by suspending approximately 20 mg of micronized atorvastatin (depending on drug purity) in an appropriate amount of acidic hydrophilic vehicle to prepare 100 mL of a 20% (w/v) atorvastatin suspension.

The hydrophobic, basic enema containing the compound prepared in Example 1 or other compounds of this invention is prepared by micronizing the compound, and suspending approximately 1 mg of the micronized compound (depending on drug purity) in an appropriate amount of basic hydrophobic vehicle to prepare 100 mL of a 1% (w/v) enema suspension.

Hydrophilic and hydrophobic enemas using different micronized actives (e.g., simvastatin, fluvastatin, the compounds of this invention, etc.) are prepared by substituting other drugs for the active compound in the above formulation.

Carbomer Enemas

The pravastatin and carbomer enema is prepared by combining 10 mg of micronized pravastatin, 400 mg of carbomer (Carbopol® 974P, commercially available from B. F. Goodrich, Charlotte, N.C.), 100 mg xanthan gum, 150 mg methylhydroxybenzoate, 15 mg propylhydroxybenzoate, and an appropriate amount of purified water, USP to prepare 90 mL of enema suspension. The pH of the suspension is then adjusted to 5.5 with a potassium/sodium phosphate buffer solution, and an appropriate amount of purified water to bring the total volume to 100 mL is added. This produces 100 mL of a 10% (w/v) pravastatin suspension enema containing carbomer.

The dalvastatin and carbomer enema is prepared by combining 20 mg of micronized pravastatin, 400 mg of carbomer (Carbopol® 974P, B. F. Goodrich, Charlotte, N.C.), 100 mg xanthan gum, 150 mg methylhydroxybenzoate, 15 mg propylhydroxybenzoate, and an appropriate amount of purified water, USP to prepare 90 mL of enema suspension. The pH of the suspension is then adjusted to 4.2 with tromethamine, and an appropriate amount of purified water to bring the total volume to 100 mL is added. This produces 100 mL of a 20% (w/v) dalvastatin suspension enema containing carbomer.

Carbomer enemas using different micronized actives (e.g., simvastatin, fluvastatin, the compounds of this invention, etc.) are prepared by substituting other drugs for the active compound in the above formulation.

Propylene Glycol Enemas

In a first vessel, 10.6 g propylene glycol USP, 2.65 g ethyl alcohol, 0.398 g benzyl alcohol, and 0.305 g benzoic acid USP are combined. Approximately 2.5 mg of micronized cerivastatin is added to the first vessel with agitation. Next, 1.113 g of hydroxymethylcellulose is added to the first vessel. In a second vessel, 1.02 g of sodium benzoate, NF is combined with 9 g purified water USP until dissolved. The mixtures in the first and second vessels are then combined with agitation, and additional purified water is added as needed to bring the volume to 25 mL. This produces a propylene glycol-based enema composition containing 10% (w/v) cerivastatin.

Fluvastatin sodium enemas are prepared by combining 424 g propylene glycol USP, 106 g ethyl alcohol, 15.9 g benzyl alcohol, and 12.2 g benzoic acid USP in a first vessel. 10 of the 20 mg Lescol® capsules (commercially available from Novartis Pharmaceuticals, East Hanover, N.J.), equivalent to 200 mg of fluvastatin sodium, are opened, the contents pulverized and added through a 20 mesh screen into the first vessel with agitation. Next, 44.52 g of hydroxymethylcellulose is added to the first vessel. In a second vessel, 40.8 g of sodium benzoate, NF is combined with 400 g purified water USP until dissolved. The mixtures in the first and second vessels are then combined with agitation, and additional purified water is added as needed to bring the volume to 1 L. This produces a propylene glycol-based enema composition containing 10% (w/v) fluvastatin sodium.

Propylene glycol enemas using different micronized actives (e.g., simvastatin, fluvastatin, the compounds of this invention, etc.) are prepared by substituting other drugs for the fluvastatin in the above formulation.

Example 4

This example illustrates the preparation of suppository compositions.

Polybase Suppositories

Polybase suppositories are prepared using the fusion method. 8 g of polybase (a homogeneous mixture of polyethylene glycols and polysorbate 80) is melted in a vessel with constant stirring to 40° C. The compound prepared and isolated in Example 1 is micronized, and approximately 2 g of the micronized compound (depending on the purity of the compound) is added to the molten polybase while stirring. The molten mixture is then stirred continuously for 15 minutes while maintaining the temperature at 40° C. The melt is then poured into 2 mL disposable plastic suppository molds and allowed to cool to ambient temperature, approximately 25° C. The cooled molds are then hardened in an ice bath for 1 hour. This procedure produces polybase suppositories containing 20% (w/w) of the compound prepared and isolated in Example 1. Polybase suppositories of other compounds of this invention can be prepared by substituting compounds of this invention for the compound isolated in Example 1.

Semi-Synthetic Glyceride Suppositories

Semi-synthetic glyceride base suppositories are prepared using Suppocire™ AI and Suppocire™ AM, two semi-synthetic glycerides of saturated fatty acids (Gattefosse Inc., Saint-Priest, France), using the fusion method.

18 g of Suppocire AI is melted in a vessel with constant stirring to 40° C. 2 g of micronized simvastatin is added to the molten base while stirring. The molten mixture is then stirred continuously for 15 minutes while maintaining the temperature at 40° C. The melt is then poured into 2 mL disposable plastic suppository molds and allowed to cool to ambient temperature, approximately 25° C. The cooled molds are then hardened in an ice bath for 1 hour. This procedure produces Suppocire AI suppositories containing 10% (w/w) simvastatin.

75 of the 20 mg Mevacor tablets are pulverized, yielding a powder containing 1.5 g lovastatin. The weight of the Mevacor tablet powder is determined, and an amount of Suppocire AM equal to 30 g less the weight of the Mevacor tablet powder is melted in a vessel with constant stirring to 40° C. The Mevacor tablet powder is added to the molten base while stirring. The molten mixture is then stirred continuously for 15 minutes while maintaining the temperature at 40° C. The melt is then poured into 2 mL disposable plastic suppository molds and allowed to cool to ambient temperature, approximately 25° C. The cooled molds are then hardened in an ice bath for 1 hour. This procedure produces Suppocire AM suppositories containing 5% (w/w) lovastatin.

Semi-synthetic glyceride suppositories using different micronized actives (e.g., simvastatin, fluvastatin, compounds of this invention, etc.) are prepared by substituting other drugs for the active compound in the above formulation.

Bioadhesive Suppositories

Carbopol-974® crosslinked acrylic acid polymers (commercially available from B. F. Goodrich, Cleveland, Ohio) and glyceryl monooleate are used as bioadhesives.

4 g micronized lovastatin is combined with 10 g of glyceryl monooleate. 6 g of Suppocire AI is melted in a vessel with constant stirring to 40° C. The combined lovastatin and glyceryl monooleate are then added to the molten base while stirring. The molten mixture is then stirred continuously for 15 minutes while maintaining the temperature at 40° C. The melt is then poured into 2 mL disposable plastic suppository molds and allowed to cool to ambient temperature, approximately 25° C. The cooled molds are then hardened in an ice bath for 1 hour. This procedure produces Suppocire AI suppositories containing 20% (w/w) lovastatin and 50% (w/w) glyceryl monooleate.

Approximately 1 g of the micronized compound prepared and isolated in Example 1 (depending on purity), or other compounds of this invention, is combined with 0.4 g Carbopol-974. 18.6 g of Suppocire AM is melted in a vessel with constant stirring to 40° C. The combined drug and Carbopol are then added to the molten base while stirring. The molten mixture is then stirred continuously for 15 minutes while maintaining the temperature at 40° C. The melt is then poured into 2 mL disposable plastic suppository molds and allowed to cool to ambient temperature, approximately 25° C. The cooled molds are then hardened in an ice bath for 1 hour. This procedure produces Suppocire AM suppositories containing 5% (w/w) of the compound from Example 1 (or other compounds of this invention) and 2% (w/w) Carbopol-974.

Example 5

This example illustrates the preparation of oral compositions. Controlled release compositions using compounds of this invention can be prepared by substituting the compounds of this invention for the active drug in the below formulation.

Time-Dependent Controlled Release

For these compositions, the thickness of a layer of slowly dissolving material determines the duration required for the tablet's coating to dissolve, and thus determines the region of the gastrointestinal tract in which the drug in the tablet core will be absorbed. Ethylcellulose, polyacrylates, polymethacrylates and Methocel® (Dow Chemical Company, Midland, Mich.) can be used as coating materials to produce tablets with different dissolution times.

The tablet cores are prepared by thoroughly mixing 200 g of simvastatin, 140 g of dibasic calcium phosphate dihydrate, 24 g of microcrystalline cellulose, and 10 g of sodium starch glycolate. 1 g of magnesium stearate is added and the composition is mixed for another 5 to 7 minutes. The granular mixture is formed into tablet cores weighing 375 mg each using a rotary tablet press. This produces tablet cores containing 200 mg simvastatin.

The tablet cores are heated to 40° C. and the coating layer is applied using a coating pan. In the first step, the cores are wetted with a binder solution containing 15% polyvinylpyrrolidone and 85% purified water. In the second step, the wetted cores are treated with a dry mixture containing 20% Methocel E5, 70% Methocel E15, 10% talc, and 1% colloidal silicon dioxide. Steps 1 and 2 are repeated until a weight gain corresponding to 20 to 60% of total tablet weight is achieved. This produces time-release tablets containing 200 mg simvastatin.

pH-Dependent Controlled Release

For these compositions, the solubility of a layer of the coating material in gastric fluid and intestinal fluid determines the where the coating will dissolve, and thus determines the region of the gastrointestinal tract in which the drug will be absorbed. Cellulose phthalate, cellulose acetate phthalate, polyacrylates or methacrylates can be used as coating materials to produce tablets and granules resistant to gastric fluid and soluble in intestinal fluid.

Method I: Enteric-Coated Tablets

The tablet cores are prepared by thoroughly mixing 200 g of lovastatin, 140 g of dibasic calcium phosphate dihydrate, 24 g of microcystalline cellulose, and 10 g of sodium starch glycolate. 1 g of magnesium sterate is added and the composition is mixed for another 5 to 7 minutes. The granular mixture is formed into tablet cores weighing 375 mg each using a rotary tablet press. This produces tablet cores containing 200 mg lovastatin.

The tablet cores are heated to 40° C. and the coating layer is applied by continuously spraying the cores with a solution containing 10% cellulose phthalate, until a weight gain corresponding to 20 to 60% of total tablet weight is achieved. This produces enteric coated 200 mg lovastatin tablets.

Method II: Tablets Composed of Enteric-Coated Granules

The compound prepared and isolated in Example 1 is placed in a large-volume mortar, and a 10% cellulose acetate phthalate—acetone solution is added drop by drop and kneaded until the acetone is nearly evaporated. A 10% (w/v) acacia solution is slowly added, and the mixture is kneaded for 7 minutes. The mass is granulated in a wet granulator and dried in a fluid-bed drier at 50° C. for 30 minutes. The granules are sieved, and granule sizes between 500 µm and 177 µm are used for tabletting. One to one mixtures of granules and microcrystalline cellulose are tabletted in a single-punch machine to produce tablets composed of cellulose acetate phthalate-coated granules of the compound from Example 1.

Enzyme-Dependent Controlled Release

For these compositions, coating materials that release active ingredients only on exposure to enzymes in the intestines, such as galactomannans and azopolymers, are used. These coating materials can be used alone or in combination with enteric coating materials.

Method I. Coated Tablets

The tablet cores are prepared by thoroughly mixing 200 g simvastatin, 140 g of dibasic calcium phosphate dihydrate, 24 g of microcystalline cellulose, and 10 g of sodium starch glycolate. 1 g of magnesium sterate is added and the composition is mixed for another 5 to 7 minutes. The granular mixture is formed into tablet cores weighing 375 mg each using a rotary tablet press. This produces tablet cores containing 200 mg simvastatin.

The tablet cores are heated to 40° C. and an azopolymer coating layer is applied by continuously spraying the cores with a solution containing 10% azopolymer, until a weight gain corresponding to 20 to 60% of total tablet weight is achieved. This produces azopolymer-coated 200 mg simvastatin tablets.

Method II: Coated Tablets Composed of Enteric-Coated Granules

Lovastatin is placed in a large-volume mortar, and a 10% cellulose acetate phthalate—acetone solution is added drop by drop and kneaded until the acetone is nearly evaporated. A 10% (w/v) acacia solution is slowly added, and the mixture is kneaded for 7 minutes. The mass is granulated in a wet granulator and dried in a fluid-bed drier at 50° C. for 30 minutes. The granules are sieved, and granule sizes between 500 µm and 177 µm are used for tabletting. One to one mixtures of granules and microcrystalline cellulose are tabletted in a single-punch machine to produce tablets cores composed of enteric-coated lovastatin granules.

The tablet cores are heated to 40° C. and the coating layer is applied by continuously spraying the cores with a solution containing 10% galactomannan, until a weight gain corresponding to 20 to 60% of total tablet weight is achieved. This produces galactomannan coated tablet cores composed of enteric-coated lovastatin granules.

Example 6

This example illustrates treating ulcerative colitis with lovastatin.

Statin and statin derivatives described in the current invention can be used in combination with all the current and future therapies to provide a more cost effective, safe and long term therapy for inflammatory disorders such as inflammatory bowel disease (see, Neurath M F, *Achivum Immunologiae et Therapiae Experimentalis*, 2000, 48:81-84; Garnett W R et al, *Am J Heath-Syst Pharm*, 58(40);307-319; Scrip Reports on Gastrointestinal Disorders: New Therapies for the New Millenium, 2000). Lovastatin enema will be administered for patients afflicted with left-sided colitis whereas suppositories are effective in all patients suffering from UC. (see Dash et al., Int. J. Pharm. 190 (1999) 21-34).

Example 7

This example illustrates maintenance therapy for inflammatory disorders using lovastatin.

Chronic inflammatory disorders such as ulcerative colitis, rheumatoid arthritis, Crohn's disease, psoriasis, etc. typically relapse after a successful course of treatment. A safe and effective maintenance therapy will greatly improve patient health, quality of life and reduce medical cost.

Patients diagnosed with active chronic Crohn's disease are treated with methotrexate therapy to achieve disease remission. Remission is defined as no need for oral prednisone and presence of a score of 150 or less on the Crohn's Disease Activity Index. This index incorporates eight items: the number of liquid or very soft stools in the seven days preceding the assessment, the severity of abdominal pain, general well-being, the presence or absence of an abdominal mass or extra-intestinal manifestation of the disease, the use of opiates to treat diarrhea, hematocrit, and weight. Scores in this index can range from 0 to approximately 600. Higher scores indicate greater disease activity. A score of 150 or less is considered to indicate clinical illness and a decrease of 70 to 100 points is clinically meaningful (see, Summers R W et al, *Gastroenterology*, 77:847-879, 1979; Rutgeerts P et al., *N. Engl. J Med.*, 331:842-845, 1994).

Upon reaching remission, the subject takes lovastatin orally (Mevacor, 20–1000 mg) every day, in addition to one or more of the following: controlled release lovastatin tablet(s) targeting specific disease sites, lovastatin enema(s), or lovastatin rectal suppositories on a regular basis. On average, 50-60% of Crohn's disease subjects in remission relapse in 40 weeks. Subjects treated with lovastatin have a longer remission time between relapse and have less severe disease activity. Subjects taking lovastatin in combination with methotrexate could be in even longer remission or have better quality of life due to reduced methotrexate-induced side effects. Since lovastatin, other statins, and most likely their related derivatives have very good safety profiles with minimal side effect, using these compounds alone or in combination with the current therapy can provide patients with the best maintenance therapy for Crohn's disease, and most likely, other chronic inflammatory disorders in mammals. Alternatively, statins can be administered in parallel with growth hormone therapy (sometropin, Humatrope, Eli Lilly) (see, Slonim A E et al, N Engl J Med, 342:1633-1637, 2000) so that the statin can prevent the recurrence of inflammation while growth hormone facilitates regrowth of the colonic and intestinal mucosa.

Example 8

This example illustrates preventing postoperative recurrence of Crohn's disease with compounds of this invention.

Recurrence of Crohn's disease lesions in the neo-ileum after apparently curative resection frequently occurs after surgery. Subjects with a history of ileal and ilealcecal surgical resection receive compounds of this invention orally or locally immediately following surgery and on a regular basis thereafter. Subjects are monitored clinically using the Crohn's disease activity index every three months and by imaging methods every 6 months.

Example 9

This example illustrates treating patients afflicted with atopic dermatitis (AD) with cream containing lovastatin.

Atopic dermatitis is a chronically relapsing, pruritic inflammatory skin disorder. While severe atopic dermatitis is characterized by severe exudative papules, intense pruritus and erythema lichenification and excoriation, mild-to-moderate atopic dermatitis is typically manifested as red patches of dry skin with excoriation, infiltration and papulation. Patients diagnosed with atopic dermatitis apply the cream to the afflicted area(s), either twice or three times daily. The overall improvement of AD can be observed as early as two to three weeks following the treatment. The improvement can be evaluated by Eczema Area Severity Index (see, Hanifin J M et al, *Current Therapeutic Research*, 59(4):227-233; Paller A et al, *J Am Acad Dermatol* 2001 Jan;44(1 Suppl):S47-57); Hanifin J M et al, *J Am Acad Dermatol* 2001 Jan;44(1 Suppl):S28-38); a reduction of 20–25% of the disease severity is considered improvement. The cream can also be used as maintenance therapy to prevent the relapse of AD, used as follow up therapy to the two-week course of steroid therapy, and as combination therapy to reduce the steroid dose. A safer and effective therapy will be extremely useful in pediatric population where steroid use could lead to growth delay and other debilitating steroid-induced side effects.

Example 10

This example illustrates osteoporosis prevention in patients diagnosed with rheumatoid arthritis.

In order to prevent the development of osteoporosis, both male and female patients who have been diagnosed with rheumatoid arthritis are using a formulation of a composition of the present invention for example, a topical cream, prophylactically on a regular basis. Prior to the initiation of the statin, areal bone mineral density is measured by dual-energy x-ray absorptiometry (DXA). Patients who have low bone mineral density and are at high risk for osteoporosis are selected for statin therapy. Risk factors include 1) current use of anticonvulsants, 2) inability to rise from a chair without using arms, 3) tachycardia at rest, 4) maternal history of hip fracture, 5) history of hyperthyroidism, 6) insufficient weight-bearing exercise, older age ($\geq 65$ yrs old), 7) history of fracture at any site after 50 years of age, 8) poor depth perception, 9) high daily caffeine intake, 10) poor visual contrast sensitivity, 11) above average height at 25 years of age, and 12) current weight than that at 25 years of age. Smokers and individuals with high consumption of alcohol ($\geq 7$ drinks per week) should also take lovastatin medication to prevent further loss of bone mineral density.

Patients suffering from low bone mineral density due to other causes (see, Gamble C L, *Geriatrics*, 1995; 50:24-33), such as hormonal deficiency, surgery, or other medical illness such as anorexia nervosa, hyperthyroidism, and the like can also take statin to prevent future bone loss.

Example 11

This example illustrates preparation of carboxymethylcellulose formulation.

Low viscosity sodium carboxymethylcellulose (CMC) purchased from British Drug House (Poole, UK), was added to purified water at a concentration of 0.5% weight per volume CMC. The CMC/water mixture was allowed to stir overnight at room temperature to completely disperse and solubilize the CMC. Powdered lovastatin 99.3% (Sinochem Jiangsu, Nanjing, PRC) was then added to the CMC solution at a concentration of 10 mg/ml. The lovastatin/CMC suspension was homogenized for 15 to 20 seconds in a Polytron Homogenizer (Brinkmann Instruments, Westbury, N.Y.). The resulting homogenized lovastatin/CMC suspension was dosed immediately.

Example 12

This example illustrates preparation of propylene carbonate formulation.

Powdered lovastatin 99.3% (Sinochem Jiangsu, Nanjing, PRC) was added to 45C propylene carbonate (Burdic and Jackson 99.9%) at a concentration of 30 mg/ml and mixed until dissolved. It was cooled to room temperature and immediately filled into 10 ml brown screw capped vials (2 ml each vial) and stored at room temperature. Next a diluent solution of suspending agents was prepared by adding Tween 40 USP/NF (Spectrum Chemicals, Gardina, Calif.) 5 g/100 g, and Span 80 NF (Spectrum Chemicals, Gardina, Calif.) 5 g/100 g, to 70C purified water and mixing until uniform. The diluent solution was stored at room temperature until used. Immediately before dosing, the lovastain/PC suspension was mixed 1:2 (vol:vol) with the sorbitan monooleate/polycarbonate solution and vortex mixed for one minute.

Example 13

This example illustrates the reduction of trinitrobenzene sulfonic acid-induced colitis by lovastatin.

Human inflammatory bowel disease (IBD) is a chronic relapsing and remitting disease of unknown etiology that affects individuals of both sexes throughout life. The factors contributing to the two main forms of the disease, Crohn's disease and ulcerative colitis, are complex and probably involve abnormal immune responses and commensal intestinal microflora. A number of experimental models of intestinal inflammation have been developed, including those based on intracolonic instillation of 2,4,6-trinitrobenzene sulfonic acid (TNBS). TNBS-induced colitis shares many of the histopathological and clinical features of Crohn's disease, i.e. it is to some extent immune-mediated, produces long lasting ulcerative damage and thickening of the bowel wall, granulocyte and mononuclear cell infiltration and granuloma formation, and transmural inflammation of the mucosa, (Morris et al., Gastroenterology 96:795–803, 1989). This model has been widely used to evaluate potential treatments for colonic inflammation.

In the present study, the local anti-inflammatory effects of lovastatin were assessed in the rat TNBS-induced colitis model. Colitis was induced in male Wistar rats weighing 175–225 g by intracolonic instillation of the hapten TNBS (60 mg/ml) in 0.5 ml of 50% ethanol. Groups of 8 rats received the lovastatin formulation prepared in Example 11 (50 mg/kg/day), a positive control, budesonide (2.5 mg/kg/day), or vehicle (0.5% sodium carboxymethylcellulose) intracolonically 1 hour after induction of colitis, and at 12 h intervals thereafter for two weeks. The rats received 0.5 ml of test drug or vehicle at each dosing. On day 14 after induction of colitis, the animals were euthanized and the distal colon was removed and pinned out on a wax platform. The presence or absence of diarrhea was noted, as was the presence and severity of adhesions between the colon and other organs. The severity of colonic damage was scored using the criteria described in Appleyard and Wallace, Am. J. Physiol. 269 (Gastrointest. Liver Physiol. 32): G119–G125, 1995. After the scoring was completed, a sample of colonic tissue was excised and frozen at −20° C. for subsequent measurement of myeloperoxidase (MPO) activity, as an index of granulocyte infiltration.

Lovastatin produced a significant ($p<0.05$) reduction of the colonic damage score and of the global colitis score, which also includes maximal bowel thickness, presence/absence of diarrhea, and presence/severity of adhesions (Figure ?). Lovastatin also reduced colonic MPO activity, reflecting less polymorphonuclear leukocyte infiltration.

Example 14

This example illustrates the Store-Operated Calcium Influx Assay.

Jurkat cells were washed once with PBS and once with Loading Buffer (140 mM NaCl, 5 mM KCl, 1 mM CaCl2, 1 mM MgCl2, 10 mM glucose, 20 mM HEPES, 0.1% BSA, pH 7.4). Cells ($4 \times 10^6$/ml) were resuspended in Loading Buffer and loaded with 1 $\mu$M of the $Ca^{2+}$-sensitive dye, Fura-2AM (Molecular Probes, Inc.) for 1 hour at 37° C. Loaded cells were then washed three times with the loading buffer and incubated with 0.3 $\mu$M thapsigargin and 2 mM EGTA for 30 minutes to deplete intracellular calcium storage pools. Cells were finally washed two times and resuspended in calcium-free Loading buffer at a density of $1 \times 10^6$/ml. Calcium influx analyses were performed using a Perkin-Elmer LS 55 luminescence spectrometer. Briefly, 2 mls of cells were placed into a cuvette and monitored with constant stirring, using alternating excitation wavelengths of 340 and 380 nm, and an emission wavelength of 510 nm. The intracellular free Ca2+ concentration was calculated from the 340/380 nm fluorescence ratio (Grynkiewicz et al., 1985). Compounds or vehicle were added to the cells and incubated 10 min, and calcium influx initiated by the addition of $CaCl_2$ to a final concentration of 5 mM.

Example 15

This example demonstrates that lovastatin inhibits JNK phosphorylation induced by PMA+ionomycin and lovastatin strongly inhibits the ability of ionomycin to synergistically activate NF-κB.

Figure 19:
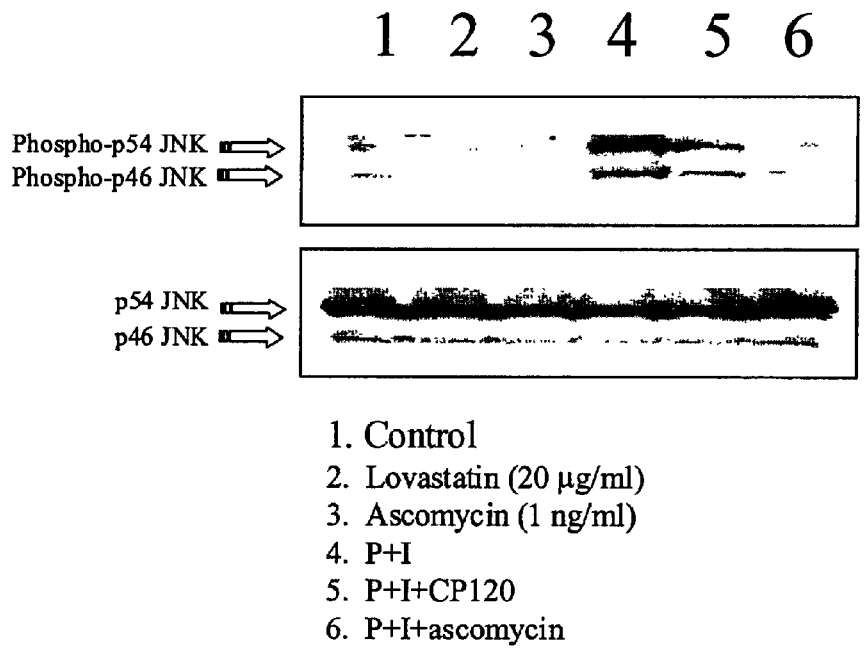
FIG. 19A illustrates inhibition of JNK phosphorylation by lovastatin; B illustrates inhibition of calcium-dependent NF-kB Activity by lovastatin.
Figure 19:
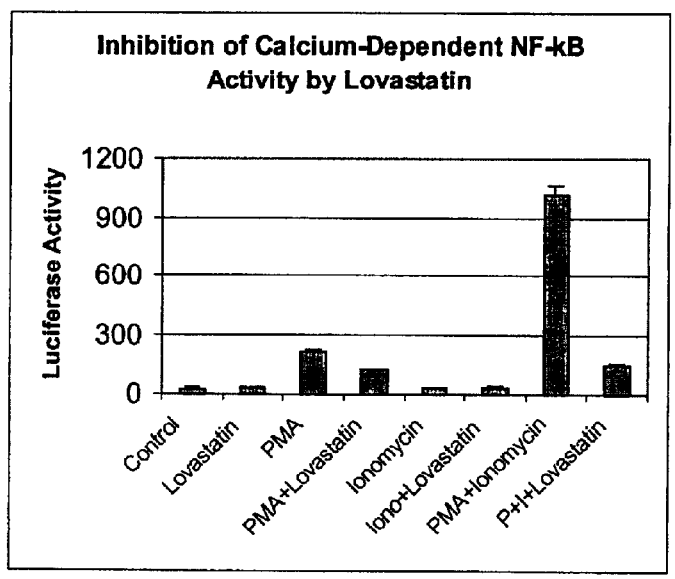

FIG. 19A shows the results of Jurkat T cells having been pre-incubated with lovastatin (20 mg/ml; lanes 2 and 5), ascomycin (1 ng/ml; lanes 3 and 6), or vehicle control (lanes 1 and 4) for 15 min, then stimulated with PMA (20 ng/ml) and ionomycin (1 mg/ml) for 30 min. Cells were harvested, lysates prepared, and proteins Western blotted using antibodies directed against JNK or phospho-JNK (Thr183/Thr185). The results demonstrate that lovastatin inhibits JNK phosphorylation induced by PMA+ionomycin. Lovastatin has little effect on PMA-induced JNK phosphorylation.

FIG. 19B shows the results of Jurkat T cells being transiently co-transfected with the reporter vectors pNF-κB-luc and pRSV-ren using SuperFect. The next day, cells were preincubated with lovastatin (20 $\mu$g/ml) or vehicle control for 15 min, and then stimulated with PMA (20 ng/ml), ionomycin (1 $\mu$g/ml), or PMA+ionomycin for 5 hr. The cells were harvested, lysed, and lysates assayed for firefly luciferase and Renilla luciferase activity measured in a luminometer. The results demonstrate that PMA, but not ionomycin alone, stimulates NF-κB activity in Jurkat cells, and that NF-κB activity is synergistically upregulated in the presence of both ionomycin+PMA. Lovastatin strongly inhibits the ability of ionomycin to synergistically activate NF-κB.

Example 16

This example illustrates the efficacy of compound Ia;20;12;13 used orally for the treatment of arthritis.

1. Composition: The composition tested comprised compound Ia;20;12;13 in tablet form.

2. Subjects: Six subjects, four males and two females, will be recruited for this experiment aged between 50 to 89 years. The subjects suffered from, and had been diagnosed with, most common varieties of arthritis including osteoarthritis and rheumatoid arthritis and exhibited typical arthritic manifestations including pain and inflammation of the joints. In some instances, the subjects will already taking other medication including Analgesics, Non Steroidal Anti Inflammatory Drugs, Disease Modifying Drugs and Corticosteroids. The subjects maintained any pre-existing drug regimes.

3. Administration Regime: Initially, the subjects were instructed to take the composition once daily. After the arthritic pain began to dissipate the subjects will be instructed to cut back the application and apply only when they felt a recurrence of pain. In most instances this will result in a twice weekly or weekly application.

4. Assessment: The subjects will be instructed to assess any change in the level of any arthritic manifestation. For the purposes of the experiment the arthritic manifestations will be assessed by reference to the level of pain and immobility in the arthritic joint and the general well being of the subject. The last criteria encompassed both the physical and mental state of the subject.

5. Results: In all instances, the subjects observed that the application of the inventive composition resulted in a readily apparent reduction in the level of pain and immobility. After two weeks of an initial twice daily application, subjects 1, 2, 3 and 4 showed a marked improvement in the reduction of arthritic manifestations.

Example 17

This example illustrates the efficacy of compound Ia;20;12;13 used for the treatment of asthma.

The compound is administered via the inhalation route as an aerosol one hour before antigen challenge in acute responder sheep. There is significant inhibition of allergic bronchoconstriction and the late phase response (the inflammatory component of asthma) by the administered of the compound.

The following protocol is a well-known and art accepted animal model for measurement of antigen-induced asthmatic treatments. Five allergic sheep, with previously documented acute bronchoconstrictor response to Ascaris suum antigen, are used for all studies. The sheep were intubated with a cuffed nasotracheal tube and pulmonary airflow resistance is measured by the esophageal balloon catheter technique, while thoracic gas volume was measured by body plethysmography. To assess the normal or baseline airway responsiveness of the sheep, cumulative dose response curves to inhaled carbachol were performed. Treatment with the inventive compound maintains the airway responsiveness levels at the baseline or normal responsiveness levels of the sheep. Treatment with the inventive compound can attenuate an antigen-induced asthma attack.

Example 18

This example illustrates the efficacy of a δ-lactone-containing statin e.g., lovastatin, for the treatment of asthma in aerosol formulation.

For administration in an aerosol formulation, the dose of SOC inhibitor can generally be lower than the dose used for systemic administration. For example, the SOC inhibitor can be administered at a dose between about 0.1 mg to about 80 mg. The SOC inhibitor can be administered at a dose of greater than 0.1 mg per day, for example, about 1.5 mg per day or more, about 2.0 mg per day or more, about 7 mg per day or more, about 16 mg per day or more, about 25 mg per day or more, about 40 mg per day or more, about 60 mg per day or more, about 70 mg per day or more, or about 80 mg per day. Treatment with the compound can attenuate the late phase response of asthma (the inflammatory component of asthma).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating an inflammatory disease or reducing an inflammatory reaction, said method comprising:

administering a SOC inhibitor, thereby treating said inflammatory disease or reducing said inflammatory reaction, wherein said SOC inhibitor is a compound selected from the group consisting of:

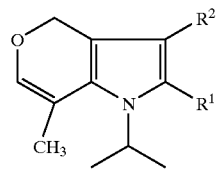

Ia

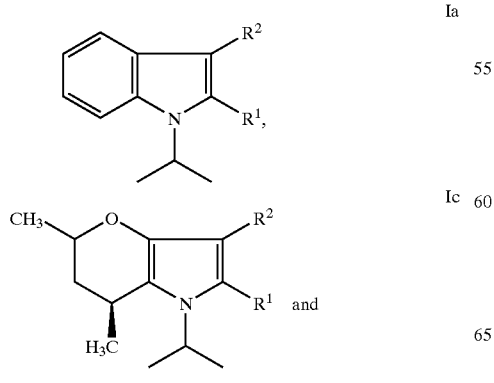

Ic and

-continued

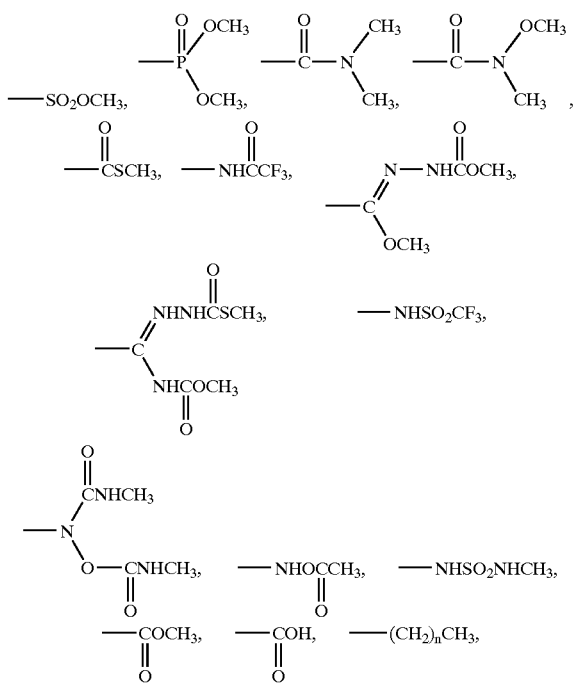

Id wherein:
R$^1$ is a (C$_4$–C$_{18}$)alkylene having at least 2 sites of unsaturation and substituted with 1 R$^3$,
wherein R$^3$ a member selected from the group consisting of:

wherein n is about 1 to about 10, and —CH$_3$; and
R$^2$ is a member selected from the group consisting of optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy, wherein each substituent is independently selected from the group consisting of hydroxyl, bromo, fluoro, chloro, iodo, mercapto or thio, cyano, cyanoamido, alkylthio, aryl, carboxyl, carbalkoyl, alkyl, alkenyl, nitro, amino, alkoxyl and amido.

2. The method of claim 1, wherein said compound is:

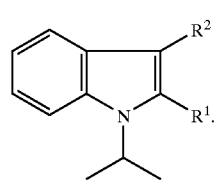

Ia

3. The method of claim 1, wherein R$^1$ is a member selected from the group consisting of:
—(CH=CH)$_2$—(CH)$_x$—R$^3$, wherein x is about 1 to about 14, and —(CH=CH)$_3$—R$^3$.

4. The method of claim 1, wherein R² is independently a member selected from the group consisting of optionally substituted alkoxy, acyl, optionally substituted aryl, optionally substituted arylalkyl, optionally substituted heteroarylalkyl, and optionally substituted heteroarylalkoxy.

5. The method of claim 4, wherein R² is a member selected from the group consisting of consisting of:

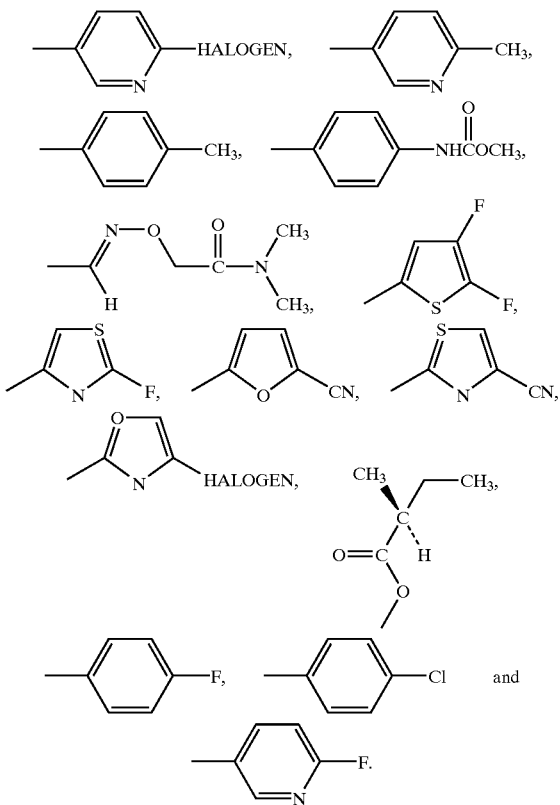

6. The method of claim 5, wherein R² is p-fluorophenyl.

7. The method of claim 1, wherein said compound has the formula:

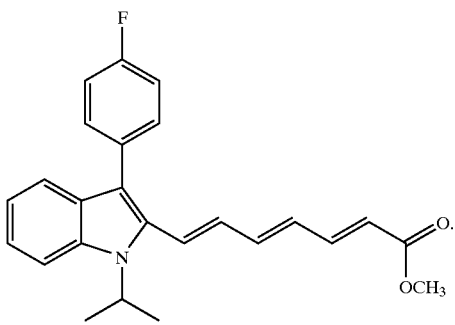

8. The method of claim 1, wherein said inflammatory disease or inflammatory reaction is a skin disorder.

9. The method of claim 8, wherein said skin disorder is selected from the group consisting of atopic dermatitis, psoriasis, neurogenic inflammation, skin photodamage, a cell carcinoma, keratosis, and a disorder of keratinization.

10. The method of claim 1, wherein said inflammatory disease or inflammatory reaction is an inflammatory pulmonary disease or reaction.

11. The method of claim 10, wherein said inflammatory pulmonary disease or reaction is selected from the group consisting of asthma, allergic rhinitis, chronic obstructive pulmonary disease and adult respiratory distress syndrome.

12. The method of claim 1, wherein said inflammatory disease or inflammatory reaction is an inflammatory musculoskeletal disease or reaction.

13. The method of claim 12, wherein said inflammatory musculoskeletal disease is a member selected from the group consisting of psoriatic arthritis, osteoarthritis, and osteoporosis.

14. The method of claim 1, wherein said inflammatory disease or inflammatory reaction is an inflammatory gastrointestinal or urogenital disease or reaction.

15. The method of claim 14, wherein said inflammatory gastrointestinal or urogenital disease or reaction is a member selected from the group consisting of inflammatory bowel disease, enterocolitis, gastritis, vaginitis, and interstitial cystitis.

16. The method of claim 1, wherein said inflamation is caused by autoimmune disease or reaction.

17. The method of claim 16, wherein said autoimmune disease is a member selected from the group consisting of multiple sclerosis, type II diabetes, lupus, and rheumatoid arthritis.

18. The method of claim 1, wherein said inflamation is caused by transplantation treatment.

19. A compound selected from the group consisting of:

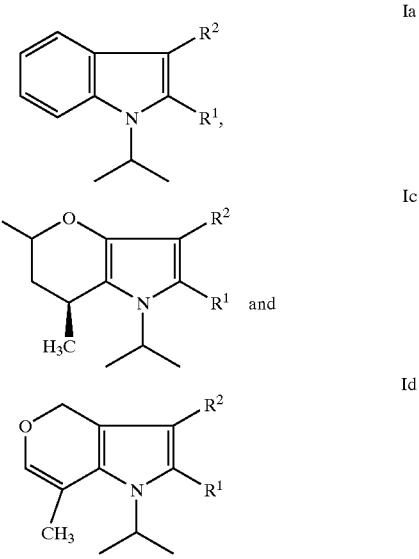

wherein:

R¹ is a (C₄–C₁₈)alkylene having at least 2 sites of unsaturation and substituted with 1 R³, wherein R³ is a member selected from the group consisting of:

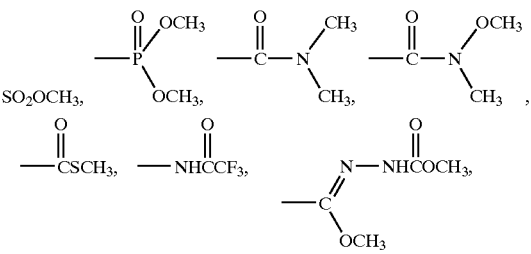

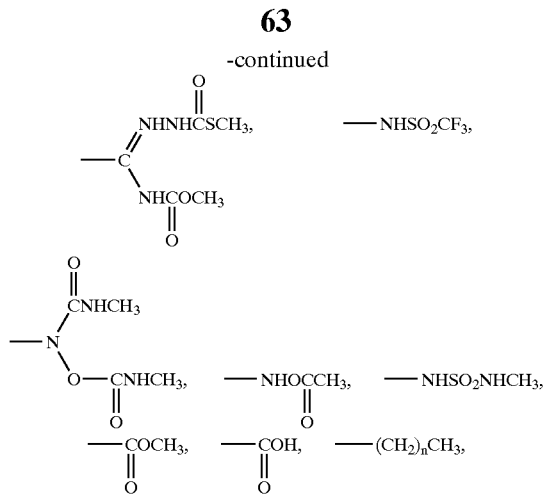

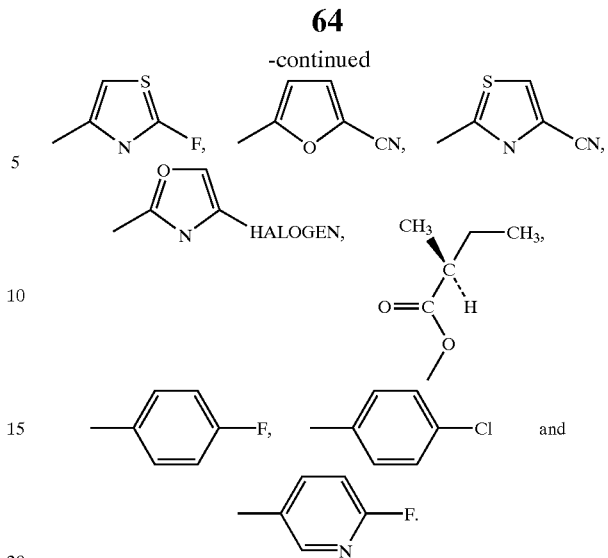

wherein n is about 1 to about 10, and —CH$_3$; and

R$^2$ is a member selected from the group consisting of optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy, wherein each substituent is independently selected from the group consisting of hydroxyl, bromo, fluoro, chloro, iodo, mercapto or thio, cyano, cyanoamido, alkylthio, aryl, carboxyl, carbalkoyl, alkyl, alkenyl, nitro, amino, alkoxyl and amido.

20. The compound of claim 19, wherein said compound is

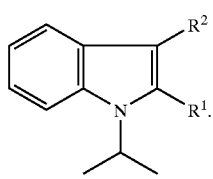

Ia

21. The compound of claim 19, wherein R$^1$ is a member selected from the group consisting of:

—(CH=CH)$_2$—(CH$_2$)$_x$—R$^3$, wherein x is about 1 to about 14, and —(CH=CH)$_3$—R$^3$.

22. The compound of claim 21, wherein R$^2$ is independently a member selected from the group consisting of optionally substituted alkoxy, acyl, optionally substituted aryl, optionally substituted arylalkyl, optionally substituted heteroarylalkyl, and optionally substituted heteroarylalkoxy.

23. The compound of claim 22, wherein R$^2$ is a member selected from the group consisting of consisting of:

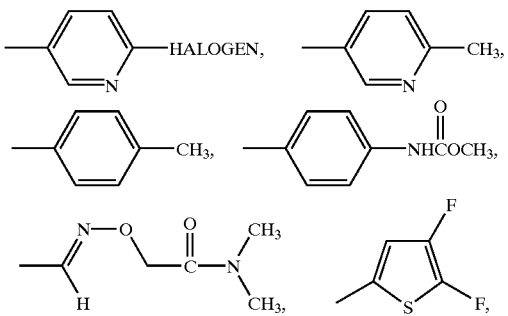

24. The compound of claim 23, wherein R$^2$ is p-fluorophenyl.

25. The compound of claim 19, wherein said compound has the formula:

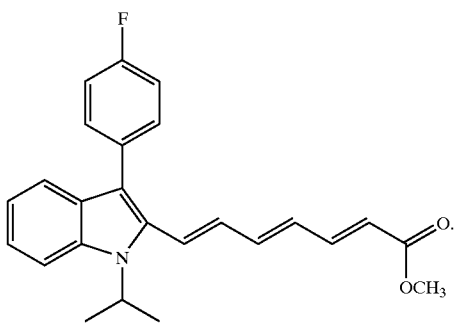

26. A pharmaceutical composition, said pharmaceutical composition comprising a compound selected from the group consisting of:

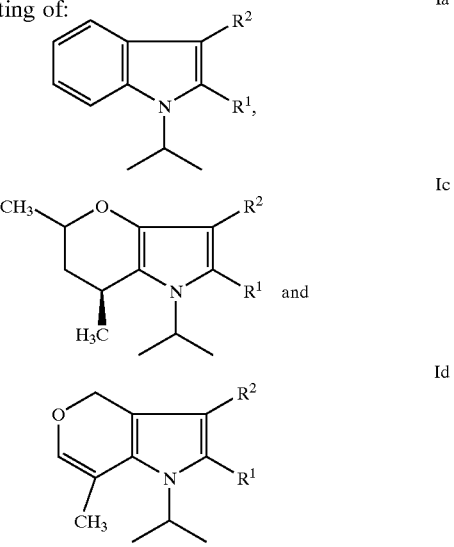

wherein:

R$^1$ is a (C$_4$–C$_{18}$)alkylene having at least 2 sites of unsaturation and substituted with 1 R$^3$, wherein R$^3$ is a member selected from the group consisting of:

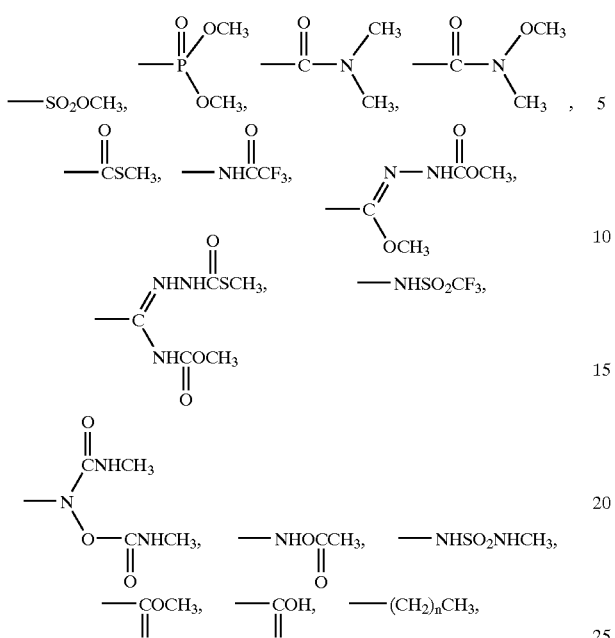

wherein n is about 1 to about 10, and —CH₃;

R² is a member selected from the group consisting of optionally substituted (C₁–C₆)alkyl, optionally substituted (C₁–C₆)alkoxy, acyl, optionally substituted aryl, optionally substituted arylalkyl, optionally substituted heteroarylalkyl, and optionally substituted heteroarylalkoxy, wherein each substituent is independently selected from the group consisting of hydroxyl, bromo, fluoro, chloro, iodo, mercapto or thio, cyano, cyanoamido, alkylthio, aryl, carboxyl, carbalkoyl, alkyl, alkenyl, nitro, amino, alkoxyl and amido; and a pharmaceutically acceptable excipient therefore.

27. The pharmaceutical composition of claim 26, wherein said compound is:

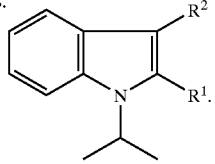

28. The pharmaceutical composition of claim 26, wherein R¹ is a member selected from the group consisting of:

—(CH=CH)₂—(CH₂)ₓ—R³, wherein x is about 1 to about 14, and —(CH=CH)₃—R³.

29. The pharmaceutical composition of claim 28, wherein R² is independently a member selected from the group consisting of optionally substituted alkoxy, acyl, optionally substituted aryl, optionally substituted arylalkyl, optionally substituted heteroarylalkyl, and optionally substituted heteroarylalkoxy.

30. The pharmaceutical composition of claim 28, wherein R² is a member selected from the group consisting of consisting of:

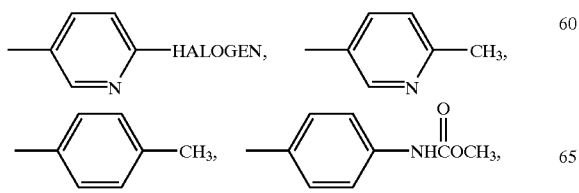

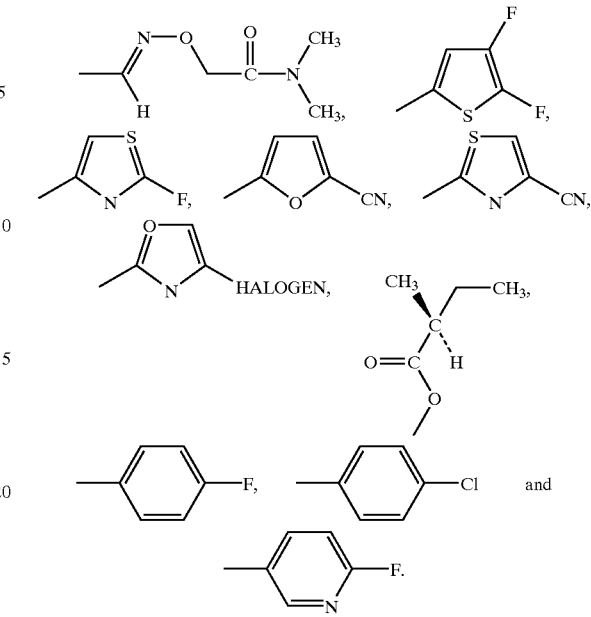

31. The pharmaceutical composition of claim 26, wherein said compound has the formula:

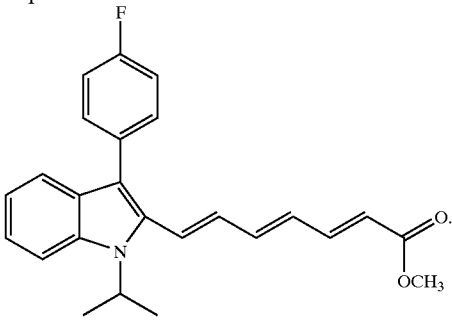

32. A method for blocking calcium influx from the extracellular space, said method comprising:

contacting a cell with a store operated calcium influx (SOC) inhibitor, thereby blocking calcium influx from the extracellular space, wherein said SOC inhibitor is a compound selected from the group consisting of:

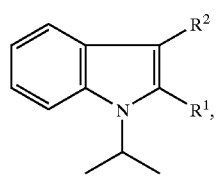

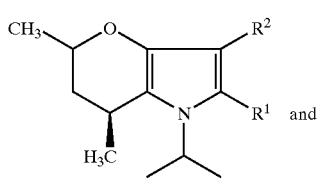

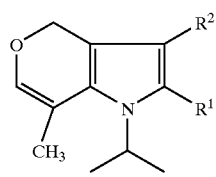

wherein:

R$^1$ is a (C$_4$–C$_{18}$)alkylene having at least 2 sites of unsaturation and substituted with 1 R$^3$, wherein R$^3$ is a member selected from the group consisting of:

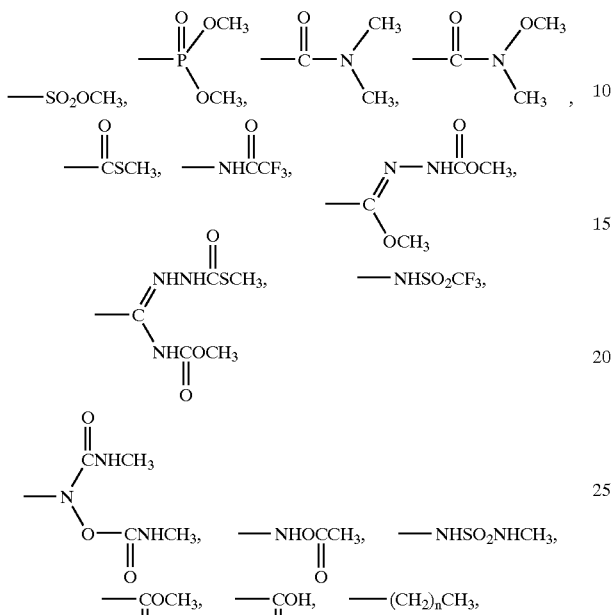

wherein n is about 1 to about 10, and —CH$_3$; and

R$^2$ is a member selected from the group consisting of optionally substituted (C$_1$–C$_6$)alkyl, optionally substituted (C$_1$–C$_6$)alkoxy, acyl, optionally substituted aryl, optionally substituted arylalkyl, optionally substituted heteroarylalkyl, and optionally substituted heteroarylalkoxy, wherein each substituent is independently selected from the group consisting of hydroxyl, bromo, fluoro, chloro, iodo, mercapto or thio, cyano, cyanoamido, alkylthio, aryl, carboxyl, carbalkoyl, alkyl, alkenyl, nitro, amino, alkoxyl and amido.

33. The method of claim 32, wherein said compound is

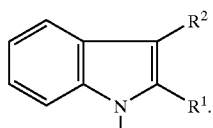

Ia

34. The method of claim 32, wherein R$^1$ is a member selected from the group consisting of:

—(CH=CH)$_2$—(CH$_2$)$_x$—R$^3$, wherein x is about 1 to about 14, and —(CH=CH)$_3$—R$^3$.

35. The method of claim 34, wherein R$^2$ independently a member selected from the group consisting of optionally substituted alkoxy, acyl, optionally substituted aryl, optionally substituted arylalkyl, optionally substituted heteroarylalkyl, and optionally substituted heteroarylalkoxy.

36. The method of claim 34, wherein R$^2$ a member selected from the group consisting of consisting of:

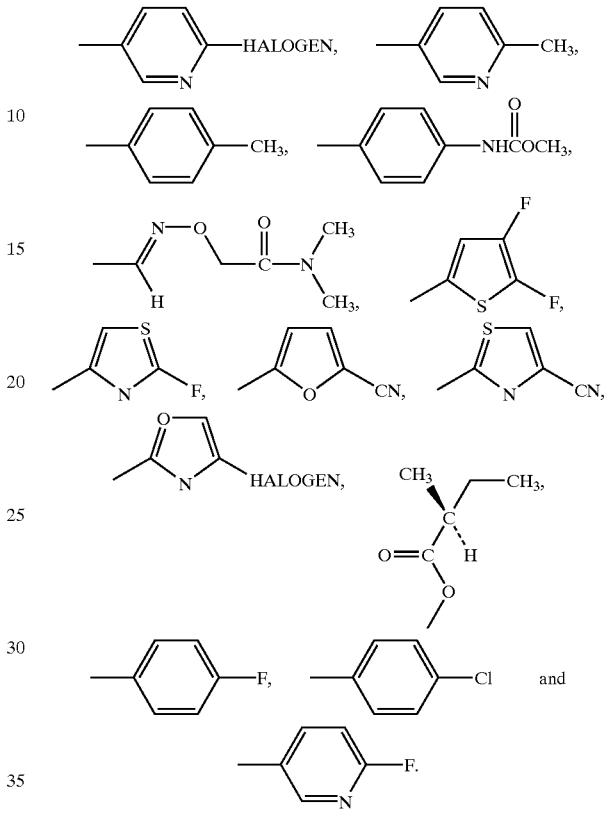

37. The method of claim 32, wherein said compound has the formula:

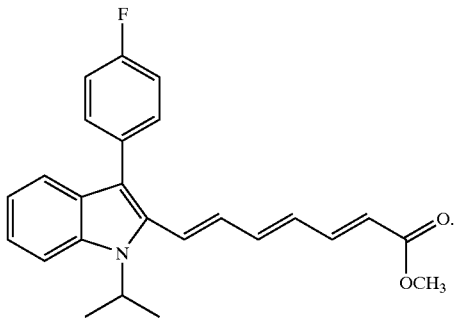

* * * * *